(12) United States Patent
Dickinson et al.

(10) Patent No.: US 9,314,329 B2
(45) Date of Patent: Apr. 19, 2016

(54) METHODS AND SYSTEMS FOR PROVIDING OR MAINTAINING FLUID FLOW THROUGH BODY PASSAGES

(71) Applicant: LimFlow GmbH, Dresden (DE)

(72) Inventors: Robert Julian Dickinson, London (GB); Roberto Ferraresi, Milan (IT); Steven Kum, Singapore (SG); Timothy Lenihan, Hradec Kralove (CZ); Andrew Robert Pacey, Stevenage (GB); Martin Terry Rothman, Santa Rosa, CA (US)

(73) Assignee: LimFlow GmbH, Dresden (DE)

( * ) Notice: Subject to any disclaimer, the term of this patent is extended or adjusted under 35 U.S.C. 154(b) by 0 days.

(21) Appl. No.: 14/834,813

(22) Filed: Aug. 25, 2015

(65) Prior Publication Data

US 2015/0374486 A1  Dec. 31, 2015

Related U.S. Application Data

(63) Continuation of application No. PCT/US2014/019607, filed on Feb. 28, 2014, and a continuation-in-part of application No. 13/791,185, filed on Mar. 8, 2013, now abandoned.

(60) Provisional application No. 61/901,753, filed on Nov. 8, 2013.

(51) Int. Cl.
*A61F 2/07* (2013.01)
*A61F 11/00* (2006.01)
(Continued)

(52) U.S. Cl.
CPC . *A61F 2/07* (2013.01); *A61B 17/11* (2013.01); *A61B 17/22* (2013.01); *A61F 2/844* (2013.01);
(Continued)

(58) Field of Classification Search
CPC ......... A61F 2/95; A61F 2/958; A61F 2/2418; A61F 2/06; A61F 2/07; A61B 18/1492
See application file for complete search history.

(56) References Cited

U.S. PATENT DOCUMENTS

| | | |
|---|---|---|
| 4,249,539 A | 2/1981 | Vilkomerson et al. |
| 4,757,821 A | 7/1988 | Snyder |

(Continued)

FOREIGN PATENT DOCUMENTS

| | | |
|---|---|---|
| WO | WO 00/09041 | 2/2000 |
| WO | WO 00/33770 | 6/2000 |

(Continued)

OTHER PUBLICATIONS

Alexandrescu et al., "Deep calf veins arterialization for inferior limb preservation in diabetic patients with extended ischaemic wounds, unfit for direct arterial reconstruction: preliminary results according to an angiosome model of perfusion", *Cardiovasc. Revasc. Med.*, Jan.-Feb. 2011, vol. 12, pp. 10-19.

(Continued)

*Primary Examiner* — Jason-Dennis Stewart
(74) *Attorney, Agent, or Firm* — Knobbe Martens Olson & Bear, LLP

(57) ABSTRACT

A device includes a first end portion, a second end portion, an intermediate portion, and a graft material. The first end portion has a first end diameter. The second end portion has a second end diameter smaller than the first end diameter. The first end portion comprises a first material. The second end portion comprises a second material different than the first material. The intermediate portion is between the first end portion and the second end portion. The intermediate portion tapers between the first end portion and the second end portion. The graft material is coupled to at least the intermediate portion.

20 Claims, 23 Drawing Sheets

(51) Int. Cl.

| | | |
|---|---|---|
| A61M 27/00 | (2006.01) | |
| A61B 17/11 | (2006.01) | |
| A61F 2/95 | (2013.01) | |
| A61F 2/844 | (2013.01) | |
| A61B 17/22 | (2006.01) | |
| A61F 2/06 | (2013.01) | |

(52) U.S. Cl.
CPC ............... *A61F 2/95* (2013.01); *A61M 27/002* (2013.01); *A61B 2017/1107* (2013.01); *A61B 2017/1139* (2013.01); *A61B 2017/22097* (2013.01); *A61F 2002/068* (2013.01); *A61F 2230/0067* (2013.01); *A61F 2230/0069* (2013.01)

(56) References Cited

U.S. PATENT DOCUMENTS

| | | |
|---|---|---|
| 4,952,215 A | 8/1990 | Ouriel et al. |
| 5,047,041 A | 9/1991 | Samuels |
| 5,304,189 A | 4/1994 | Goldberg et al. |
| 5,591,226 A | 1/1997 | Trerotola et al. |
| 5,639,278 A | 6/1997 | Dereume et al. |
| 5,720,776 A | 2/1998 | Chuter et al. |
| 5,759,174 A | 6/1998 | Fischell et al. |
| 5,800,522 A | 9/1998 | Campbell et al. |
| 5,897,495 A | 4/1999 | Aida et al. |
| 5,951,599 A | 9/1999 | McCrory |
| 6,190,353 B1 | 2/2001 | Makower et al. |
| 6,193,745 B1 | 2/2001 | Fogarty et al. |
| 6,287,336 B1 | 9/2001 | Globerman et al. |
| 6,302,875 B1 | 10/2001 | Makower et al. |
| 6,464,665 B1 | 10/2002 | Heuser |
| 6,475,170 B1 | 11/2002 | Doron et al. |
| 6,475,226 B1 | 11/2002 | Belef et al. |
| 6,569,193 B1 | 5/2003 | Cox et al. |
| 6,726,677 B1 | 4/2004 | Flaherty et al. |
| 6,858,038 B2 | 2/2005 | Heuser |
| 6,863,684 B2 | 3/2005 | Kim et al. |
| 7,018,401 B1 | 3/2006 | Hyodoh et al. |
| 7,166,088 B2 | 1/2007 | Heuser |
| 7,179,250 B2 | 2/2007 | Heuser |
| 7,300,459 B2 | 11/2007 | Heuser |
| 7,402,141 B2 | 7/2008 | Heuser |
| 7,582,108 B2 | 9/2009 | Hierlemann et al. |
| 7,621,902 B2 | 11/2009 | Nita et al. |
| 7,670,329 B2 | 3/2010 | Flaherty et al. |
| 7,780,719 B2 | 8/2010 | Killion et al. |
| 7,849,860 B2 | 12/2010 | Makower et al. |
| 7,966,057 B2 | 6/2011 | Macaulay et al. |
| 8,066,674 B2 | 11/2011 | Heuser |
| 8,142,387 B2 | 3/2012 | Heise et al. |
| 8,172,861 B2 | 5/2012 | Fuller et al. |
| 8,197,499 B2 | 6/2012 | Gurtner et al. |
| 8,216,259 B2 | 7/2012 | Gurtner et al. |
| 8,226,592 B2 | 7/2012 | Brenneman et al. |
| 8,231,646 B2 | 7/2012 | Kassab et al. |
| 8,251,943 B1 | 8/2012 | Spencer et al. |
| 8,282,591 B2 | 10/2012 | Khan et al. |
| 8,343,087 B2 | 1/2013 | Formichi |
| 8,343,089 B2 | 1/2013 | Chang |
| 8,361,101 B2 | 1/2013 | Kassab |
| 8,414,516 B2 | 4/2013 | Chang |
| 8,439,963 B2 | 5/2013 | Dickinson et al. |
| 8,506,516 B2 | 8/2013 | Kassab et al. |
| 8,540,668 B2 | 9/2013 | Faul et al. |
| 8,551,032 B2 | 10/2013 | Faul et al. |
| 8,574,185 B2 | 11/2013 | Faul et al. |
| RE44,639 E | 12/2013 | Squitieri |
| 8,652,084 B2 | 2/2014 | Akingba |
| 8,727,988 B2 | 5/2014 | Flaherty et al. |
| 8,747,344 B2 | 6/2014 | Khan |
| 8,747,345 B2 | 6/2014 | Salloum |
| 8,753,366 B2 | 6/2014 | Makower et al. |
| 8,771,305 B2 | 7/2014 | Shriver |
| 8,784,474 B2 | 7/2014 | Sargent, Jr. |
| 8,808,358 B2 | 8/2014 | Khoury |
| 8,815,278 B2 | 8/2014 | Roorda |
| 8,858,490 B2 | 10/2014 | Chou et al. |
| 8,858,579 B2 | 10/2014 | Suyker et al. |
| 8,870,805 B2 | 10/2014 | Chang |
| 8,888,733 B2 | 11/2014 | Kassab |
| 8,894,681 B2 | 11/2014 | Kassab |
| 8,900,115 B2 | 12/2014 | Bolling et al. |
| 8,905,962 B2 | 12/2014 | Asano et al. |
| 8,915,934 B2 | 12/2014 | Nielsen et al. |
| 8,926,545 B2 | 1/2015 | Brenneman et al. |
| 8,945,039 B2 | 2/2015 | Kassab |
| 8,951,222 B2 | 2/2015 | Tarlian, Jr. et al. |
| 8,968,230 B2 | 3/2015 | Kassab |
| 9,108,018 B2 | 8/2015 | Dickinson et al. |
| 2001/0041930 A1 | 11/2001 | Globerman et al. |
| 2002/0052644 A1 | 5/2002 | Shaolian et al. |
| 2002/0068869 A1 | 6/2002 | Brisken et al. |
| 2002/0089262 A1 | 7/2002 | Topa et al. |
| 2002/0173784 A1 | 11/2002 | Sliwa, Jr. et al. |
| 2003/0125799 A1 | 7/2003 | Limon |
| 2003/0139802 A1 | 7/2003 | Wulfman et al. |
| 2003/0153969 A1 | 8/2003 | Dehdashtian et al. |
| 2004/0122508 A1 | 6/2004 | White et al. |
| 2004/0148005 A1 | 7/2004 | Heuser |
| 2004/0199243 A1 | 10/2004 | Yodfat |
| 2005/0004648 A1 | 1/2005 | Boekstegers |
| 2005/0165469 A1 | 7/2005 | Hogendijk |
| 2005/0192606 A1 | 9/2005 | Paul, Jr. et al. |
| 2006/0111770 A1 | 5/2006 | Pavcnik et al. |
| 2006/0122554 A1 | 6/2006 | Wilk |
| 2006/0287709 A1 | 12/2006 | Rao |
| 2007/0203515 A1 | 8/2007 | Heuser et al. |
| 2007/0265563 A1 | 11/2007 | Heuser |
| 2008/0009936 A1 | 1/2008 | Kim et al. |
| 2008/0161901 A1 | 7/2008 | Heuser et al. |
| 2008/0161904 A1 | 7/2008 | Heuser et al. |
| 2008/0177249 A1 | 7/2008 | Heuser et al. |
| 2008/0194939 A1 | 8/2008 | Dickinson et al. |
| 2009/0012429 A1 | 1/2009 | Heuser |
| 2009/0093791 A1 | 4/2009 | Heuser |
| 2009/0306755 A1 | 12/2009 | Dickinson et al. |
| 2010/0082058 A1 | 4/2010 | Kassab |
| 2010/0094391 A1 | 4/2010 | Heraty et al. |
| 2010/0241214 A1 | 9/2010 | Holzer et al. |
| 2011/0054589 A1 | 3/2011 | Bashiri et al. |
| 2011/0208109 A1 | 8/2011 | Kassab |
| 2011/0251671 A1 | 10/2011 | Heraty et al. |
| 2011/0319902 A1 | 12/2011 | Epstein |
| 2012/0046730 A1 | 2/2012 | von Oepen et al. |
| 2012/0095500 A1 | 4/2012 | Heuser |
| 2012/0116354 A1 | 5/2012 | Heuser |
| 2012/0123512 A1 | 5/2012 | Asfora et al. |
| 2012/0150092 A1 | 6/2012 | McAllister et al. |
| 2012/0179238 A1 | 7/2012 | Sarac et al. |
| 2012/0203329 A1 | 8/2012 | Heuser |
| 2012/0239137 A1 | 9/2012 | Heuser et al. |
| 2012/0271400 A1 | 10/2012 | Lyons et al. |
| 2012/0277774 A1 | 11/2012 | Guo |
| 2012/0296368 A1 | 11/2012 | Kassab et al. |
| 2013/0023813 A1 | 1/2013 | Roorda |
| 2013/0041305 A1 | 2/2013 | Tarlian, Jr. et al. |
| 2013/0041306 A1 | 2/2013 | Faul et al. |
| 2013/0060323 A1 | 3/2013 | McHugo |
| 2013/0103137 A1 | 4/2013 | Asano et al. |
| 2013/0138139 A1 | 5/2013 | Stanley |
| 2013/0144373 A1 | 6/2013 | Shahriari |
| 2013/0190676 A1 | 7/2013 | Dickinson et al. |
| 2013/0197621 A1 | 8/2013 | Ryan et al. |
| 2013/0204176 A1 | 8/2013 | Duffy et al. |
| 2013/0226067 A1 | 8/2013 | Ward et al. |
| 2013/0226285 A1 | 8/2013 | Strommer |
| 2013/0261531 A1 | 10/2013 | Gallagher et al. |
| 2013/0324901 A1 | 12/2013 | Pillai |
| 2013/0331762 A1 | 12/2013 | Kassab et al. |
| 2014/0039538 A1 | 2/2014 | Kassab et al. |
| 2014/0088623 A1 | 3/2014 | Yevzlin et al. |
| 2014/0088681 A1 | 3/2014 | Iyer et al. |

(56) References Cited

U.S. PATENT DOCUMENTS

| | | |
|---|---|---|
| 2014/0088685 A1 | 3/2014 | Yevzlin et al. |
| 2014/0100508 A1 | 4/2014 | Khan |
| 2014/0100510 A1 | 4/2014 | Yevzlin et al. |
| 2014/0142677 A1 | 5/2014 | Heuser et al. |
| 2014/0142679 A1 | 5/2014 | Motaganahalli |
| 2014/0148751 A1 | 5/2014 | Kassab et al. |
| 2014/0194910 A1 | 7/2014 | Orion et al. |
| 2014/0236274 A1 | 8/2014 | Dickinson et al. |
| 2014/0324155 A1 | 10/2014 | Paul |
| 2014/0330194 A1 | 11/2014 | Roorda |
| 2014/0343582 A1 | 11/2014 | Asfora et al. |
| 2014/0358064 A1 | 12/2014 | Dorn |
| 2014/0364882 A1 | 12/2014 | Tulleken et al. |
| 2014/0371653 A1 | 12/2014 | Criado et al. |
| 2015/0005872 A1 | 1/2015 | Theobald et al. |
| 2015/0011925 A1 | 1/2015 | Buckman, Jr. et al. |
| 2015/0025616 A1 | 1/2015 | Chang |
| 2015/0032095 A1 | 1/2015 | Heuser |
| 2015/0045728 A1 | 2/2015 | Heuser |
| 2015/0133845 A1 | 5/2015 | Dickinson et al. |
| 2015/0250500 A1 | 9/2015 | Dickinson et al. |

FOREIGN PATENT DOCUMENTS

| | | |
|---|---|---|
| WO | WO 00/45886 | 8/2000 |
| WO | WO 2005/065579 | 7/2005 |
| WO | WO 2014/137830 | 9/2014 |
| WO | WO 2014/145021 | 9/2014 |
| WO | WO 2014/162067 | 10/2014 |
| WO | WO 2014/176458 | 10/2014 |
| WO | WO 2015/017714 | 2/2015 |

OTHER PUBLICATIONS

Busato et al., "The great saphenous vein in situ for the arterialization of the venous arch of the foot", *J. Casc. Bras.*, 2010, vol. 9, No. 3, pp. 119-123.

Djoric et al., "Distal Venous Arterialization and Reperfusion Injury: Focus on Oxidative Status", *Eur. Surg. Res.*, 2012, vol. 48, pp. 200-207.

Djoric, "Early individual experience with distal venous arterialization as a lower limb salvage procedure", *Am. Surg.*, Jun. 2011, vol. 77, No. 6, pp. 726-730 (Abstract Only).

Engelke et al., "Distal Venous Arterialization for Lower Limb Salvage: Angiographic Appearances and Interventional Procedures", *Radiographics*, Sep.-Oct. 2001, vol. 21, No. 5, pp. 1239-1248.

Gasparis et al., "Distal venous arterialization for limb salvage—a case report", *Vasc. Endovascular Surg.*, Nov.-Dec. 2002, vol. 36, No. 6, pp. 469-472 (Abstract Only).

Gavrilenko et al., "Long-term results of venous blood flow arterialization of the leg and foot in patients with critical lower limb ischemia", *Angiol. Sosud. Khir.*, 2007, vol. 13, No. 2, pp. 95-103 (Abstract Only).

Houlind et al., "Early results from an angiosome-directed open surgical technique for venous arterialization in patients with critical limb ischemia", *Diabet. Foot Ankle*, Dec. 2013, vol. 17, No. 4.

Jacob et al., "Vascular surgical society of great britain and ireland: distal venous arterialization for non-reconstructable arterial disease", *Br. J. Surg.*, May 1999, vol. 86, No. 5, p. 694 (Abstract Only).

Kassab et al., "Coronary venous retroperfusion: an old concept, a new approach", *J. Appl. Physiol.*, Feb. 2008, vol. 104, pp. 1266-1272.

Keshelava et al., "Foot venous system arterialization for salvage of nonreconstructable acute ischemic limb: a case report", *J. Vasc. Nurs.*, Mar. 2009, vol. 27, No. 1, pp. 13-16 (Abstract Only).

Kopelman et al., "Prevention of limb loss in critical ischaemia by arterialization of the superficial venous system: an experimental study in dogs", *Cardiovasc. Surg.*, Aug. 1998, vol. 6, No. 4, pp. 384-388 (Abstract Only).

Lengua et al., "Arterialization of the distal veins of the foot for limb salvage in arteritis—Techniques and results", *Ann. Chir.*, Sep. 2001, vol. 126, No. 7, pp. 629-638 (Abstract Only).

Lu et al., "Meta-analysis of the Clinical Effectiveness of Venous Arterialization for Salvage of Critically Ischaemic Limbs", *Eur. J. Vasc. Endovasc. Surg.*, May 2006, vol. 31, pp. 493-499.

Matarrese et al., "Revascularization of the ischemic hand with arterialization of the venous system", *J. Hand. Surg. Am.*, Dec. 2011, vol. 36, No. 12, pp. 2047-2051 (Abstract Only).

Miasnik et al., "Scintigraphic evaluation of the efficacy of nonstandard methods of treating critical ischemia of the lower limbs", *Khirurgiia (Mosk)*, 2002, vol. 6, pp. 48-51 (Abstract Only).

Mutirangura et al., "Pedal bypass with deep venous arterialization: the therapeutic option in critical limb ischemia and unreconstructable distal arteries", *Vascular*, Dec. 2011, vol. 19, No. 6, pp. 313-319.

Nguyen et al., "Treatment of hand ischemia with arterialization of the venous system of the hand: report of three cases", *Ann. Chir. Plast. Esthet.*, Jun. 2011, vol. 56, No. 3, pp. 200-206 (Abstract Only).

Pederson, "Revascularization of the chronically ischemic hand", *Hand Clin*, Nov. 1999, vol. 15, No. 4, pp. 629-642 (Abstract Only).

Pokrovsky et al., "Arterialization of the hand venous system in patients with critical ischemia and thrombangiitis obliterans", *Angiol. Sosud. Khir.*, 2007, vol. 13, No. 2, pp. 105-111 (Abstract Only).

Rowe et al., "Initial experience with dorsal venous arch arterialization for limb salvage", *Ann. Vasc. Surg.*, Feb.-Mar. 2002, vol. 16, No. 2, pp. 187-192 (Abstract Only).

Sangiorgi et al, "The Cutaneous Microvascular Architecture of Human Diabetic Toe Studied by Corrosion Casting and Scanning Electron Microscopy Analysis", *Anat. Rec.*, Oct. 2010, vol. 293, pp. 1639-1645.

Sasajima et al., "Combined distal venous arterialization and free flap for patients with extensive tissue loss", *Ann. Vasc. Surg.*, Apr. 2010, vol. 24, No. 3, pp. 373-381 (Abstract Only).

Schreve et al., "Comparative study of venous arterialization and pedal bypass in a patient cohort with critical limb ischemia", *Ann. Vasc. Surg.*, Jul. 2014; vol. 28, No. 5, pp. 1123-1127 (Abstract Only).

Sheil, "Treatment of critical ischaemia of the lower limb by venous arterialization : an interim report", *Br. J. Surg.*, Mar. 1977, vol. 64, No. 3, pp. 197-199 (Abstract Only).

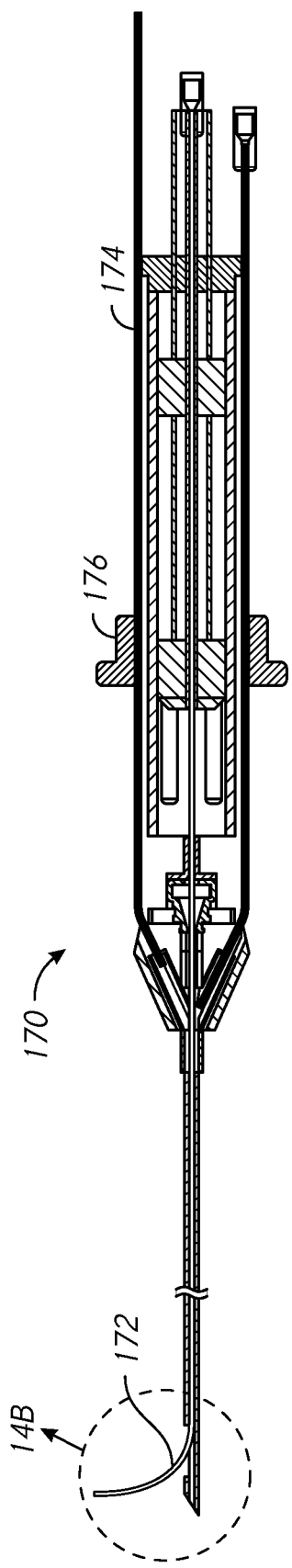
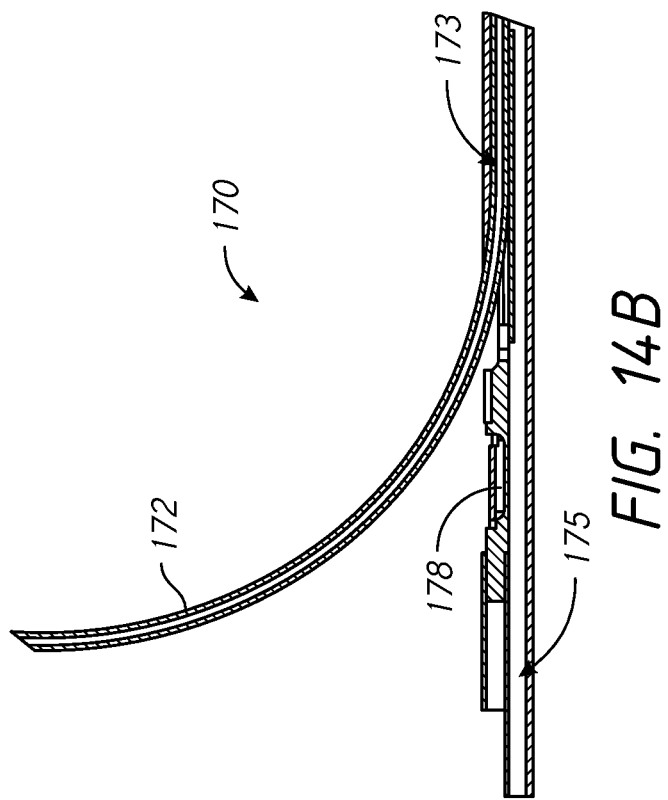
FIG. 14A
FIG. 14B

METHODS AND SYSTEMS FOR PROVIDING OR MAINTAINING FLUID FLOW THROUGH BODY PASSAGES

INCORPORATION BY REFERENCE

This application claims the benefit under 35 U.S.C. §120 and 35 U.S.C. §365(c) as a continuation of International Application No. PCT/US2011/026501 designating the United States, with an international filing date of Feb. 28, 2011, which claims the benefit under 35 U.S.C. §119(e) of U.S. Provisional Patent App. No. 61/901,753, filed on Nov. 8, 2013, and International Application No. PCT/US2011/026501 is a continuation-in-part of U.S. patent application Ser. No. 13/791,185, filed on Mar. 8, 2013, each of which is hereby incorporated by reference in its entirety. U.S. patent application Ser. No. 11/662,128, filed on Jan. 3, 2008, U.S. patent application Ser. No. 14/141,913, filed on Dec. 27, 2013, and U.S. patent application Ser. No. 12/297,498, filed on Feb. 25, 2009 as a national phase of PCT/GB2007/001430, filed Apr. 20, 2007, and issued as U.S. Pat. No. 8,439,963 on May 14, 2013, are hereby incorporated by reference in their entirety.

BACKGROUND

1. Field

The present application relates to methods and systems for use in percutaneous interventional surgery. In particular, the present application relates to methods and systems for providing or maintaining fluid flow through body passages such as heart cavities and blood vessels.

2. Description of the Related Art

Minimally invasive percutaneous surgery, or "key-hole" surgery, is a surgical technique in which surgical devices are inserted into a patient's body cavity through a small aperture cut in the skin. This form of surgery has become increasingly popular as it allows patients to endure less surgical discomfort while retaining the benefits of conventional surgery. Patients treated by such techniques are exposed to lower levels of discomfort, need for general anesthesia, trauma, and risk of infection, and their recovery times can be significantly reduced compared to conventional surgical procedures.

Key-hole surgery can be used, for example, for laparoscopic surgery and to treat cardiovascular diseases. In treating cardiovascular diseases, balloon angioplasty, in which a balloon catheter is inserted into an artery usually near the patient's groin and guided to the patient's heart where a balloon at a distal portion of the catheter is inflated to widen or dilate an occluded vessel to help restore blood flow to the cardiac tissue, may be used to treat a partially occluded coronary artery as an alternative to open heart surgery. A tubular supporting device (e.g., stent) may be deployed at the site of the blockage to prevent future occlusion (restenosis) or collapse of the blood vessel. The stent may, for example, be an expandable metal mesh tube carried on the balloon of the balloon catheter, or be self-expanding. The balloon-expandable stent expands when the balloon is inflated, so that the stent pushes against the wall of the blood vessel. The stent is arranged to retain its expanded shape when it reaches its expanded position, for example by plastic deformation or by means of a mechanical locking mechanism, so as to form a resilient scaffold or support in the blood vessel. The support structure (e.g., stent) supports and dilates the wall of the blood vessel to maintain a pathway for blood to flow through the vessel. Self-expanding stents are also available, which are held in a collapsed state by a suitably adapted catheter for transport through the artery and which adopt an expanded state when deployed at the site of the blockage. The catheter may, for example, include a retaining sleeve which retains the stent in a compressed or unexpanded state. Upon removal or withdrawal of the sleeve from the stent, the stent expands to support and dilate the wall of the blood vessel.

Balloon angioplasty is not always a suitable measure, for example in acute cases and in cases where a coronary artery is completely occluded. In these instances, the typical treatment is to employ coronary bypass. Coronary bypass surgery is an open-chest or open-heart procedure, and typically involves grafting a piece of healthy blood vessel onto the coronary artery so as to bypass the blockage and restore blood flow to the coronary tissue. The healthy blood vessel is usually a vein harvested from the patient's leg or arm during the course of the bypass operation. To perform the procedure, the patient's heart must be exposed by opening the chest, separating the breastbone, and cutting the pericardium surrounding the heart, resulting in significant surgical trauma.

Conventional coronary bypass surgery is not always an option. Certain patients are unsuitable as candidates for conventional coronary bypass surgery due low expectation of recovery or high risk from the significant trauma due to surgery, high risk of infection, absence of healthy vessels to use as bypass grafts, significant co-morbidities, and expected long and complicated recovery time associated with open-chest surgery. For example, factors such as diabetes, age, obesity, and smoking may exclude a proportion of candidate patients who are in genuine need of such treatment.

SUMMARY

The present application provides methods and systems for overcoming certain deficiencies and/or improving percutaneous methods and systems. For example, according to several embodiments, the methods and systems described herein can improve targeting and localization of therapy administration, which may advantageously provide treatment via percutaneous techniques to patients unsuitable for more invasive surgery. Certain embodiments described herein can provide fluid flow in passages such as coronary and/or peripheral blood vessels by creating a bypass using minimally invasive percutaneous surgical techniques.

In some implementations, a method of diverting fluid flow from a first passage to a second passage comprises deploying a device in a third passage between the first passage and the second passage. The device comprises a first end portion, a second portion, an intermediate portion, and a graft material. The first end portion has a first end diameter. The second end portion has a second end diameter larger than the first end diameter. The intermediate portion is between the first end portion and the second end portion. The intermediate portion tapers between the first end portion and the second end portion. The graft material is coupled to at least the intermediate portion. The method further comprises expanding the first end portion against sidewalls of the first passage and expanding the second end portion against sidewalls of the second passage.

The first passage may be an artery and the second passage may be a vein. The first passage may be a coronary artery and the second passage may be a coronary vein. The method may further comprise dilating the third passage. The first passage may be a peripheral artery and the second passage may be a peripheral vein. The method may further comprise dilating the third passage. Dilating the third passage may comprise expanding the intermediate portion. The first passage may be substantially parallel to the second passage. The intermediate portion may be conformable to an "S" shape. Expanding the first end portion and the second end portion may comprise allowing self-expansion of the first end portion and the second end portion. Expanding the first end portion and the second end portion may comprise balloon expanding at least one of the first end portion and the second end portion. Expanding one of the first end portion and the second end portion may comprise allowing self-expansion of the one of the first end portion and the second end portion and expanding the other of the first end portion and the second end portion may comprise balloon expanding the other of the first end portion and the second end portion. The method may further comprise expanding the intermediate portion.

In some implementations, a device comprises a first end portion, a second end portion, an intermediate portion, and a graft material. The first end portion has a first end diameter. The second end portion has a second end diameter smaller than the first end diameter. The intermediate portion is between the first end portion and the second end portion. The intermediate portion tapers between the first end portion and the second end portion. The graft material is coupled to at least the intermediate portion.

At least one of the first end portion and the second end portion may be substantially cylindrical. The first end portion may be substantially cylindrical and the second end portion may be substantially cylindrical. The first end portion may taper between the first end diameter and the intermediate portion or the second end portion may taper between the second end diameter and the intermediate portion. The first end portion may taper between the first end diameter and the intermediate portion and the second end portion may taper between the second end diameter and the intermediate portion. The first end portion may comprise a first type of material, the second end portion may comprise a second type of material, and the intermediate portion may comprise a third type of material. The first type of material may comprise a first cut material, the second type of material may comprise a second cut material, and the third type of material may comprise filaments. The first cut material may comprise a chromium cobalt alloy, the second cut material may comprise nitinol, and the filaments may comprise nitinol. The first type of material may comprise a cut material, the second type of material may comprise the cut material, and the third type of material may comprise filaments. The cut material may comprise nitinol and the filaments may comprise nitinol. At least one of the first end portion, the second end portion, the intermediate portion, and the graft material may comprise a bioabsorbable material. At least some of the graft material may be outside the intermediate portion. At least some of the graft material may be inside the intermediate portion. At least some of the graft material may be embedded within the intermediate portion. The device may be capable of maintaining, or configured to maintain, fluid flow between a first passage in which the first end portion is anchored and a second passage in which the second end portion is anchored. The first passage may be substantially parallel to the second passage. The intermediate portion may be conformable to an "S" shape.

In some implementations, a device comprises a first end portion, a second end portion, an intermediate portion, and a graft material. The first end portion comprises a first material. The second end portion comprises a second material different than the first material. The intermediate portion is between the first end portion and the second end portion. The graft material is coupled to at least the intermediate portion.

The first material may comprise nitinol and the second material may comprise chromium cobalt. The first material may comprise nitinol and the second material may comprise stainless steel. The first end portion may comprise cut struts and the second end portion may comprise filaments. The first end portion may comprise cut struts and the second end portion may comprise cut struts. The first material may comprise an alloy and the first end portion may comprise struts or filaments having a first thickness, and the second material may comprise the alloy and the second end portion may comprise struts or filaments having a second thickness different than the first thickness. The intermediate portion may comprise a third material. The third material may comprise nitinol. The intermediate portion may comprise filaments. The intermediate portion may comprise cut struts. At least one of the first end portion and the second end portion may be substantially cylindrical. At least one of the first end portion, the second end portion, the intermediate portion, and the graft material may comprise a bioabsorbable material. At least some of the graft material may be outside the intermediate portion. At least some of the graft material may be inside the intermediate portion. At least some of the graft material may be embedded within the intermediate portion. The graft material may be coupled to at least one of the first end portion and the second end portion. The device may be capable of maintaining, or configured to maintain, fluid flow between a first passage in which the first end portion is anchored and a second passage in which the second end portion is anchored. The first passage may be substantially parallel to the second passage. The intermediate portion may be conformable to an "S" shape.

In some implementations, a device comprises a support structure and a graft material. The support structure comprises a first end portion, a second end portion, and an intermediate portion between the first end portion and the second end portion. At least one of the first end portion, the second end portion, and the intermediate portion comprise cut struts and at least one of the first end portion, the second end portion, and the intermediate portion comprise filaments. The graft material is coupled to at least the intermediate portion.

The first end portion and the second end portion comprise cut struts and the intermediate portion may comprise filaments. At least some of the graft material may be outside the intermediate portion. At least some of the graft material may be inside the intermediate portion. At least some of the graft material may be embedded within the intermediate portion. The graft material may be coupled to at least one of the first end portion and the second end portion. The device may be capable of maintaining, or configured to maintain, fluid flow between a first passage in which the first end portion is anchored and a second passage in which the second end portion is anchored. The first passage may be substantially parallel to the second passage. The intermediate portion may be conformable to an "S" shape.

The device may have a diameter between about 1 mm and about 12 mm (e.g., between 2 mm and 6 mm). The device may have a diameter between about 1 mm and about 10 mm (e.g., between 4 mm and 8 mm). The device may have a diameter between about 6 mm and about 25 mm (e.g., between 12 mm and 15 mm). The device may have a diameter between about 20 mm and about 50 mm (e.g., between 35 mm and 40 mm). The device may have a length between about 25 mm and about 150 mm (e.g., between 70 mm and 110 mm). The device may include filaments having a diameter between about 0.001 inches and about 0.01 inches (e.g., between 0.003 inches and 0.006 inches). The device may include struts having a diameter between about 0.001 inches and about 0.01 inches (e.g., between 0.003 inches and 0.006 inches).

In some embodiments, a device for providing or maintaining fluid flow through at least one passage in a human or animal body includes two end portions for anchoring the device in position and an intermediate portion that allows movement of the end portions relative to each another. The end portions and the intermediate portion together define a pathway for fluid flow through the device.

By allowing the two end portions to move relative to each other, the device can respond to movement of the passage or passages in which the device is used. The intermediate portion may be flexible to allow relative movement of the end portions. In some embodiments, the device has varying or differential flexibility along the length of the device or along a length of a portion of the device. Device flexibility can reduce the likelihood of device failure due to fatigue, for example because the magnitude of stresses within the intermediate portion may be relatively low in comparison to stresses on a support structure (e.g., stent) with uniform flexibility along its entire length.

The device may be configured to provide or maintain fluid flow through a single passageway, for example an occluded blood vessel. The intermediate portion may be capable of maintaining, or configured to maintain, fluid flow between proximal and distal portions of the occluded blood vessel. The intermediate portion can pass through a further passage, for example outside the blood vessel, extending between the proximal and distal portions of the blood vessel. The device may be configured for use as a bypass between proximal and distal portions of a single blood vessel, for example an artery or a vein.

The device may be configured to provide fluid flow from an occluded blood passage to another passage. The passages can be interconnected by the intermediate portion passing through a further passage extending between the two passages. The device may be configured for use as a shunt between two passages, for example between an artery and a vein.

In embodiments in which the end portions can move relative to one another by virtue of the intermediate portion, the device may be suitable for use in applications where the end portions are anchored in separate passages that move relative to one another. A pathway for fluid communication to be maintained through the device irrespective of the relative movement of the end portions, and the likelihood of fatigue failure of the device due to cyclic movement of the end portions may be low in comparison to a support structure (e.g., stent) lacking such an intermediate portion.

One or both of the end portions may be diametrically expandable to anchor the device in position. An expanded end portion may, for example, be expandable to meet with and press against the inner sidewalls of a passage to inhibit or prevent substantial sliding or rotation of the end portion within the passage, and/or to dilate the passage. The intermediate portion may be diametrically expandable, for example to dilate the fluid flow pathway.

The device may be in the form of a tube defining a lumen configured to act as a fluid flow pathway. In some embodiments, the tube may be fluid-tight, so as to confine the fluid flow within the lumen of the tube. The tube may include, but is not limited to, a polymeric material, for example a biocompatible polymer such as polytetrafluoroethylene (PTFE) or polyurethane such as polycarbonate aromatic biodurable thermoplastic polyurethane elastomer (e.g., ChronoFlex C® 80A and 55D medical grade, available from AdvanSource Biomaterials of Wilmington, Mass.).

The device may include a supporting structure that supports the end portions. The supporting structure may support the intermediate portion, in which case the supporting structure may be flexible within the intermediate portion to allow movement of the end portions relative to each other.

When a supporting structure is provided, the supporting structure or a portion thereof may be embedded within a wall of the tube. Alternatively or in addition, the structure or a portion of the structure may be located on the outside of the tube or within the lumen of the tube.

The supporting structure may include at least one mesh. For example, a single mesh may extend along the entire length of the device. In another example, each end of the device includes a mesh, in which case the meshes may stop short of the intermediate portion or may extend into the intermediate portion. When a mesh is present in the intermediate portion, the mesh may have a higher density or smaller window size (e.g., a smaller spacing between filaments and/or struts of the mesh) in the end portions than in the intermediate portion so that the device is relatively more flexible in the intermediate portion than in the end portions. The device may be relatively more flexible in the intermediate portion than in the end portions by way of absence of a mesh, or even when including a mesh with substantially uniform or uniform density or window size (e.g., due to factors other than mesh density or window size), or by including a mesh having a non-uniform density.

At least one mesh may include biocompatible metal wire. For example, the metal wire may be stainless steel. Alternatively, or in addition, at least one mesh may include a shape memory material, for example nitinol and/or chromium cobalt. When a shape memory material is used, at least a portion of the device may be self-expanding.

One or both end portions may include anchoring protuberances or barbs capable of and/or configured to dig into or grasp the inside sidewalls of a passage, for example to prevent or reduce slippage or other movement of the or each end portion relative to the passage.

The two end portions may have different diameters, so that the device can be made to fit securely within a passage having variable diameter, or with one end portion in a first passage and the other end portion in a second passage, when the passages have different diameters. The device can be configured for a particular application and/or for a particular patient.

In some embodiments, a method of diverting fluid flow from a first passage to a second passage (e.g., adjacent to the first passage) includes forming a third passage between the first and second passages, providing a device having two end portions and an intermediate portion, deforming the intermediate portion of the device to permit insertion of the device in the passages, and expanding the end portions against the walls of the first and second passages so as to anchor the device in the passages. The intermediate portion of the device may be flexed to permit insertion of the device in the passages. The two end portions and the intermediate portion may be configured to maintain or provide fluid flow through the device.

One or more end portions of the device may be expanded by a balloon catheter. Alternatively, or in addition, at least one end portion may be self-expanding, in which case the method may include providing the device in a retaining sleeve, and removing the retaining sleeve to enable the at least one end portion to expand.

The method may further include expanding the intermediate portion to dilate the third passage, thereby forming a larger pathway for fluid flow from the first passage to the second passage.

The methods described herein may be used in many surgical procedures, and can be performed by minimally invasive (key-hole) techniques. The methods may be particularly suitable for the treatment of coronary heart disease, for example by providing a shunt or bypass to divert arterial blood from an occluded coronary artery to a coronary vein (e.g., adjacent to the coronary artery) and/or by traversing an occlusion in a coronary artery by exiting the artery proximal to the occlusion, extending through subintimal tissue, external tissue, and/or a portion of a proximate vessel, and reentering the coronary artery distal to the occlusion, for peripheral vascular disease such as critical limb ischemia, for example by providing a shunt or bypass to divert arterial blood from an occluded peripheral artery to a peripheral vein and/or by traversing an occlusion in a peripheral vessel by exiting the vessel proximal to the occlusion, extending through subintimal tissue, external tissue, and/or a portion of a proximate vessel, and reentering the vessel distal to the occlusion, and/or for non-occluded vessels, for example by creating a shunt between a healthy artery and a healthy vein that can be used for dialysis access.

In some embodiments, a method of treating coronary heart disease includes diverting arterial blood from a coronary artery to a coronary vein by the methods described herein. In some embodiments, a method of treating critical limb ischemia includes diverting arterial blood from a peripheral artery to a peripheral vein by the methods described herein.

In some embodiments, a method of accessing a target vein comprises inserting a needle into the target vein and inserting a guidewire into the target vein through the needle.

The target vein may be the proximal tibial vein. The method may further comprise advancing a catheter over the second guidewire. The guidewire may comprise an ultrasound receiving transducer. The method may further comprise advancing the guidewire in a direction of flow of blood in the target vein. The method may further comprise inserting an introducer sheath into a second vein upstream of the target vein. The method may further comprise inserting a second guidewire into the second vein. The second guidewire may comprise an ultrasound receiving transducer. The method may further comprise at least one of snaring the guidewire with the second guidewire or a snare and snaring the second guidewire with the guidewire, and pulling the second guidewire in a direction opposite of blood flow into the target vein. Snaring the guidewire may comprise injecting contrast and visualizing using fluoroscopy. The method may further comprise advancing a catheter over the second guidewire. The catheter may comprise an ultrasound receiving transducer.

In some embodiments, a device for making valves of a vessel incompetent comprises a proximal portion, a distal portion and a longitudinal axis between the proximal portion and the distal portion. The distal portion may comprise at least one blade. The at least one blade may have a retracted position in which the at least one blade is substantially parallel to the longitudinal axis and an expanded position in which the at least one blade is substantially non-parallel to the longitudinal axis. The at least one blade may comprise a sharp surface facing distally and configured to at least partially ablate a valve during distal advancement of the device.

The at least one blade may comprise a plurality of blades. The plurality of blades may comprise three blades. The three blades may be circumferentially spaced by about 120 degrees. The proximal portion may comprise a handle configured to operate the at least one blade between the retracted position and the expanded position. The at least one blade may comprise shape memory material. The handle may be configured to allow the at least one blade to self-expand from the retracted position to the expanded position. The handle may be configured to longitudinally compress and radially expand the at least one blade from the retracted position to the expanded position. A kit may comprise the device and a vessel expansion device. The vessel expansion device may comprise at least one of a tourniquet, a balloon, and a LeMaitre device.

In some embodiments, a method of making valves of a vessel incompetent comprises advancing a reverse valvulotome in a direction opposite native fluid flow in the vessel. During advancing the reverse valvulotome, at least one blade of the reverse valvulotome at least partially ablates the valves.

The reverse valvulotome may comprise at least one blade. The at least one blade may have a retracted position in which the at least one blade is substantially parallel to the longitudinal axis and an expanded position in which the at least one blade is substantially non-parallel to the longitudinal axis. The at least one blade may comprise a sharp surface facing distally and configured to at least partially ablate a valve during distal advancement of the device. The at least one blade may comprise a plurality of blades. The plurality of blades may comprise three blades. The three blades may be circumferentially spaced by about 120 degrees. The method may further comprise expanding the vessel and the valves in the vessel. Expanding the vessel and the valves in the vessel may comprise applying a tourniquet to a body part comprising the vessel. Expanding the vessel and the valves in the vessel may comprise expanding a balloon in the vessel. Expanding the vessel and the valves in the vessel may comprise expanding a LeMaitre device in the vessel.

In some embodiments, a method of effecting retroperfusion in a first vessel comprises forming a fistula between the first vessel and a second vessel and making valves in the first vessel incompetent.

The first vessel may comprise a vein and the second vessel may comprise an artery. Making the valves in the first vessel incompetent may comprise inflating a balloon to a pressure greater than about 10 atmospheres (atm) (approx. 1,013 kilopascals (kPa)) across the valves. Making the valves in the first vessel incompetent may comprise deploying at least one stent across the valves. Making the valves in the first vessel incompetent may comprise inflating a cutting balloon. Making the valves in the first vessel incompetent may comprise atherectomy. Making the valves in the first vessel incompetent may comprise ablating the valves with ultrasound. Making the valves in the first vessel incompetent may comprise ablating the valves with a laser. Making the valves in the first vessel incompetent may comprise ablating the valves with radio frequency. Making the valves in the first vessel incompetent may comprise heating the valves. Making the valves in the first vessel incompetent may comprise at least one of advancing and retracting a catheter comprising a traumatic tip. Making the valves in the first vessel incompetent may comprise expanding the vessel and the valves in the vessel. Expanding the vessel and the valves in the vessel may comprise applying a tourniquet to a body part comprising the vessel. Expanding the vessel and the valves in the vessel may comprise expanding a balloon in the vessel. Expanding the vessel and the valves in the vessel may comprise expanding a LeMaitre device in the vessel. Making the valves in the first vessel incompetent may comprise expanding the first vessel and the valves in the first vessel, advancing a guidewire through the vessel, and tracking a device over the guidewire. Expanding the first vessel and the valves in the first vessel may comprise applying a tourniquet to a body part comprising the first vessel. Expanding the first vessel and the valves in the first vessel may comprise expanding a balloon in the first vessel. Expanding the first vessel and the valves in the first vessel may comprise expanding a LeMaitre device in the vessel.

Forming the fistula between the artery and the vein may comprise accessing the vein. Accessing the vein may comprise inserting a needle into the vein and inserting a guidewire into the vein through the needle. The vein may be the proximal tibial vein. The method may further comprise advancing a catheter over the second guidewire. The guidewire may comprise an ultrasound receiving transducer. The method may further comprise advancing the guidewire in a direction of flow of blood in the vein. The method may further comprise inserting an introducer sheath into a second vein upstream of the vein. The method may further comprise inserting a second guidewire into the second vein. The second guidewire may comprise an ultrasound receiving transducer. The method may further comprise at least one of snaring the guidewire with the second guidewire or a snare and snaring the second guidewire with the guidewire, and pulling the second guidewire in a direction opposite of blood flow into the vein. Snaring the guidewire may comprise injecting contrast and visualizing using fluoroscopy. The method may further comprise advancing a catheter over the second guidewire. The catheter may comprise an ultrasound receiving transducer. Forming the fistula between the first vessel and the second vessel may comprise inserting a launching catheter into the second vessel, inserting a target catheter into the first vessel, emitting an ultrasound signal from the ultrasound emitting transducer, during emitting the ultrasound signal and until the ultrasound signal is received by the ultrasound receiving transducer, at least one of rotating the launching catheter and longitudinally moving the launching catheter, and after the ultrasound signal is received by the ultrasound receiving transducer, extending the needle from the launching catheter. The launching catheter may comprise an ultrasound emitting transducer and a needle configured to radially extend from the launching catheter. The target catheter may comprise an ultrasound receiving transducer. Extending the needle may comprise exiting the second vessel, traversing interstitial tissue between the second vessel and the first vessel, and entering the first vessel. The ultrasound emitting transducer may comprise a directional transducer. The needle may be configured to radially extend from the launching catheter along a path aligned with a path of the directional transducer. The ultrasound receiving transducer may comprise an omnidirectional transducer. Forming the fistula between the first vessel and the second vessel may comprise identifying signal alignment peaks on a display device. Identifying the signal alignment peaks on the display device may comprise identifying a color indicative that the signal alignment peaks are greater than a threshold value. Forming the fistula between the first vessel and the second vessel may comprise identifying an audible signal indicative that signal alignment is greater than a threshold value. Forming the fistula between the first vessel and the second vessel may comprise inserting a launching catheter into the second vessel. The launching catheter comprises a needle configured to radially extend from the launching catheter. Forming the fistula between the first vessel and the second vessel may further comprise inserting a target catheter comprising a target device into the first vessel, expanding the target device, and extending the needle from the launching catheter. Extending the needle may comprise exiting the second vessel, traversing interstitial tissue between the second vessel and the first vessel, and entering the first vessel, wherein, during entering the first vessel, the needle punctures the target device. The target device may comprise a balloon. The balloon may comprise a polymer and a mesh at least partially embedded in the polymer. Expanding the target device may comprise inflating the balloon. The target device may comprise a mesh. Expanding the target device may comprise distally advancing a proximal portion of the mesh. Expanding the target device may comprise proximally retracting a distal portion of the mesh. Expanding the target device may comprise allowing the mesh to self-expand. Forming the fistula between the first vessel and the second vessel may comprise inserting a crossing guidewire through the fistula. Forming the fistula between the first vessel and the second vessel may comprise dilating the fistula. Dilating the fistula may comprise inflating a balloon. Forming the fistula between the first vessel and the second vessel may comprise deploying a prosthesis. After deploying the prosthesis, at least a first portion of the prosthesis may be in the first vessel and at least a second portion of the prosthesis may be in the second vessel. Deploying the prosthesis may comprise actuating a trigger handle. The prosthesis may comprise a stent graft. The stent graft may comprise a longitudinal portion having a frustoconical longitudinal cross-section. Deploying the prosthesis may comprise allowing the prosthesis to self-expand. The method may further comprise expanding the prosthesis with a balloon. The method may further comprise applying a radiopaque clip to skin outside the skin proximate to a position of the fistula. The method may further comprise determining a distance between the first vessel and the second vessel.

In some embodiments, a target catheter for forming a fistula comprises a proximal portion and a distal portion. The distal portion may comprise an expandable member and an ultrasound receiving transducer proximate to the expandable member.

The expandable member may comprise a balloon. The expandable member may comprise a mesh. The ultrasound receiving transducer may comprise an omnidirectional transducer. The ultrasound receiving transducer may be radially inward of the expandable member. The catheter may further comprise an inflation lumen in fluid communication with the expandable member and the proximal portion. The catheter may further comprise a pressure sensor configured to detect puncturing of the expandable member.

In some embodiments, a kit for effecting retroperfusion in a vein comprises a valve disabling device and at least one of the group consisting of a launching catheter, a target catheter, a prosthesis delivery system.

The valve disabling device may comprise at least one of a reverse valvulotome, a balloon, and a stent. The launching catheter may comprise a needle configured to radially extend from the launching catheter. The launching catheter may comprise an ultrasound emitting transducer. The kit may further comprise a guidewire. The launching catheter may be configured to be tracked over the guidewire. The kit may further comprise an artery introducer sheath. The kit may further comprise a second guidewire. The target catheter may be configured to be tracked over the second guidewire. The target catheter may comprise an ultrasound receiving transducer. The ultrasound emitting transducer may comprise an omnidirectional transducer. The target catheter may comprise a balloon. The kit may further comprise a third guidewire. The second guidewire may be configured to snare the third guidewire. The third guidewire may be configured to snare the second guidewire. The kit may further comprise a vein introducer sheath. The kit may further comprise a vein access needle. The kit may further comprise an access guidewire. The kit may further comprise at least one balloon. The at least one balloon may be configured to pre-dilate a fistula. The at least one balloon may be configured to expand a vessel diameter. The at least one balloon may be configured to make a valve incompetent. The at least one balloon may be configured to apply a pressure greater than about 10 atm (approx.

1,013 kPa). The kit may further comprise a prosthesis delivery system. The kit may further comprise a device configured to stretch a vessel. The device configured to stretch the vessel may comprise at least one of a tourniquet, a balloon, and a LeMaitre device. The kit may further comprise a computing device configured to be communicatively coupled to at least one of the launching catheter and the target catheter. The computing device may comprise a laptop computer. The computing device may comprise a tablet computer. The computing device may comprise a smartphone. The computing device may comprise a display device configured to display information about relative positions of the launching catheter and the target catheter. The computing device may comprise a speaker configured to emit information about relative positions of the launching catheter and the target catheter.

In some embodiments, a method of marking a fistula point comprises applying a marker to skin proximate to a location of the fistula. The marker may be visible under fluoroscopy.

The marker may comprise a clip. The marker may comprise radiopaque material. The fistula may be between a first vessel and a second vessel. Applying the marker may be before deploying a prosthesis in the fistula.

In some embodiments, a method of making valves of a vessel incompetent comprises providing a reverse valvulotome. Upon advancing the reverse valvulotome in a direction opposite native fluid flow in the vessel, at least one blade of the reverse valvulotome at least partially ablates the valves.

In some embodiments, a method of effecting retroperfusion in a first vessel comprises providing a first system configured to create a fistula between the first vessel and a second vessel and providing a second device configured to make valves in the first vessel incompetent.

In some embodiments, a method of forming a fistula in a first vessel comprises inserting a launching catheter into a second vessel. The launching catheter comprises an ultrasound emitting transducer and a needle configured to radially extend from the launching catheter. The method may further comprise inserting a target catheter comprising an ultrasound receiving transducer into the first vessel, emitting an ultrasound signal from the ultrasound emitting transducer, and during emitting the ultrasound signal and until the ultrasound signal may be received by the ultrasound receiving transducer, at least one of rotating the launching catheter and longitudinally moving the launching catheter. The method may further comprise, after the ultrasound signal may be received by the ultrasound receiving transducer, extending the needle from the launching catheter. Extending the needle may comprise exiting the second vessel traversing interstitial tissue between the second vessel and the first vessel, and entering the first vessel.

The ultrasound emitting transducer may comprise a directional transducer. The needle may be configured to radially extend from the launching catheter along a path aligned with a path of the directional transducer. The ultrasound receiving transducer may comprise an omnidirectional transducer.

In some embodiments, a kit for effecting retroperfusion in a vein comprises a launching catheter, a target catheter, and a prosthesis delivery system.

The launching catheter may comprise a needle configured to radially extend from the launching catheter. The launching catheter may comprise an ultrasound emitting transducer. The target catheter may comprise an ultrasound receiving transducer. The ultrasound emitting transducer may comprise an omnidirectional transducer.

The methods summarized above and set forth in further detail below describe certain actions taken by a practitioner; however, it should be understood that they can also include the instruction of those actions by another party. Thus, actions such as "making valves in the first vessel incompetent" include "instructing making valves in the first vessel incompetent."

For purposes of summarizing the invention and the advantages that may be achieved, certain objects and advantages are described herein. Not necessarily all such objects or advantages need to be achieved in accordance with any particular embodiment. In some embodiments, the invention may be embodied or carried out in a manner that can achieve or optimize one advantage or a group of advantages without necessarily achieving other objects or advantages.

All of these embodiments are intended to be within the scope of the invention herein disclosed. These and other embodiments will be apparent from the following detailed description having reference to the attached figures, the invention not being limited to any particular disclosed embodiment(s). Optional and/or preferred features described with reference to some embodiments may be combined with and incorporated into other embodiments. All references cited herein, including patents and patent applications, are incorporated by reference in their entirety.

BRIEF DESCRIPTION OF THE DRAWINGS

These and other features, aspects, and advantages of the present disclosure are described with reference to the drawings of certain embodiments, which are intended to illustrate certain embodiments and not to limit the invention, in which like reference numerals are used for like features, and in which:

FIG. 14A is a schematic side cross-sectional view of an example embodiment of an ultrasound launching catheter.

FIG. 14B is an expanded schematic side cross-sectional view of a distal portion of the ultrasound launching catheter of FIG. 14A within the circle 14B.

DETAILED DESCRIPTION

Although certain embodiments and examples are described below, the invention extends beyond the specifically disclosed embodiments and/or uses and obvious modifications and equivalents thereof. The scope of the invention herein disclosed should not be limited by any particular embodiment(s) described below.

Minimally invasive surgery could provide a means for treating a broader range of patients, including those currently excluded from standard surgical techniques. One such procedure is percutaneous in situ coronary venous arterialization (PICVA), which is a catheter-based coronary bypass procedure in which the occlusion in the diseased artery is "bypassed" by creation of a channel between the coronary artery and the adjacent coronary vein. In this way, the arterial blood is diverted into the venous system and can perfuse the cardiac tissue in a retrograde manner (retroperfusion) and restores blood supply to ischemic tissue. Some example devices and methods for performing procedures like PICVA are described in PCT Pub. No. WO 99/049793 and U.S. Patent Pub. No. 2004/0133225, which are hereby incorporated by reference in their entirety.

Successfully performing a minimally invasive procedure of diverting blood flow from the coronary artery to the adjacent vein heretofore has had a low success rate, most often due to inability to properly target the vein from the artery. Without the proper systems and methods, such procedures (e.g., attempting to target the vein by combination of X-ray fluoroscopy and an imaging ultrasound probe located on the distal tip of the catheter e.g., as described in U.S. Patent Pub. No. 2004/0133225) are often doomed to failure before even starting. Indeed, such an arrangement can be difficult to navigate, and localization of the adjacent vein can require considerable skill on the part of the clinician. Improvements in the systems and methods for targeting, such as those using the catheters described herein, can enable procedures such as PICVA and transvascular surgery in general. Without such improvements, such percutaneous techniques will remain peripheral to conventional surgical open-heart and other types of bypass operations.

The present application, according to several embodiments, describes methods and systems usable in minimally invasive surgical procedures, which can reduce performance of conventional surgery to treat conditions such as coronary heart disease and critical limb ischemia. For example, patients who might otherwise be unable to receive surgery such as coronary bypass surgery or peripheral arterial bypass surgery can be treated, and the amount of surgical trauma, the risk of infection, and/or the time to recovery may be reduced or significantly reduced in comparison to conventional surgery.

Figure 1:
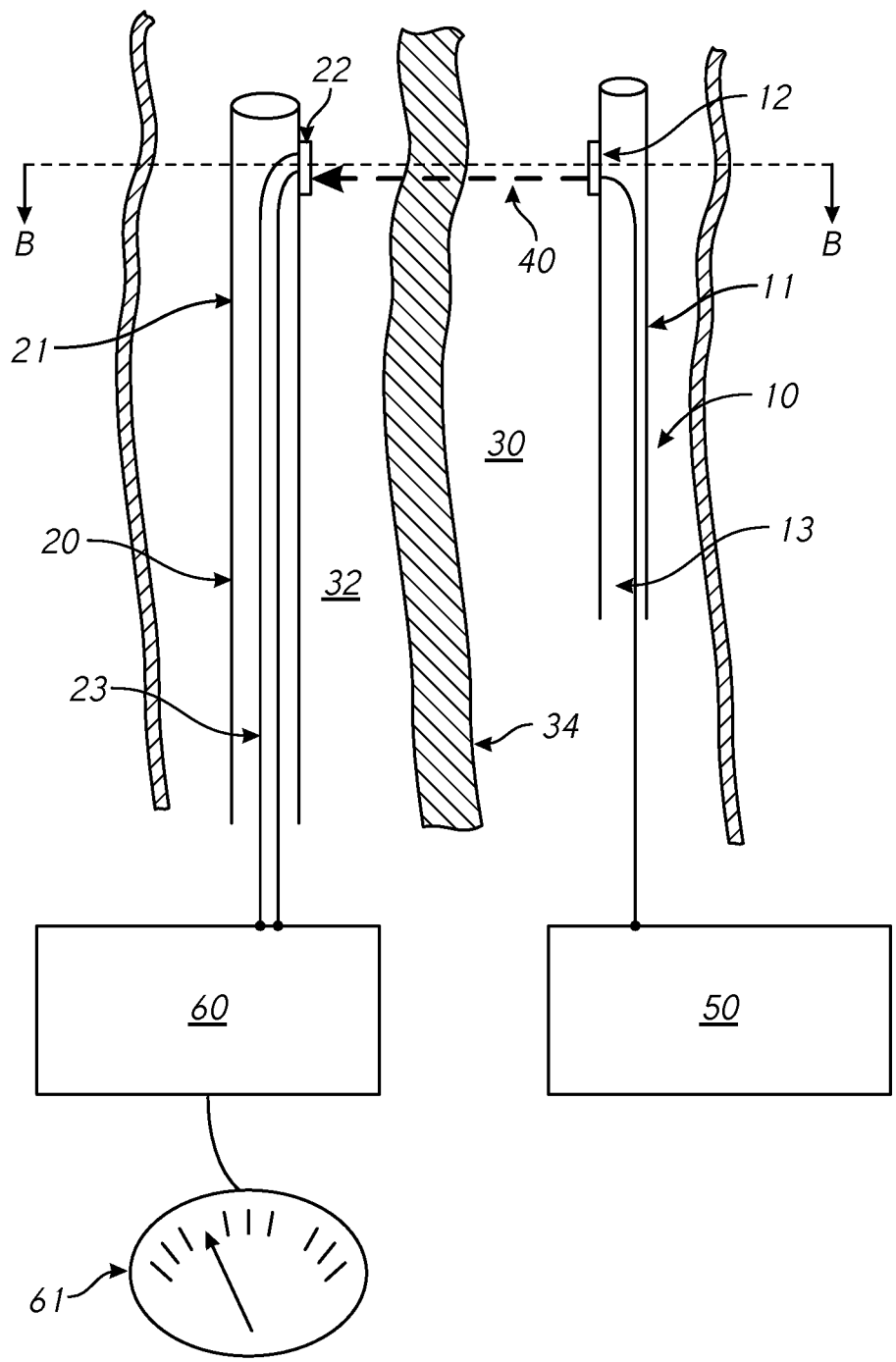
FIG. 1 schematically illustrates an example embodiment of a launching device directing a signal from a first body cavity to a target device in a second body cavity.

FIG. 1 schematically illustrates an example embodiment of a launching device 10 directing a signal from a first body cavity 30 to a target device 20 in a second body cavity 35. The launching device 10 comprises a signal transmitter 12. The launching device 10 may comprise, for example, a catheter including an elongate flexible rod-like portion and a tip portion, and may provides a conduit for administering therapy within the body of a patient. The launching device 10 may be suitable for location and movement through a first cavity or vessel 30 (e.g., heart chamber, coronary artery, coronary vein, peripheral artery, peripheral vein) within a patient's body. The elongate portion of the launching device 10 comprises an outer sheath 11 that encloses a space, defining a lumen 13. The space within the lumen 13 may be suitably partitioned or subdivided as necessary so as to define channels for administering therapy, controlling the positioning of the launching device 10, etc. Such subdivision may, for example, be achieved either longitudinally or concentrically in an axial fashion.

The launching device 10 comprises a signal transducer 12. The signal transducer 12 is configured to provide or emit a signal 40 that is directed outwards from the launching device 10. In the embodiment shown in FIG. 1, the signal 40 is directed radially outward from the launching device 10 in a direction that is perpendicular to the longitudinal axis of the launching device 10. As mentioned in greater detail below, in some embodiments, the direction of the signal 40 need not be perpendicular and can be directed at an angle to the longitudinal axis of the launching device 10. The signal transducer 12 may thereby form at least a portion of a signal generating means.

The signal transducer 12 is connected to signal transmitter 50. The signal transmitter 50 can be suitably selected from ultrasound or appropriate electromagnetic sources such as a laser, microwave radiation, radio waves, etc. In some embodiments, as described in further detail below, the signal transmitter 50 is configured to generate an ultrasound signal, which is relayed to the signal transducer 12, which in turn directs the signal 40 out of the first body cavity 30 into the surrounding tissue.

A target device 20 is located within an adjacent second body cavity or vessel 32 (e.g., heart chamber, coronary artery, coronary vein, peripheral artery, peripheral vein) within a patient's body. The first and second body cavities 30, 32 are separated by intervening tissue 34, sometimes referred to as interstitial tissue or a septum. The first and second body cavities 30, 32 are located next to each other in a parallel fashion for at least a portion of their respective lengths. For example, many of the veins and arteries of the body are known to run in parallel with each other for at least a portion of their overall length.

The target device 20 can assume a similar arrangement to that of the launching device 10. For example, the target device 20 can comprise a catheter including an elongate flexible rod-like portion and a tip portion. For another example, fine movement and positioning of the target device 20 within the body cavity 32 can be achieved. For yet another example, the target device 20 may comprise an outer sheath 21 that encloses a space, defining a lumen 23. The lumen 23 can be suitably partitioned, for example as with the launching device 10.

The target device 20 comprises a receiving transducer 22 configured to receive the signal 40 from the transducer 12 of the launching device 10. The receiving transducer 22 makes up at least a portion of a signal detection means. In use, when the receiving transducer 22 receives the signal 40 transmitted from the signal transducer 12, the receiving transducer 22 transmits the received signal to a signal detector 60. The signal detector 60 is configured to provide an output reading to the user of the system, for example via an output display 61. The output display 61 may be a visual display, an audio display (e.g., beeping or emitting some other sound upon receipt of a signal), etc.

In this way, the transmission and detection of the directed signal 40 can allow for the navigation and positioning of the launching device 10 relative to the target device 20. In use, the launching device 10 and the target device 20 can be maneuvered by the user of the system until the output display 61 indicates that signal 40 is being received by the target device 40.

In some embodiments, the signal 40 comprises or is an ultrasound signal. The signal 40 is directional and is emitted by the signal transducer 12 in the shape of a narrow cone or arc (e.g., with the width of the signal band increasing as the distance from the signal transducer 12 increases). As such, the precision of alignment between the launching device 10 and the target device 20 depends not only upon signal detection, but also upon the distance between the two devices, as the signal beam width is greater at greater distances. This level of error is referred to as "positional uncertainty." A certain level of tolerance can exist for positional uncertainty; however, if therapy is to be directed with precision, the amount of uncertainty should be reduced or minimized. For example, if the diameter d of the signal transducer 12 is 1 mm and the frequency of the ultrasound signal is 30 MHz, then the positional uncertainty x (e.g., the margin of error on either side of a center line) is 1 mm at a perpendicular separation of 5 mm between the launching device 10 and the target device 20. For clinical applications, the positional uncertainty generally should not exceed around ±5 mm (for a total signal beam width of 10 mm at the point of reception). In some embodiments, the positional uncertainty is between about ±0.01 mm and about ±4.50 mm or between about ±0.1 mm and about ±2 mm. In some embodiments, the positional uncertainty does not exceed about ±1 mm.

The strength of the signal 40 can be a factor in detection, and signal strength generally diminishes as the distance between the launching device 10 and the target device 20 increases. This distance is in part determined by the amount of intervening tissue 34 between the devices 10, 20. By way of example, if the signal 40 is an ultrasound signal, significant deterioration of signal can be expected when the launching device 10 and the target device 20 a separated by more than about 20 mm of solid tissue (e.g., the intervening tissue 34). The density of the intervening tissue 34 may also have an effect upon the deterioration of signal 40 over distance (e.g., denser tissue deteriorating the signal more than less dense tissue).

The frequency of the ultrasound signal may also affect the thickness of the signal transducer, which for a standard ultrasound ceramic transducer (e.g., a piezoelectric transducer (PZT)) is 0.075 mm at 30 MHz.

Figure 2:
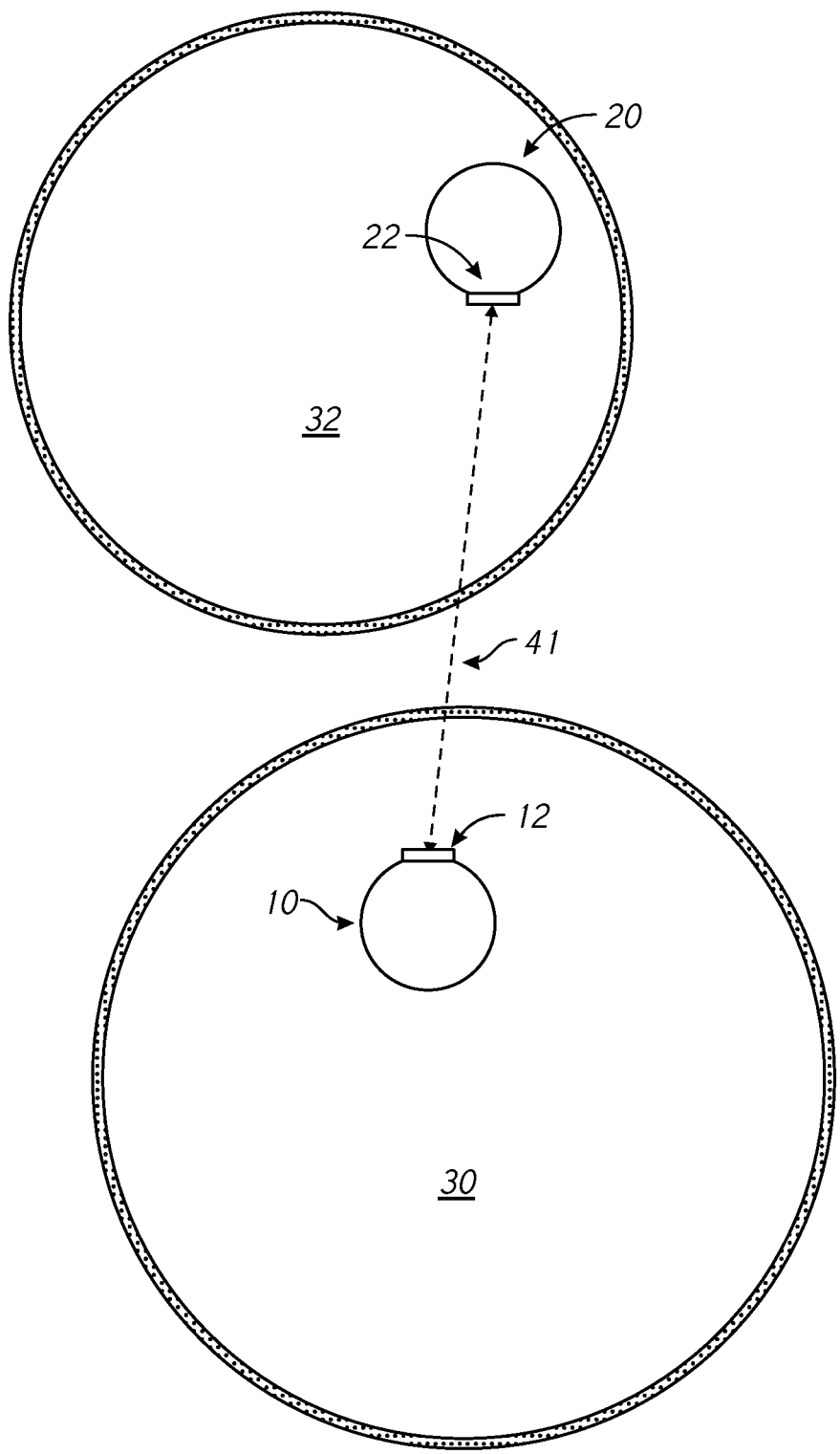
FIG. 2 is a cross-sectional representation along the dotted line B-B of FIG. 1.

FIG. 2 is a cross-sectional representation along the dotted line B-B of FIG. 1. The correct orientation of the launching device relative to the target device can be a factor in detection, as the line of orientation 41 can determine where the therapy is to be applied. The clinical need for precisional placing of therapy in a patient may function better if the directional signal 40 is linked to the means for delivering therapy (e.g., being parallel and longitudinally offset). For example, in this way the user of the system can administer therapy to the correct location by ensuring that the launching device 10 and the target device 20 are correctly positioned via transmission and reception of the signal 40. The orientation line 41 in FIG. 2 denotes not only the direction of signal travel but also the path along which therapy can be administered to the patient.

Figure 3:
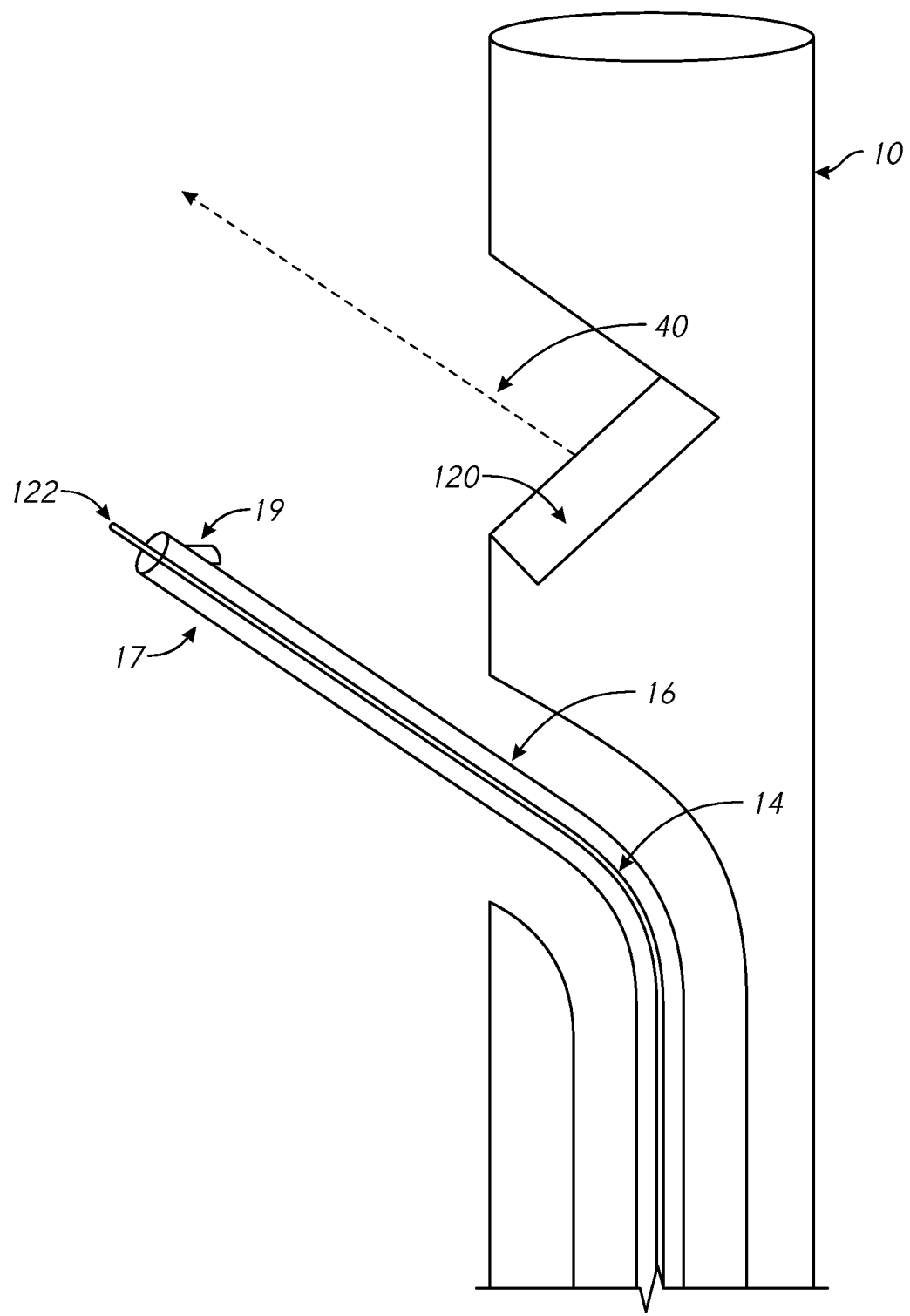
FIG. 3 schematically illustrates an example embodiment of a launching device.

FIG. 3 schematically illustrates an example embodiment of a launching device 10. The launching device 10 comprises a signal transducer 120 that is oriented at an oblique angle relative to the longitudinal axis of the launching device 10. The signal 40 is transmitted at an angle that is in the direction of travel (e.g., forward travel, transverse travel) of the launching device 10 as the launching device enters a body cavity 30 (FIGS. 1 and 2). In some embodiments, the beam angle is about perpendicular to the longitudinal axis of the launching device 10. In some embodiments, the beam angle is between about 20° and about 60° to the perpendicular, between about 30° and about 50° to the perpendicular, or about 45° to the perpendicular, when 0° corresponds to the longitudinal axis of the launching device 10 in the direction of travel.

The launching device 10 comprises a hollow needle or cannula 17, which is an example means for administering therapy. During travel of the launching device 10, the hollow needle 17 is located in an undeployed or retracted state within the lumen 13 of launching device 10. The hollow needle 17 may be deployed/extended from the launching device 10 via an aperture 16 in the outer sheath 11 at a time deemed appropriate by the user (e.g., upon detection of the signal 40 by the target device 20). The aperture 16 can allow fluid communication between the lumen 13 and the body cavity 30 (FIG. 1). As illustrated by the example embodiment of FIG. 3, the hollow needle 17 may travel along a path that is parallel to the direction of the signal 40. The hollow needle 17 may be used to pierce the intervening tissue 34 (FIG. 1). In some embodiments, the hollow needle 17 makes a transit across the entirety of the intervening tissue 34, and in doing so allows the launching device 10 to access the second body cavity 32 (FIG. 2). If desired, the pathway made by the hollow needle 17 through the intervening tissue 34 can be subsequently widened to allow fluid communication between the first body cavity 30 and the second body cavity 32.

Therapeutic means suitable for use in several embodiments can comprise, for example, devices and/or instruments selected from the group consisting of a cannula, a laser, a radiation-emitting device, a probe, a drill, a blade, a wire, a needle, appropriate combinations thereof, and the like.

In some embodiments, the hollow needle 17 comprises a sensor 19, which may assist in further determining positional information of the tip of the hollow needle 17 relative to the launching device 10. In some embodiments, the sensor 19 is configured to detect changes in hydrostatic pressure. Other sensors that are suitable for use in the systems and methods described herein can include temperature sensors, oxygenation sensors, and/or color sensors.

Optionally, the hollow needle 17 can comprise an additional signal transducer 122. In the embodiment shown in FIG. 3, the signal transducer 122 is located near the tip of the hollow needle 17 on the end of a guidewire 14. The signal transducer 122 can also or alternatively located on the hollow needle 17 if desired. In use, the signal transducer 122 is driven with a short transmit pulse that produces a directional signal or a non-directional signal pulse. The signal pulse can be detected by the receiving transducer 22 mounted on the target device 20. The distance from the guidewire 14 or hollow needle 17 to the receiving transducer 22 and hence the target device 20 can be at least partially determined time based on the delay between the transmission of the signal pulse from the signal transducer 122 and receipt of the signal pulse on the receiving transducer 22.

Figure 4:
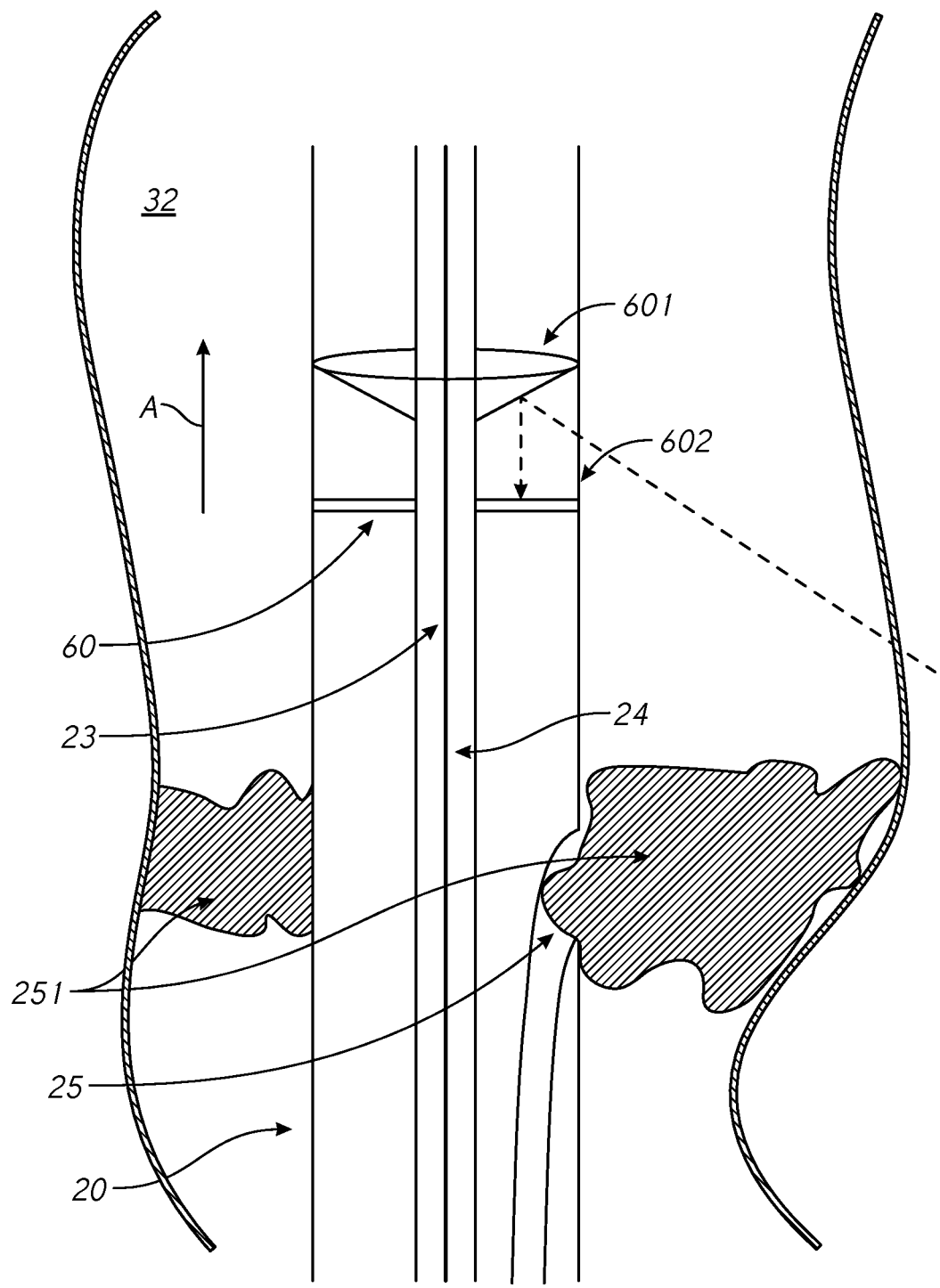
FIG. 4 schematically illustrates an example embodiment of a target device.

FIG. 4 schematically illustrates an example embodiment of a target device 20. In the embodiment shown in FIG. 4, the target device 20 is located within a body cavity 32. As mentioned above, the target device 20 comprises a receiving transducer 22 for receiving the signal 40. The receiving transducer 22 can be unidirectional (e.g., capable of receiving or configured to receive a signal from one direction only) or omnidirectional (e.g., capable of receiving or configured to receive a signal from any direction). Arrow A shows the reversed direction of blood flow after an arterial-venous arterialization (also called PICVA) has been effected. The target device 20 comprises an omnidirectional ultrasound signal receiving transducer 60. An optional reflecting cone 601 can direct the signal 40 onto a disc-shaped receiving transducer 60. An acoustically transparent window 602 can separate the reflecting cone 601 from the receiving transducer 60. In some embodiments, an omnidirectional ultrasound signal receiving transducer can be obtained by locating a cylinder of a flexible piezoelectric material such as polyvinyldifluoride (PVDF) around the outer sheath of the target device 20. In such a way, the cylinder can act in a similar or equivalent manner to the receiving transducer 60.

In the embodiment illustrated in FIG. 4, the target device 20 comprises an optional channel 25 for administering an agent, such as a therapeutic agent, to a patient. In some embodiments, the channel 25 functions as a conduit to allow application of a blocking material 251 that serves to at least partially obstruct or occlude the body cavity 32. The blocking material 251 can be suitably selected from a gel-based substance. The blocking material 251 can also or alternatively include embolization members (e.g., balloons, self-expanding stents, etc.). The placement of the blocking material 251 can be directed by movement of the target device 20. The presence of a guide member 24 within the lumen 23 of the target device 20 can allow the user to precisely manipulate the position of the target device 20 as desired.

Figure 5:
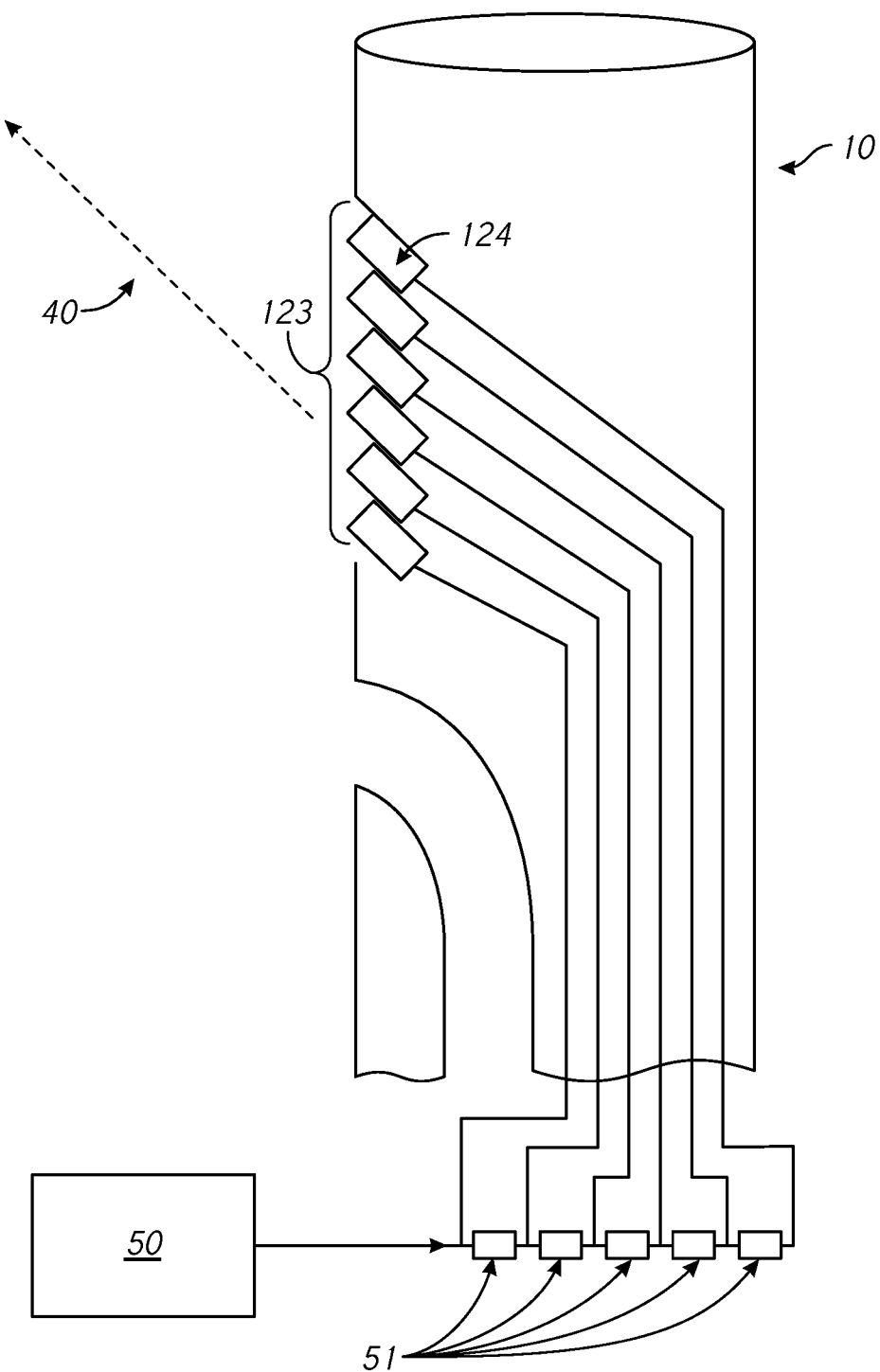
FIG. 5 schematically illustrates another example embodiment of a launching device.

Referring again to FIG. 2, the launching device 10 comprises a signal transducer 12 that may optionally be oriented so that the signal 40 is transmitted at an angle other than perpendicular to the signal transducer 12. FIG. 5 schematically illustrates another example embodiment of a launching device 10. In some embodiments, for example the launching device 10 shown in FIG. 5, the signal transducer is in the form of a signal transducer array 123. The signal transducer array 123 comprises a plurality of signal transducer elements 124, which can be oriented collectively to at least partially define a signal beam width and angle relative to the launching device 10. Smaller size of the elements 124 can allow the signal transducer 123 to not occupy a significant proportion the lumen 13 of the launching device 10.

The embodiment shown in FIG. 5 may be useful for ultrasound beam-forming signaling. FIG. 5 shows an array of signal transducer elements 124 that are separately connected to a transmitter 50 via delays 51, which allows the signals to each element 124 to be delayed relative to each other. The delays can provide or ensure that the ultrasound wavefronts from each element 124 are aligned to produce a beam of ultrasound 40 at the desired angle. In some embodiments, for example in which the signal 40 comprises visible light, an array of LEDs can also or alternatively be used.

Figure 6:
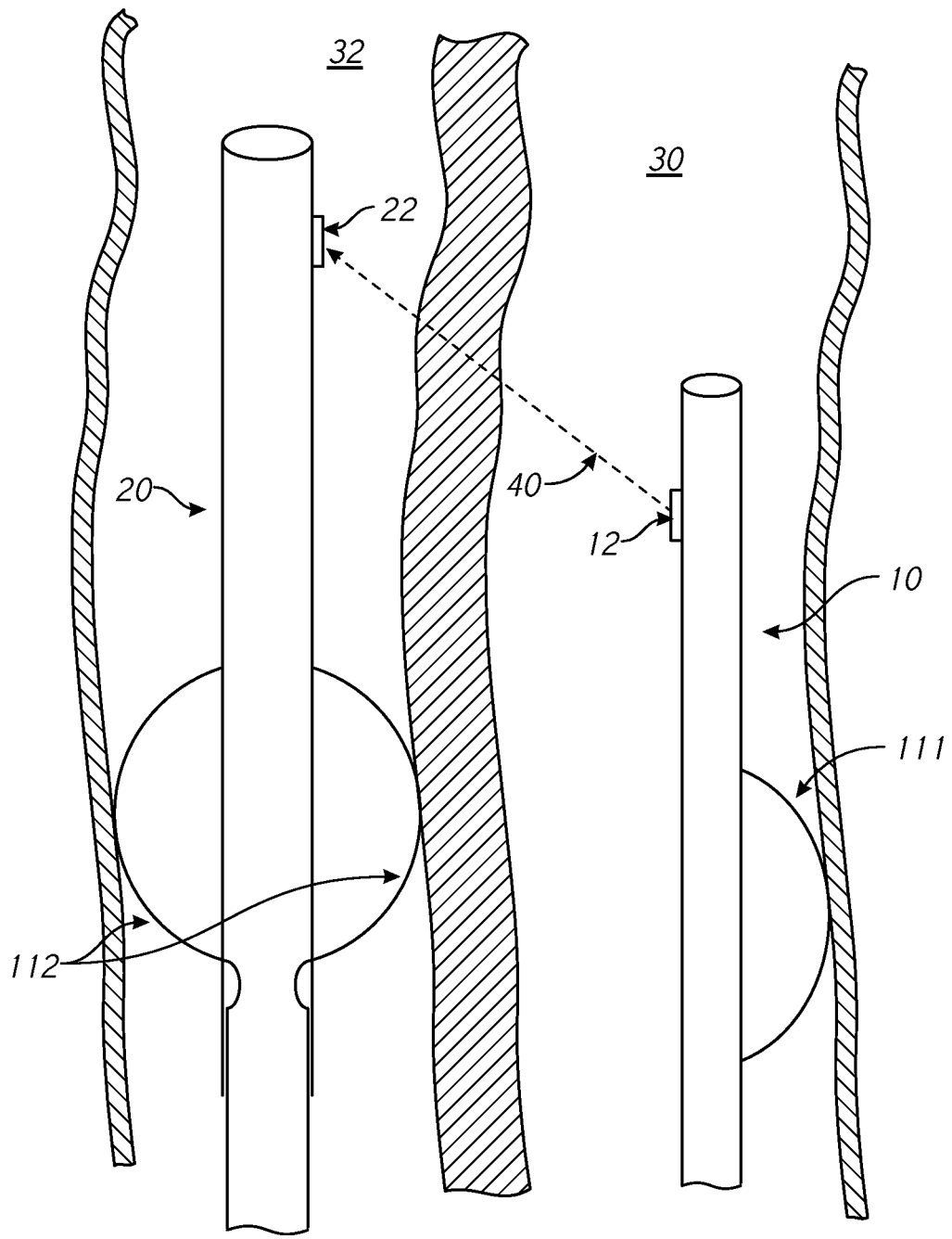
FIG. 6 schematically illustrates an example embodiment of centering devices for launching and/or target devices.

FIG. 6 schematically illustrates an example embodiment of centering devices for launching and/or target devices 10, 20. To assist in the process of alignment between the launching device 10 in the first body cavity 30 and the target device 20 in the second body cavity 32, one or both of the devices 10, 20 may comprise means for centering the respective devices within their body cavities.

In some embodiments, the centering means comprises an inflatable bladder or balloon 111 that is located in the lumen 13, 23 when in an undeployed state and, when the device 10, 20 reaches the desired location within the patient, can be inflated. The balloon 111 can be disposed on an outer surface of the outer sheath 11, 21. The balloon 111 can be annular in shape such that it at least partially surrounds the device 10, 20 in a toroidal or doughnut-like fashion. The balloon 111 can be arranged such that it inflates on only one side or only on two opposite sides of the device 10, 20. As illustrated in FIG. 6, the balloon 111 is deployed on one side of the launching device 10.

In some embodiments, the centering means comprises one or more loop structures 112 located either in the lumen 13, 23 or within recesses made in the outer sheath 11, 21 when in an undeployed or retracted state. When the device 10, 20 reaches the desired location within the patient, the one or more loop structures 112 can be expanded radially outwardly from the device 10, 20, thereby centering the device 10, 20 within the body cavity 30, 32. Outward expansion of the loop structures 112 can be suitably effected by compression of a length of wire, for example, such that it bows outwardly from the outer sheath 11, 21. A centering device that adopts this conformation may comprise a plurality of compressible lengths of wire or other suitable flexible material arranged in parallel at radially spaced intervals around the periphery of the outer sheath 11, 21. Compression of the plurality of wires can be induced by way of a sliding member (not shown) located proximally and/or distally near to the ends of the plurality of wires. The sliding member is capable of translational movement along the longitudinal axis of the device 10, 20. As illustrated in FIG. 6, the target device 20 comprises fully deployed centering means 112 that has allowed the target device 20 to be centered within the body cavity 32.

Other possible means for centering the devices 10, 20 within the body cavities 30, 32 include, but are not limited to, expandable Chinese-lantern type devices, reversibly expandable stents, coils, helices, retractable probes or legs, combinations thereof, and the like.

In some embodiments, the centering means or other means (e.g., balloons, metal stand-offs having differing lengths, etc.) can be used to orient the devices 10, 20 within the body cavities 30, 32 other than in the center or substantially the center of the body cavities. For example, the device 10 may be oriented proximate to the wall of the body cavity 30 where the needle 17 will exit the body cavity 30, which can, for example, provide a shorter ultrasound signal path and/or reduce error due to the needle 17 traversing intraluminal space. For another example, the device 10 may be oriented proximate to the wall of the body cavity 30 opposite the wall of the body cavity 30 where the needle 17 will exit the body cavity 30, which can, for example, provide a firm surface for the needle 17 to push against. For yet another example, the device 20 may be oriented proximate to the wall of the body cavity 32 where the needle 17 will enter the body cavity 32, which can, for example, provide a shorter ultrasound signal path. Other device orientations that are neither centered nor proximate to a vessel wall are also possible (e.g., some fraction of the diameter away from the wall and/or the center of the lumen, such as ½, ⅓, ¼, etc.).

EXAMPLE

The methods and systems described herein demonstrate particular utility in cardiovascular surgery according to several embodiments. Certain aspects are further illustrated by the following non-limiting example, in which the system is used by a clinician to perform the procedure of arterial-venous connection (PICVA) so as to enable retroperfusion of cardiac tissue following occlusion of a coronary artery.

The launching catheter 10 is inserted into the occluded coronary artery by standard keyhole surgical techniques (e.g., tracking over a guidewire, tracking through a guide catheter). The target catheter 20 is inserted into the coronary vein that runs parallel to the coronary artery by standard keyhole surgical techniques (e.g., tracking over a guidewire, tracking through a guide catheter). The coronary vein is not occluded and, therefore, provides an alternative channel for blood flow to the cardiac muscle, effectively allowing the occlusion in the coronary artery to be bypassed.

The launching catheter 10 comprises a PZT ultrasound transducer 12 (e.g., available from CTS Piezoelectric Products of Albuquerque, N. Mex.) that is oriented such that a directional ultrasound beam is transmitted in this example at a 45° angle (relative to the longitudinal axis of the launching device), preferably in the direction of blood flow in the artery 30, although other angles including about 90° are also possible. The ultrasound transducer 12 is activated, and in this example a 30 MHz directional ultrasound signal 40 is transmitted from the launching catheter 10, although other frequencies are also possible. The target catheter 20 comprises an omnidirectional ultrasound receiving transducer 60. To assist with localization of both the launching catheter 10 and the target catheter 20, both catheters 10, 20 comprise centering or orienting means, in this example in the form of an annular inflatable balloon 111, although other or absence of centering or orienting means are also possible. The centering means 111 on the launching catheter 10 is deployed by the clinician when the launching catheter 10 is deemed to be in an appropriate location close to the site of the occlusion within the coronary artery 30. This may be determined via standard fluoroscopic imaging techniques and/or upon physical resistance. The target catheter 20 is then moved within the adjacent coronary vein 32 until the directed ultrasound signal 40 is detected by the signal receiving transducer 60. To enable more precise alignment between the launching catheter 10 and the target catheter 20, the centering means 111 on the target catheter 20 can be deployed either before or after the signal 40 is detected.

Upon reception of the transmitted signal 40, the clinician can be certain that the launching catheter 10 and the target catheter 20 are correctly located, both rotationally and longitudinally, within their respective blood vessels 30, 32 to allow for the arterial-venous connection procedure to commence. The target catheter 20 may be used to block blood flow within the coronary vein 32 via administration of a gel blocking material 251 though a channel 25 in the target catheter 20. The blocking material 251 may be administered at a position in the coronary vein 32 that is downstream in terms of the venous blood flow relative to the location of the receiving signal transducer 60.

The clinician may then initiate arterial-venous connection by deploying a hollow needle 17 from the launching catheter 10 substantially along a path that is parallel and close to the path taken by the ultrasound signal 40 though the intervening tissue 34 between the coronary artery 30 and the coronary vein 32, or the hollow needle 17 may traverse a path that intercepts the path of the ultrasound signal at a point within the coronary vein 32. The hollow needle 17 optionally comprises a sensor 19 near its tip that is configured to detect changes in hydrostatic pressure or Doppler flow such that the user can monitor the transition from arterial pressure to venous pressure as the hollow needle 17 passes between the two vessels 30, 32. The hollow needle 17 optionally comprises a guidewire 14 in a bore or lumen of the hollow needle 17 during deployment. Once the hollow needle 17 and guidewire 14 have traversed the intervening tissue 34, the hollow needle 17 may be retracted back into the lumen 13 of the launching catheter 10, leaving the guidewire 14 in place. In some embodiments, once the hollow needle 17 has traversed the intervening tissue 34, the user can separately pass the guidewire 14 through the bore or lumen of the hollow needle 17 and then retract the needle 17 into the launching catheter 10.

Figure 7:
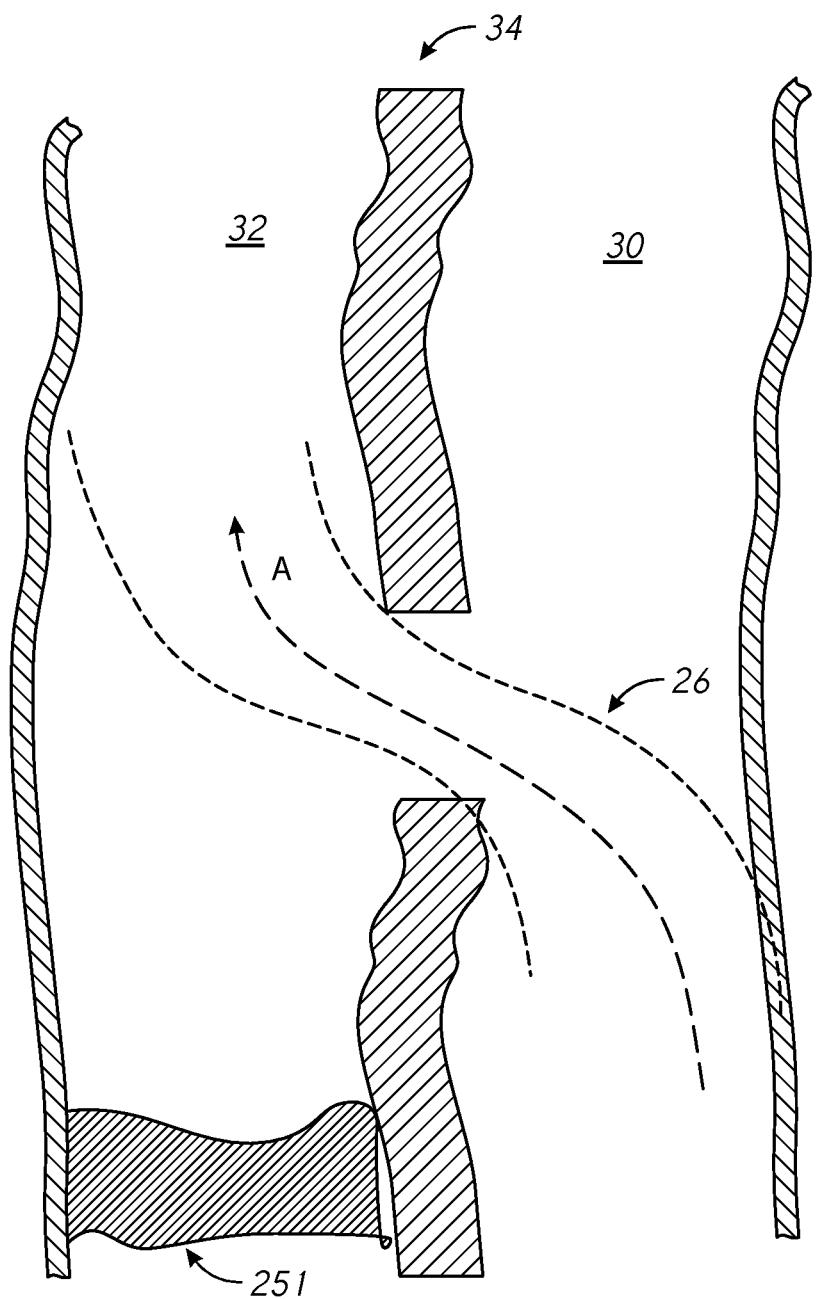
FIG. 7 schematically illustrates a prosthesis in place following a procedure such as arterial-venous arterialization.

The clinician withdraws the launching catheter 10 from the patient, leaving the guidewire 14 in place. A further catheter device is then slid along the guidewire 14. FIG. 7 schematically illustrates a prosthesis 26 such as an expandable stent 26 in place following a procedure such as arterial-venous arterialization. Further detail about possible prostheses including stents and stent-grafts are provided below. The stent 26 may be deployed to widen the perforation in the intervening tissue 34 between the coronary artery 30 and the coronary vein 32, in which the interrupted arrow A shows the direction of blood flow through the stent 26 between the first and second body cavities 30, 32 (e.g., arterial blood is thereby diverted into the venous system and is enabled to retroperfuse the cardiac muscle tissue). The stent 26 can block flow upwards in the cavity 32, forcing blood flow in the cavity 32 to be in the same direction as blood flow in the cavity 30. Graft material of the stent 26 can form a fluid-tight lumen between the cavity 30 and the cavity 32. The target catheter 20 is withdrawn from the patient, leaving the blocking material 251 in position. Optionally, a further block or suture may be inserted into the coronary vein to inhibit or prevent reversal of arterial blood flow, as described in further detail herein.

Whilst the specific example described above is with respect to cardiovascular surgery, the methods and systems described herein could have far reaching applications in other forms of surgery. For example, any surgery involving the need to direct therapy from one body cavity (e.g., for treatment of peripheral artery disease) towards another adjacent body cavity could be considered. As such, applications in the fields of neurosurgery, urology, and general vascular surgery are also possible. The type of therapy need not be restricted to formation of channels between body cavities. For instance, the methods and systems described herein may also be used in directing techniques such as catheter ablation, non-contact mapping of heart chambers, the delivery of medicaments to precise areas of the body, and the like.

Certain techniques for effectively bypassing an occlusion in an artery by percutaneous surgery are described above. These techniques include creating a channel or passage between a first passage, such as an artery upstream of an occlusion, a vein, or a heart chamber, and a second passage, such as an artery, vein, or heart chamber, proximate to the first passage to interconnect the first and second passages by a third passage. Fluid such as blood may be diverted from the first passage into the second passage by way of the interconnecting third passage. In embodiments in which the first passage includes an artery and the second passage includes a vein, the arterial blood can perfuse into tissue in a retrograde manner (retroperfusion).

As described above, an interconnecting passage between first and second body passages can be created by, for example, deploying a needle outwards from a first catheter located within the first passage, so that the needle traverses the interstitial tissue or septum between the first and second passages. A second catheter may be located in the second passage, so as to provide a target device which receives a signal, for example an ultrasound signal, transmitted from the first catheter. By monitoring the received signal, the position of the first catheter with respect to the second catheter can be determined so as to ensure that the needle is deployed in the correct position and orientation to create a passage for fluid flow between the first and second passages.

In order to provide or maintain the flow of blood thorough the interconnecting passage or channel, a structure including a lumen may be inserted in the passage to support the interstitial tissue and/or to inhibit or prevent the passage from closing. The tube may, for example, include a stent expanded in the channel using a balloon catheter or self-expansion, as described herein. A catheter to deliver the structure, for example a balloon catheter or catheter that allows self-expansion, may be guided to the channel by a guidewire deployed in the passage by the first catheter.

Passages such as arteries, veins, and heart chambers can pulsate as the heart beats, for example due to movement of heart walls, peripheral limbs, and/or fluctuations in pressure within the passages themselves. This pulsation can cause movement of the passages relative to each another, which can impose stress on a structure within an interconnecting passage therebetween. This stress may be large in comparison to stress experienced by a structure within a single passage. Stress can lead to premature failure of the structure, for example by fatigue failure of the stent struts. Failure of the structure may result in injury to the interstitial tissue and/or occlusion of the interconnecting passage, which could lead to significant complications or complete failure of the therapy.

Figure 8:
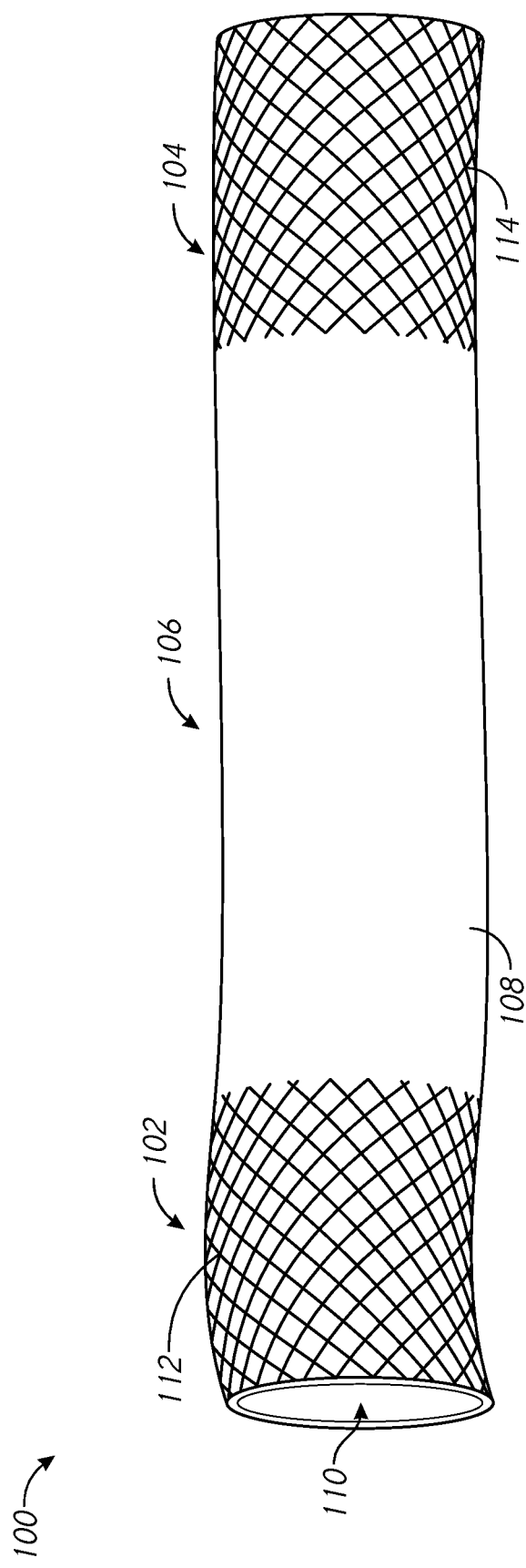
FIG. 8 is a side perspective view of an example embodiment of a device for providing fluid flow.

FIG. 8 illustrates a device or implant or prosthetic 100 for providing or maintaining fluid flow through at least one passage. The device 100 includes a first or proximal end portion 102, a second or distal end portion 104, and an intermediate portion 106 between the proximal end portion 102 and the distal end portion 104. The device includes a bore or lumen 110 for passage of fluid through the device 100. The device 100, for example at least the intermediate portion 106 of the device 100, includes a flexible polymer tube 108. The flexible polymer tube 108 may at least partially define the lumen 110.

The device 100 includes a support structure (e.g., at least one stent) including a mesh 112 and a mesh 114. In some embodiments, at least a portion of the mesh 112 is embedded in the outside wall of the tube 108 proximate to the proximal end portion 102 of the device 100. In some embodiments, at least a portion of the mesh 114, for example a wire or a strut, is embedded in the outside wall of the tube 108 proximate to the distal end portion 104 of the device 100. The meshes 112, 114 may include biocompatible metal such as stainless steel and/or shape memory material such as nitinol or chromium cobalt.

The wire meshes 112, 114 can stiffen the end portions 102, 104, respectively. In some embodiments in which the intermediate portion 106 does not include a mesh, the intermediate portion 106 may be relatively flexible in comparison to the end portions 102, 104, and/or the end portions 102, 104 may have a relatively high radial stiffness.

In some embodiments, the end portions 102, 104 of the device 100 are diametrically expandable. For example, the wire meshes 112, 114 may have a smaller diameter after formation or manufacture than the passages, for example blood vessels, into which the device 100 will be deployed. When the device 100 is in position in the passages, the end portions 102, 104 can be expanded or deformed outwardly so that the respective diameters of the end portions 102, 104 increase, for example to abut the interior sidewalls of the passages. The end portions 102, 104 are configured to maintain the expanded diameter indefinitely, for example by plastic deformation of the material (e.g., wires, struts) of the meshes 112, 114 and/or by provision of a locking mechanism arranged to mechanically lock the meshes 112, 114 in the expanded position. The intermediate portion 106 of the device 100 may be diametrically expandable, for example by way of plastic deformation of the tube 108.

Figure 9:
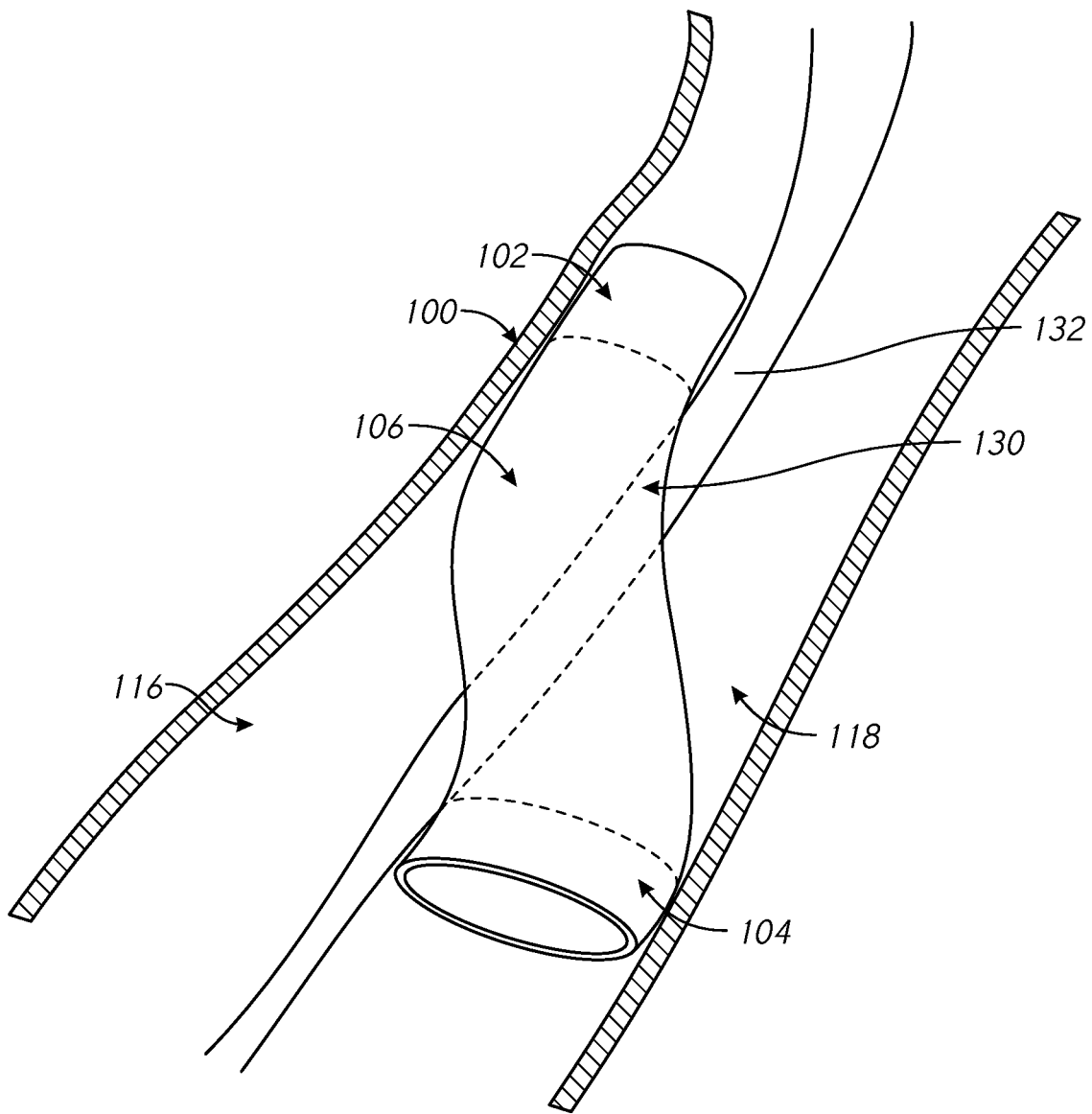
FIG. 9 shows the device of FIG. 8 in use as a shunt between two blood vessels.

FIG. 9 shows the device 100 of FIG. 8 deployed to provide a fluid flow path between a first passage 116 and a second passage 118. The passages 116, 118 may include coronary blood vessels, for example a coronary artery 116 and a coronary vein 118, or vice versa. The passages 116, 118 may include peripheral blood vessels (e.g., blood vessels in limbs), for example a femoral or other peripheral artery 116 and a femoral or other peripheral vein 118, or vice versa. The end portions 102, 104 and the intermediate portion 106 of the device 100 have been expanded to meet with and push against the inner walls of the passages 116, 118. The distal end portion 104 of the device 100 is located within the second passage 118, and the proximal end portion 102 of the device 100 is located within the first passage 116. The intermediate portion 106 extends through an opening or interconnecting passage 130 surgically formed between the passages 116, 118.

The expanded end portions 102, 104 of the device 100 are resilient, and impart an outward radial force on the inner walls of the passages 116, 118. By virtue of the radial stiffness of the end portions 102, 104 of the device 100, the end portions 102, 104 are held or anchored in place within the respective passages 116, 118. Slippage of the device 100 within the passages 116, 118 is thereby prevented or reduced. In this way, the end portions 102, 104 of the device 100 can anchor or fix the device 100 in position, in use, while providing or maintaining fluid flow through the lumen 110 of the tube 108 (FIG. 8). In this way, the device 100 can act as a shunt between the first passage 116 and the second passage 118.

The intermediate portion 106 of the device 100 may be flexible, for example allowing the intermediate portion 106 to form an 'S' shape formed by the combination of the first passage 116, the second passage 118, and the interconnecting passage 130 (FIG. 9). The flexible intermediate portion 106 can allow the end portions 102, 104 of the device 100 to move with respect to one another in response to relative movement of the passages 116, 118.

In embodiments in which the intermediate portion 106 does not include a wire mesh but includes the flexible polymer material of the tube 108, the intermediate portion 106 may not be susceptible to damage due to mesh fatigue, for example upon cyclic or other stress imparted by relative movement of the passages 116, 118.

The intermediate portion 106 of the device 100 has sufficient resilience to maintain dilatation of the interconnecting passage 130, so that the interconnecting passage 130 remains open to provide or maintain a path for blood flow from the artery 116 to the vein 118 by way of the lumen 110 of the tube 108 (FIG. 8). Blood flow from the artery 116 to the vein 118, by way of the interconnecting passage 130, may thereby be provided or maintained through the lumen 110 of the tube 108. The device 100 at least partially supports the artery 116, the vein 118, and the interconnecting passage 130 to provide a pathway for fluid communication through the device 100.

The proximal end portion 102 and the distal end portion 104 of the device 100 are arranged so that, when the device 100 is deployed with the distal end portion 104 in a vein 118 and the proximal end portion 102 in an artery 116, for example as shown in FIG. 9, the diameter of the expanded distal end portion 104 is sufficient to hold the distal end portion 104 within the vein 118, and the diameter of the expanded proximal end portion 102 is sufficient to hold the proximal end portion 102 within the artery 116. The diameter of the proximal end portion 102 may therefore differ from the diameter of the distal end portion 104. By selecting appropriate diameters for the end portions 102, 104 and the intermediate portion 106, the device 100 can be tailored to a certain anatomy and/or the anatomy of an individual patient.

An example procedure for positioning the device 100 of FIG. 8 to provide a shunt between an occluded artery 116 and a vein 118 (e.g., a coronary artery 116 and a coronary vein 118, or a peripheral artery 116 and a peripheral vein 118) to achieve retroperfusion of arterial blood, for example as shown in FIG. 9, will now be described.

A catheter may be inserted into the patient's arterial system by way of a small aperture cut, usually in the patient's groin area. The catheter is fed to the artery 116 and guided to a position upstream of the site of the occlusion, for example at a site proximate and parallel or substantially parallel to a vein 118. A hollow needle is deployed from the catheter, through the wall of the artery 116, through the interstitial tissue 132 that separates the artery 116 and vein 118, and through the wall of the vein 118. The path of the needle creates an interconnecting passage or opening 130, which allows blood to flow between the artery 116 and the vein 118. Deployment of the needle may be guided by a transmitter (e.g., a directional ultrasound transmitter) coupled to a catheter in the artery 116 and a receiver (e.g., an omnidirectional ultrasound receiver) coupled to a catheter in the vein 118, or vice versa, for example as described herein and in U.S. patent application Ser. No. 11/662,128. Other methods of forming the opening 130 are also possible (e.g., with or without directional ultrasound guidance, with other types of guidance such as described herein, from vein to artery, etc.).

Before the needle is withdrawn from the passage 130, a guidewire (e.g., as described with respect to the guidewire 14 of FIG. 3) is inserted through the hollow needle and into the vein 118. The needle is then retracted, leaving the guidewire in place in the artery 116, the passage 130, and the vein 118. The catheter carrying the needle can then be withdrawn from the patient's body. The guidewire can be used to guide further catheters to the interconnecting passage 130 between the artery 116 and the vein 118.

A catheter carrying the device 100 in a non-expanded state is advanced towards the interconnecting passage 130, guided by the guidewire, for example by a rapid exchange lumen or through the lumen 110. The catheter may include, for example, a balloon catheter configured to expand at least a portion of the device 100 and/or a catheter configured to allow self-expansion of at least a portion of the device 100. The distal end portion 104 of the device 100 is passed through the interconnecting passage 130 and into the vein 118, leaving the proximal end portion 102 in the artery 116. The intermediate portion 106 of the device 100 is at least partially in the passage 130, and is at least partially within the artery 116 and the vein 118. The intermediate portion 106 flexes to adopt a curved or "S"-shaped formation, depending on the anatomy of the site. Adoption of such curvature may conform the shape of an intermediate portion 106 extending through the interconnecting passage 130, and optionally into at least one of the passages 116, 118, to the shape of at least the interconnecting passage 130.

The distal end portion 104 of the device 100 is expanded, for example upon inflation of a balloon or by self-expansion, so as to increase the diameter of the distal end portion 104 and anchor the distal end portion 104 against the inner wall of the vein 118. The catheter may be adapted to expand the intermediate portion 106 of the device 100, for example by inflation of a balloon, so that the interconnecting passage 130 can be widened or dilated to obtain blood flow (e.g., sufficient blood flow) from the artery 116 to the vein 118. The proximal end portion 102 of the device 100 is expanded, for example upon inflation of a balloon or by self-expansion, so as to increase the diameter of the proximal end portion 102 and anchor the proximal end portion 102 against the inner wall of the artery 116.

After the end portions 102, 104 of the device 100 are expanded, for example due to self-expansion and/or balloon expansion, and with or without improving expansion after deployment, the catheter and the guidewire are withdrawn from the patient's body. In this way, the device 100 is anchored or fixed in position within the vein 118, the artery 116, and the interconnecting passage 130 as shown in FIG. 9. In embodiments in which the device 100 comprises a stent-graft, the graft, which can form a fluid-tight passage between the artery 116 and the vein 118, can inhibit or prevent blood from flowing antegrade in the vein 118 because such passageway is blocked, which can be in addition to or instead of a blocking agent in the vein 118.

The catheter may be adapted to selectively expand the proximal end portion 102, the distal end portion 104, and/or the intermediate portion 106 of the device 100 individually or in combination, for example by the provision of two or more separately inflatable balloons or balloon portions, a single balloon configured to expand all of the portions of the device 100 simultaneously, or a single balloon configured to expand one or more selected portions of the device 100. For example, the end portions 102, 104 may be self-expanding, and the intermediate portion 106 may be expanded by a balloon to dilate the passage 130. In some embodiments including balloon expansion, all or selected parts of the device 100 may be expanded, for example, simultaneously by a balloon across the entire length of the device 100 or by a plurality of balloons longitudinally spaced to selectively inflate selected parts of the device 100, and/or sequentially by a balloon or plurality of balloons. In some embodiments including at least partial self-expansion, all or selected parts of the device 100 may be expanded, for example, by proximal retraction of a sheath over or around the device 100, which can lead to deployment of the device 100 from distal to proximal as the sheath is proximally retracted. Deployment of the device 100 proximal to distal and deployment of the device 100 intermediate first then the ends are also possible. In some embodiments, for example embodiments in which the device 100 is at least partially conical or tapered, a conical or tapered balloon may be used to at least partially expand the device 100. In certain such embodiments, a portion of the balloon proximate to the vein 118 may have a larger diameter than a portion of the balloon proximate to the artery 116, for example such that the device 100 can adapt to changing vein diameters due to any increase in pressure or blood flow in the vein 118.

Other steps may be included in the procedure. For example, before the device 100 is deployed, a balloon catheter may be guided to the interconnecting passage 130 and positioned so that an inflatable balloon portion of the catheter lies in the interconnecting passage 130. Upon inflation of the balloon, the balloon pushes against the walls of the interconnecting passage 130 to widen or dilate the interconnecting passage 130 to ease subsequent insertion of the device 100.

Figure 10:
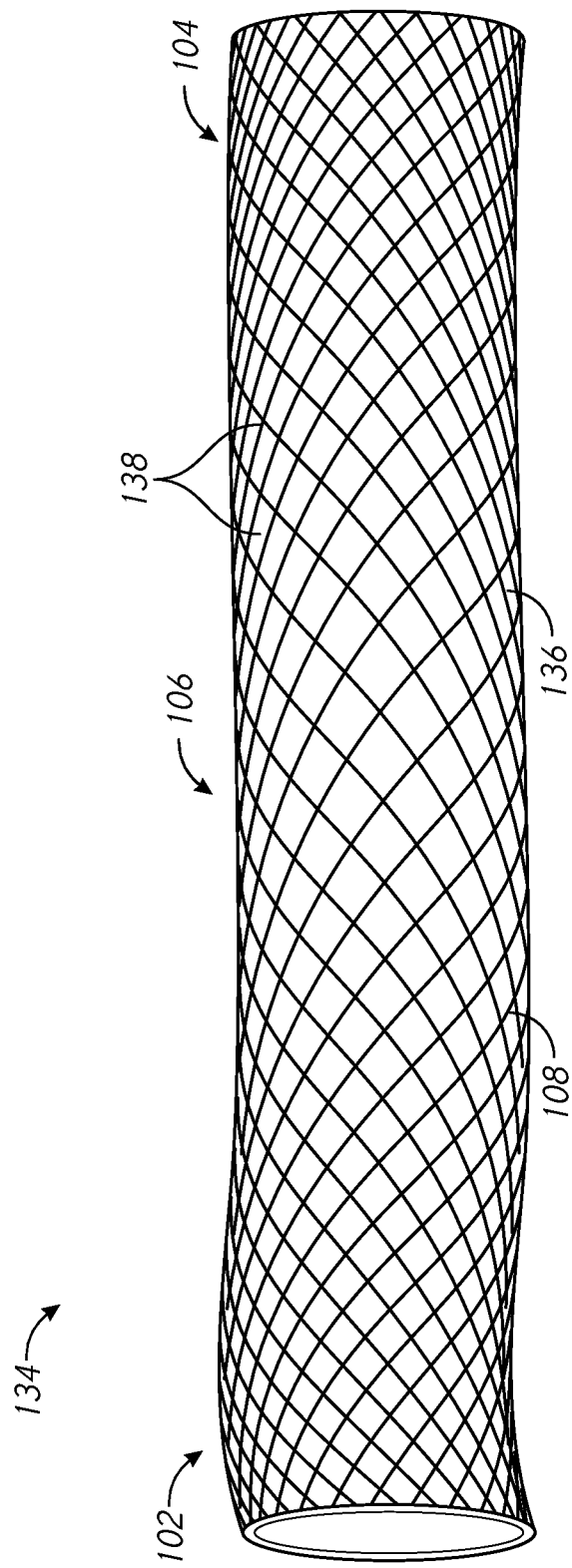
FIG. 10 is a side perspective view of another example embodiment of a device for providing fluid flow.

FIG. 10 illustrates another device 134 for providing fluid flow through at least one passage. The device 134 includes a mesh 136 and a polymer tube 108. The mesh 136 is shown as being on the outside of the polymer tube 108, but as described herein could also or alternatively be on an inside of the polymer tube and/or within the polymer tube 108. As described with respect to the device 100, the device 134 includes a proximal end portion 102, a distal end portion 104, and an intermediate portion 106. In the embodiment illustrated in FIG. 10, the mesh 136 extends along the entire length of the device 134, including along the intermediate portion 106.

In some embodiments, the spacing of filaments or struts of the mesh 136 varies along the length of the device 134. For example, winding density of a woven or layered filamentary mesh may be varied and/or a window size pattern of a cut mesh may be varied.

In some embodiments, the spacing may be relatively small in the proximal end portion 102 and the distal end portions 104, and the spacing may be relatively large in the intermediate portion 106. In other words, the density or window size of the mesh 136 may be relatively low in the intermediate portion 106, and the density or window size of the mesh 136 may be relatively high in the end portions 102, 104. In certain such embodiments, the intermediate portion 106 may be flexible in comparison to the end portions 102, 104. The relatively rigid end portions 102, 104 may engage and anchor in passages. Although the mesh 136 in the intermediate portion 106 may be subject to stress such as cyclic stress, in use, the relatively high flexibility of the intermediate portion 106 due to the low density or window size allows the impact of the stress to be low because the intermediate portion 106 can flex in response to the stress. The risk of fatigue failure of the device 134, and particularly the filaments or struts 138 of the mesh 136, may therefore be reduced in comparison to a device having uniform flexibility along its entire length.

In some embodiments, the spacing may be relatively large in the proximal end portion 102 and the distal end portions 104, and the spacing may be relatively small in the intermediate portion 106. In other words, the density of the mesh 136 may be relatively high (or the window size of the mesh 136 may be relatively low) in the intermediate portion 106, and the density of the mesh 136 may be relatively low (or the window size of the mesh 136 may be relatively high) in the end portions 102, 104. In certain such embodiments, the intermediate portion 106 may have radial strength sufficient to inhibit or prevent collapse of the passage 130, yet still, flexible enough to flex in response to stress such as cyclic stress. The end portions 102, 104 may engage and anchor in passages.

Figure 11:
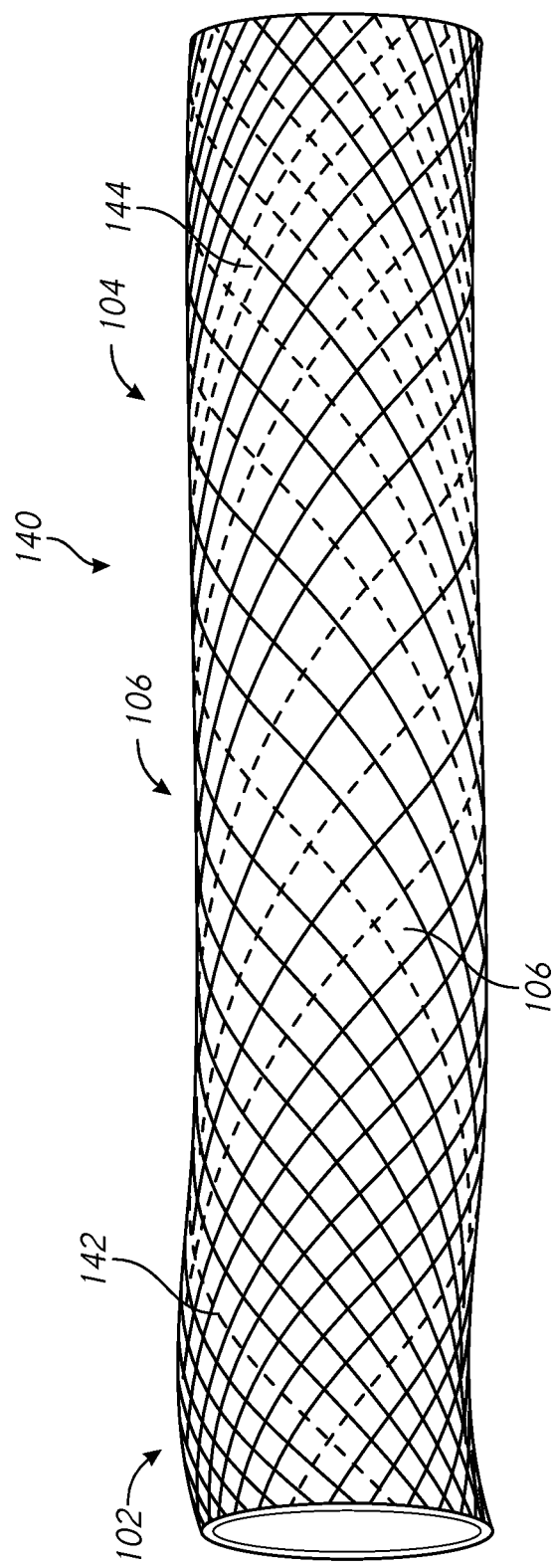
FIG. 11 is a side perspective view of still another example embodiment of a device for providing fluid flow.

FIG. 11 illustrates another device or implant or prosthetic 140 for providing fluid flow through at least one passage. As described with respect to the device 100, the device 140 includes a proximal end portion 102, a distal end portion 104, and an intermediate portion 106. The device 140 includes a polymer tube 108 and a support structure including a first mesh 142 and a second mesh 144. The first mesh 142 extends from the proximal end portion 102 toward (e.g., into) the intermediate portion 106 and optionally into the distal end portion 104. The second mesh 144 extends from the distal end portion 104 toward (e.g., into) the intermediate portion 106 and optionally into the proximal end portion 102. The meshes 142, 144 thereby overlap each other at least in the intermediate portion 106. Both meshes 142, 144 may be on the outside of the tube 108, on the inside of the tube 108, or embedded within the tube 108, or one mesh may be on the outside of the tube 108, on the inside of the tube 108, or embedded within the tube 108 while the other mesh is differently on the outside of the tube 108, on the inside of the tube 108, or embedded within the tube 108 (e.g., one mesh inside the tube 108 and one mesh outside the tube 108). The meshes 142, 144 may be formed, for example, by winding wire in a lattice configuration around or inside the polymer tube 108, by placing a cut tube around or inside the polymer tube 108, by being embedded in the polymer tube 108, combinations thereof, and the like.

In some embodiments, the density of the meshes 142, 144 is relatively high (or the window size of the meshes 142, 144 is relatively low) in their respective end portions 102, 104 and decreases in density (or increases in window size) towards the intermediate portion 106. The total winding density (e.g., the winding density of both meshes 142, 144, taken together) may be lower in the intermediate portion 106 than in the end portions 102, 104, or the total window size (e.g., the window size of both meshes 142, 144, taken together) may be higher in the intermediate portion 106 than in the end portions 102, 104. In certain such embodiments, the intermediate portion 106 is relatively flexible in comparison to the end portions 102, 104. In some embodiments, the meshes 142, 144 do not extend into the intermediate portion, and absence of a mesh could cause the intermediate portion 106 to be relatively flexible in comparison to the end portions 102, 104. In some embodiments, as window size increases (e.g., longitudinally along a tapered portion of the device 140), the density decreases, the mesh coverage decreases, and/or the porosity increases because the width of the struts and/or filaments remains substantially constant or constant or does not increase in the same proportion as the window size, which could provide a change in flexibility along a longitudinal length.

The first and second meshes 142, 144 may include different materials, which can allow optimization of the properties of each of the respective distal and proximal end portions 102, 104 of the device 140 for a particular application of the device 140. For example, the second mesh 144 at the distal end portion 104 of the device 140 may include a relatively flexible metallic alloy for ease of insertion through an interconnecting passage between two blood vessels, while the first mesh 142 at the proximal end portion 102 of the device 140 may include a relatively inelastic metallic alloy to provide a high degree of resilience at the proximal end portion 104 to anchor the device 140 firmly in position. The first and second meshes 142, 144 could include the same material composition (e.g., both including nitinol) but different wire diameters (gauge) or strut thicknesses.

Figure 12:
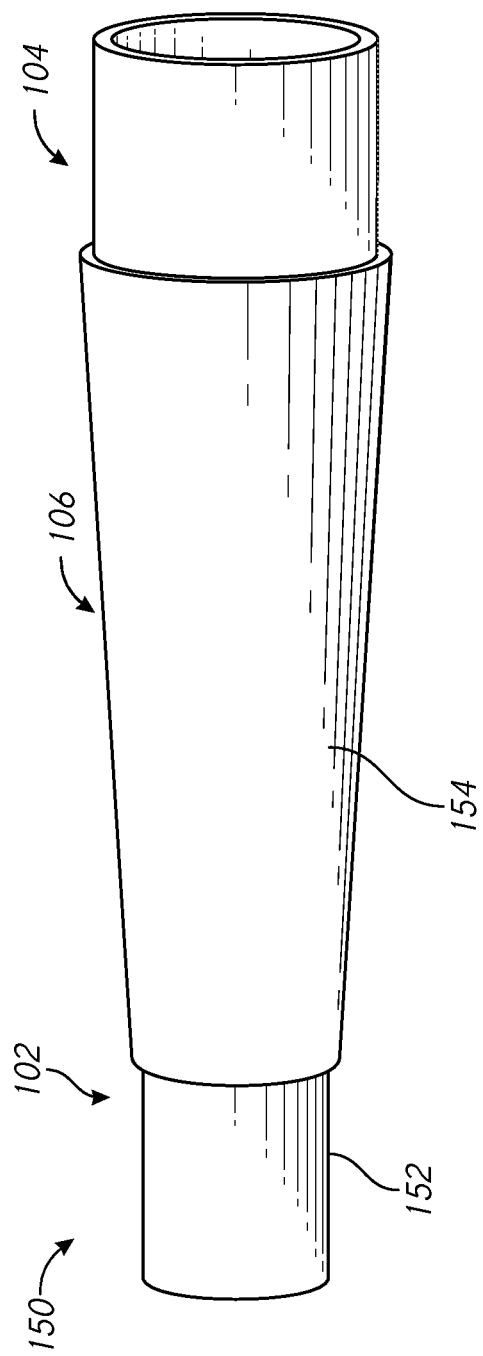
FIG. 12 is a side perspective view of yet another example embodiment of a device for providing fluid flow.

FIG. 12 illustrates another device or implant or prosthetic 150 for providing fluid flow through at least one passage. The device 150 includes a support structure (e.g., stent) 152 and a graft 154. As described with respect to the device 100, the device 150 includes a proximal end portion 102, a distal end portion 104, and an intermediate portion 106. The proximal end portion 102 includes a cylindrical or substantially cylindrical portion and the distal end portion 104 includes a cylindrical or substantially cylindrical portion. The diameter of the proximal end portion 102 is smaller than the diameter of the distal end portion 104. In some embodiments, the diameter of the proximal end portion 102 is larger than the diameter of the distal end portion 104. The intermediate portion 106 has a tapered or frustoconical shape between the proximal end portion 102 and the distal end portion 104. The stent 152 may include filaments (e.g., woven, layered), a cut tube or sheet, and/or combinations thereof.

Parameters of the stent 152 may be uniform or substantially uniform across a portion and/or across multiple portions, or may vary within a portion and/or across multiple portions. For example, the stent 152 at the proximal end portion 102 may include a cut tube or sheet, the stent 152 at the distal end portion 102 may include a cut tube or sheet, and the stent 152 at the intermediate portion 106 may include filaments (e.g., woven or layered). Certain such embodiments may provide good anchoring by the proximal end portion 102 and the distal end portion 104 and good flexibility (e.g., adaptability to third passage sizes and dynamic stresses) of the intermediate portion 106.

The stent 152 may include different materials in different portions. For example, the stent 152 at the proximal end portion 102 may include chromium cobalt and/or tantalum, the stent 152 at the distal end portion 104 may include nitinol, and the stent 152 at the intermediate portion 106 may include nitinol. Certain such embodiments may provide good anchoring and/or wall apposition by the device 150 in each deployment areas (e.g., the proximal end portion 102 engaging sidewalls of an artery, the distal end portion 104 engaging sidewalls of a vein, and the intermediate portion 106 engaging sidewalls of the passage between the artery and the vein). In some embodiments in which the distal end portion 104 is self-expanding, the distal end portion 104 can adapt due to changing vessel diameter (e.g., if vein diameter increases due to an increase in pressure or blood flow), for example by further self-expanding.

Combinations of support structure materials and types are also possible. For example, the stent 152 at the proximal portion may include a cut tube or sheet including chromium cobalt and/or tantalum, the stent 152 at the distal end portion 104 may include a cut tube or sheet including nitinol, and the stent 152 at the intermediate portion 106 may include filaments including nitinol.

In embodiments in which the stent 152 includes at least one portion including a cut tube or sheet, the cut pattern may be the same. For example, the cut pattern may be the same in the proximal end portion 102 and the distal end portion 104, but proportional to the change in diameter. In some embodiments, the window size or strut density is uniform or substantially uniform within a portion 102, 104, 106, within two or more of the portions 102, 104, 106, and/or from one end of the stent 152 to the other end of the stent 152. In embodiments in which the stent 152 includes at least one portion including filaments, the winding may be the same. For example, the winding may be the same in the proximal end portion 102 and the distal end portion 104, but changed due to the change in diameter. In some embodiments, the winding density or porosity is uniform or substantially uniform within a portion 102, 104, 106, within two or more of the portions 102, 104, 106, and/or from one end of the stent 152 to the other end of the stent 152. In embodiments in which the stent 152 includes at least one portion including a cut tube or sheet and at least one portion including filaments, the cut pattern and winding may be configured to result in a uniform or substantially uniform density. Non-uniformity is also possible, for example as described herein.

The graft 154 may include materials and attachment to the stent 152 as described with respect to the tube 108. The graft 154 generally forms a fluid-tight passage for at least a portion of the device 150. Although illustrated as only being around the intermediate portion 106, the graft 154 may extend the entire length of the device 150, or may partially overlap into at least one of the cylindrical end portions 102, 104.

Figure 13:
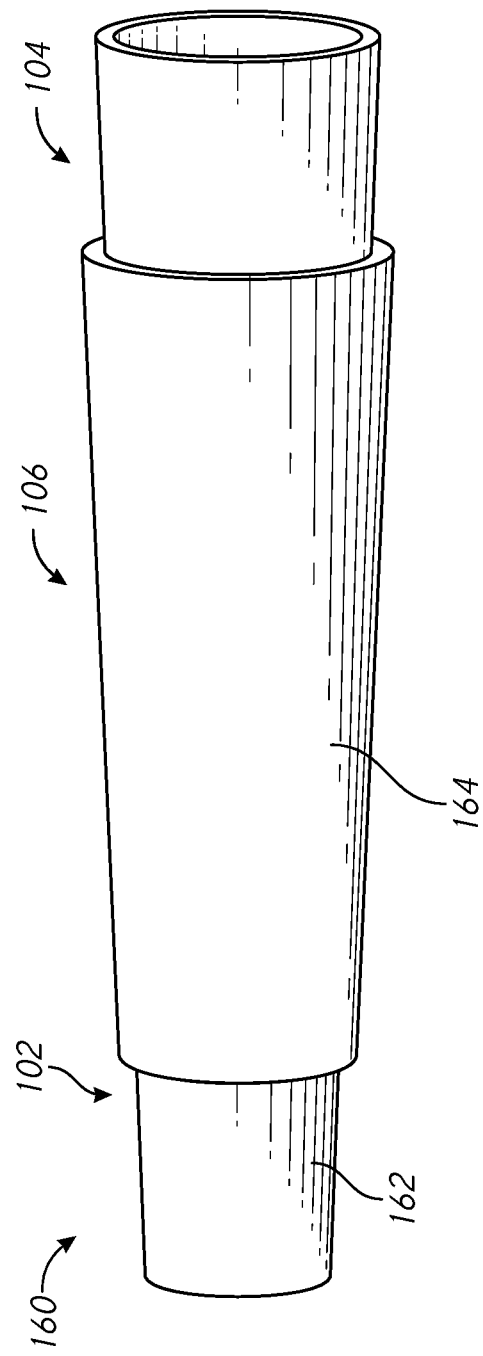
FIG. 13 is a side perspective view of yet still another example embodiment of a device for providing fluid flow.

FIG. 13 illustrates another device 160 for providing fluid flow through at least one passage. The device 160 includes a support structure (e.g., stent) and a graft 164. As described with respect to the device 100, the device 160 includes a proximal end portion 102, a distal end portion 104, and an intermediate portion 106. The proximal end portion 102 includes a tapered or frustoconical portion and the distal end portion 104 includes a tapered or frustoconical portion. The diameter of the proximal end of the proximal end portion 102 is smaller than the diameter of the distal end of the distal end portion 104. In some embodiments, the diameter of the proximal end of the proximal end portion 102 is larger than the diameter of the distal end of the distal end portion 104. The intermediate portion 106 has a tapered or frustoconical shape between the proximal end portion 102 and the distal end portion 104. In some embodiments, the angle of inclination of the portions 102, 104, 106 is the same or substantially the same (e.g., as illustrated in FIG. 13). In some embodiments, the angle of inclination of at least one portion is sharper or narrower than at least one other portion. The frustoconical proximal end portion 102 and distal end portion 104 may allow better anchoring in a body passage, for example because arteries tend to taper with distance from the heart and veins tend to taper with distance towards the heart, and the end portions 102, 104 can be configured to at least partially correspond to such anatomical taper.

FIG. 12 illustrates a device 150 comprising a first cylindrical or straight portion, a conical or tapered portion, and second cylindrical or straight portion. FIG. 13 illustrates a device 160 comprising one or more conical or tapered sections (e.g., the entire device 160 being conical or tapered or comprising a plurality of conical or tapered sections). In some embodiments, combinations of the devices 150, 160 are possible. For example, a device may comprise a cylindrical or straight portion and a conical or tapered portion for the remainder of the device. In certain such embodiments, the device may have a length between about 1 cm and about 10 cm (e.g., about 5 cm), which includes a cylindrical or straight portion having a diameter between about 1 mm and about 5 mm (e.g., about 3 mm) and a length between about 0.5 cm and about 4 cm (e.g., about 2 cm) and a conical or tapered portion having a diameter that increases from the diameter of the cylindrical or straight portion to a diameter between about 3 mm and about 10 mm (e.g., about 5 mm) and a length between about 1 cm and about 6 cm (e.g., about 3 cm). Such a device may be devoid of another cylindrical or conical portion thereafter.

As described above with respect to the support structure 152, the support structure 162 may include filaments (e.g., woven, layered), a cut tube or sheet, the same materials, different materials, and combinations thereof.

The graft 164 may include materials and attachment to the stent 162 as described with respect to the tube 108. The graft 164 generally forms a fluid-tight passage for at least a portion of the device 160. Although illustrated as only being around the intermediate portion 106, the graft 164 may extend the entire length of the device 160, or may partially overlap into at least one of the frustoconical end portions 102, 104.

In some embodiments, a combination of the device 150 and the device 160 are possible. For example, the proximal end portion 102 can be cylindrical or substantially cylindrical (e.g., as in the device 150), the distal end portion 104 can be tapered or frustoconical (e.g., as in the device 160), with the proximal end portion 102 having a larger diameter than the distal end of the distal end portion 104. For another example, the proximal end portion 102 can be tapered or frustoconical (e.g., as in the device 160), the distal end portion 104 can be cylindrical or substantially cylindrical (e.g., as in the device 150), with the proximal end of the proximal end portion 102 having a larger diameter than the distal end portion 104. In each example, the intermediate portion 106 can have a tapered or frustoconical shape between the proximal end portion 102 and the distal end portion 104.

An example deployment device for the implantable devices described herein is described in U.S. patent application Ser. No. 12/545,982, filed Aug. 24, 2009, and U.S. patent application Ser. No. 13/486,249, filed Jun. 1, 2012, the entire contents of each of which is hereby incorporated by reference. The device generally includes a handle at the proximal end with a trigger actuatable by a user and a combination of tubular member at the distal end configured to be pushed and/or pulled upon actuation of the trigger to release the device. Other delivery devices are also possible. The delivery device may include a portion slidable over a guidewire (e.g., a guidewire that has been navigated between the artery and the vein via a tissue traversing needle) and/or may be trackable through a lumen of a catheter.

Although certain embodiments and examples are shown or described herein in detail, various combinations, sub-combinations, modifications, variations, substitutions, and omissions of the specific features and aspects of those embodiments are possible, some of which will now be described by way of example only.

The device, for example a stent of the device, a mesh of the device, a support structure of the device, etc., may be self-expanding. For example, a mesh may include a shape-memory material, such as nitinol, which is capable of returning or configured to return to a pre-set shape after undergoing deformation. In some embodiments, the stent may be manufactured to a shape that is desired in the expanded configuration, and is compressible to fit inside a sleeve for transport on a catheter to a vascular site. To deploy and expand the stent, the sleeve is drawn back from the stent to allow the shape memory material to return to the pre-set shape, which can anchor the stent in the passages, and which may dilate the passages if the stent has sufficient radial strength. The use of a balloon catheter is not required to expand a fully self-expanding stent, but may be used, for example, to improve or optimize the deployment.

A device may include one or more self-expanding portions, and one or more portions which are expandable by deformation, for example using a balloon catheter. For example, in the embodiment shown in FIG. 11, the first mesh 142 may include stainless steel expandable by a balloon catheter, and the second mesh 144 may include nitinol for self-expansion upon deployment.

With respect to any of the embodiments described herein, the polymer tube 108, including the grafts 154, 164, may include any suitable compliant or flexible polymer, such as PTFE, silicone, polyethylene terephthalate (PET), polyurethane such as polycarbonate aromatic biodurable thermoplastic polyurethane elastomer (e.g., ChronoFlex C® 80A and 55D medical grade, available from AdvanSource Biomaterials of Wilmington, Mass.), combinations thereof, and the like. The polymer tube 108 may include biodegradable, bioabsorbable, or biocompatible polymer (e.g., polylactic acid (PLA), polyglycolic acid (PGA), polyglycolic-lactic acid (PLGA), polycaprolactone (PCL), polyorthoesters, polyanhydrides, combinations thereof, etc. The polymer may be in tube form before interaction with a support structure (e.g., stent), or may be formed on, in, and/or around a support structure (e.g., stent). For example, the polymer may include spun fibers, a dip-coating, combinations thereof, and the like. In some embodiments, for example when the device is to be deployed within a single blood vessel, the device may omit the tube. In certain such embodiments, the intermediate portion of the stent may include a mesh with a low winding density or high window size, while the end portions of the stent include a mesh with a higher winding density or lower window size, the mesh being generally tubular to define a pathway for fluid flow through the center of the mesh. In some embodiments, the polymer tube 108 includes a lip (e.g., comprising the same or different material), which can help form a fluid-tight seal between the polymer tube 108 and the body passages. The seal may be angled, for example to account for angled positioning of the polymer tube 108 between body passages. In some embodiments, the polymer tube 108 may extend longitudinally beyond the support structure in at least one direction, and the part extending beyond is not supported by the support structure.

The mesh may include any suitable material, such as nickel, titanium, chromium, cobalt, tantalum, platinum, tungsten, iron, manganese, molybdenum, combinations thereof (e.g., nitinol, chromium cobalt, stainless steel), and the like. The mesh may include biodegradable, bioabsorbable, or biocompatible polymer (e.g., polylactic acid (PLA), polyglycolic acid (PGA), polyglycolic-lactic acid (PLGA), polycaprolactone (PCL), polyorthoesters, polyanhydrides, combinations thereof, etc.) and/or glass, and may lack metal. Different materials may be used for portions of the mesh or within the same mesh, for example as previously described with reference to FIG. 11. For example, the mesh 114 at the distal end portion 104 and the mesh 112 at the proximal end portion 102 of the device 100 may include different materials. For another example, the mesh 112, and/or the mesh 114, may include a metallic alloy (e.g., comprising cobalt, chromium, nickel, titanium, combinations thereof, and the like) in combination with a different type of metallic alloy (e.g., a shape memory alloy in combination with a non-shape memory alloy, a first shape memory alloy in combination with a second shape memory alloy different than the first shape memory alloy, a clad material (e.g., comprising a core including a radiopaque material such as titanium, tantalum, rhenium, bismuth, silver, gold, platinum, iridium, tungsten, etc.)) and/or a non-metallic material such as a polymer (e.g., polyester fiber), carbon, and/or bioabsorbable glass fiber. In some embodiments, at least one mesh 112, 114 comprises nitinol and stainless steel. The nitinol may allow some self-expansion (e.g., partial and/or full self-expansion), and the mesh could then be further expanded, for example using a balloon.

Although generally illustrated in FIGS. 8, 10, and 11 as a woven filament mesh, any other structure that can provide the desired degree of resilience may be used. For example, layers of filaments wound in opposite directions may be fused at the filament ends to provide an expandable structure. For another example, a metal sheet may be cut (e.g., laser cut, chemically etched, plasma cut, etc.) to form perforations and then heat set in a tubular formation or a metal tube (e.g., hypotube) may be cut (e.g., laser cut, chemically etched, plasma cut, etc.) to form perforations. A cut tube (including a cut sheet rolled into a tube) may be heat set to impart an expanded configuration.

Filaments or wires or ribbons that may be woven or braided, or layered or otherwise arranged, are generally elongate and have a circular, oval, square, rectangular, etc. transverse cross-section. Example non-woven filaments can include a first layer of filaments wound in a first direction and a second layer of filaments wound in a second direction, at least some of the filament ends being coupled together (e.g., by being coupled to an expandable ring). Example braid patterns include one-over-one-under-one, a one-over-two-under-two, a two-over-two-under-two, and/or combinations thereof, although other braid patterns are also possible. At filament crossings, filaments may be helically wrapped, cross in sliding relation, and/or combinations thereof. Filaments may be loose (e.g., held together by the weave) and/or include welds, coupling elements such as sleeves, and/or combinations thereof. Ends of filaments can be bent back, crimped (e.g., end crimp with a radiopaque material such as titanium, tantalum, rhenium, bismuth, silver, gold, platinum, iridium, tungsten, etc. that can also act as a radiopaque marker), twisted, ball welded, coupled to a ring, combinations thereof, and the like. Weave ends may include filament ends and/or bent-back filaments, and may include open cells, fixed or unfixed filaments, welds, adhesives, or other means of fusion, radiopaque markers, combinations thereof, and the like. Parameters of the filaments may be uniform or substantially uniform across a portion and/or across multiple portions, or may vary within a portion and/or across multiple portions. For example, the proximal end portion 102 may include a first parameter and the distal end portion 104 may include a second parameter different than the first braid pattern. For another example, the proximal end portion 102 and the distal end portion 104 may each include a first parameter and the intermediate portion 106 may include a second parameter different than the parameter. For yet another example, at least one of the proximal end portion 102, the distal end portion 104, and the intermediate portion 106 may include both a first parameter and a second parameter different than the first parameter. Filament parameters may include, for example, filament type, filament thickness, filament material, quantity of filaments, weave pattern, layering, wind direction, pitch, angle, crossing type, filament coupling or lack thereof, filament end treatment, weave end treatment, layering end treatment, quantity of layers, presence or absence of welds, radiopacity, braid pattern, density, porosity, filament angle, braid diameter, winding diameter, and shape setting.

Tubes or sheets may be cut to form strut or cell patterns, struts being the parts of the tube or sheet left after cutting and cells or perforations or windows being the parts cut away. A tube (e.g., hypotube) may be cut directly, or a sheet may be cut and then rolled into a tube. The tube or sheet may be shape set before or after cutting. The tube or sheet may be welded or otherwise coupled to itself, to another tube or sheet, to filaments, to a graft material, etc. Cutting may be by laser, chemical etchant, plasma, combinations thereof, and the like. Example cut patterns include helical spiral, weave-like, coil, individual rings, sequential rings, open cell, closed cell, combinations thereof, and the like. In embodiments including sequential rings, the rings may be coupled using flex connectors, non-flex connectors, and/or combinations thereof. In embodiments including sequential rings, the rings connectors (e.g., flex, non-flex, and/or combinations thereof) may intersect ring peaks, ring valleys, intermediate portions of struts, and/or combinations thereof (e.g., peak-peak, valley-valley, mid-mid, peak-valley, peak-mid, valley-mid, valley-peak, mid-peak, mid-valley). The tube or sheet or sections thereof may be ground and/or polished before or after cutting. Interior ridges may be formed, for example to assist with fluid flow. Parameters of the cut tube or sheet may be uniform or substantially uniform across a portion and/or across multiple portions, or may vary within a portion and/or across multiple portions. For example, the proximal end portion 102 may include a first parameter and the distal end portion 104 may include a second parameter different than the first parameter. For another example, the proximal end portion 102 and the distal end portion 104 may each include a first parameter and the intermediate portion 106 may include a second parameter different than the parameter. For yet another example, at least one of the proximal end portion 102, the distal end portion 104, and the intermediate portion 106 may include both a first parameter and a second parameter different than the first parameter. Cut tube or sheet parameters may include, for example, radial strut thickness, circumferential strut width, strut shape, cell shape, cut pattern, cut type, material, density, porosity, tube diameter, and shape setting.

In some embodiments, the perforations may provide the mesh with a relatively flexible intermediate portion and relatively stiff end portions. The supporting structure may instead be an open-cell foam disposed within the tube.

Filaments of a stent, stent-graft, or a portion thereof, and/or struts of a cut stent, stent-graft, or a portion thereof, may be surface modified, for example to carry medications such as thrombosis modifiers, fluid flow modifiers, antibiotics, etc. Filaments of a stent, stent-graft, or a portion thereof, and/or struts of a cut stent, stent-graft, or a portion thereof, may be at least partially covered with a coating including medications such as thrombosis modifiers, fluid flow modifiers, antibiotics, etc., for example embedded within a polymer layer or a series of polymer layers, which may be the same as or different than the polymer tube 108.

Thickness (e.g., diameter) of filaments of a stent, stent-graft, or a portion thereof, and/or struts of a cut stent, stent-graft, or a portion thereof, may be between about 0.0005 inches and about 0.02 inches, between about 0.0005 inches and about 0.015 inches, between about 0.0005 inches and about 0.01 inches, between about 0.0005 inches and about 0.008 inches, between about 0.0005 inches and about 0.007 inches, between about 0.0005 inches and about 0.006 inches, between about 0.0005 inches and about 0.005 inches, between about 0.0005 inches and about 0.004 inches, between about 0.0005 inches and about 0.003 inches, between about 0.0005 inches and about 0.002 inches, between about 0.0005 inches and about 0.001 inches, between about 0.001 inches and about 0.02 inches, between about 0.001 inches and about 0.015 inches, between about 0.001 inches and about 0.01 inches, between about 0.001 inches and about 0.008 inches, between about 0.001 inches and about 0.007 inches, between about 0.001 inches and about 0.006 inches, between about 0.001 inches and about 0.005 inches, between about 0.001 inches and about 0.004 inches, between about 0.001 inches and about 0.003 inches, between about 0.001 inches and about 0.002 inches, between about 0.002 inches and about 0.02 inches, between about 0.002 inches and about 0.015 inches, between about 0.002 inches and about 0.01 inches, between about 0.002 inches and about 0.008 inches, between about 0.002 inches and about 0.007 inches, between about 0.002 inches and about 0.006 inches, between about 0.002 inches and about 0.005 inches, between about 0.002 inches and about 0.004 inches, between about 0.002 inches and about 0.003 inches, between about 0.003 inches and about 0.02 inches, between about 0.003 inches and about 0.015 inches, between about 0.003 inches and about 0.01 inches, between about 0.003 inches and about 0.008 inches, between about 0.003 inches and about 0.007 inches, between about 0.003 inches and about 0.006 inches, between about 0.003 inches and about 0.005 inches, between about 0.003 inches and about 0.004 inches, between about 0.004 inches and about 0.02 inches, between about 0.004 inches and about 0.015 inches, between about 0.004 inches and about 0.01 inches, between about 0.004 inches and about 0.008 inches, between about 0.004 inches and about 0.007 inches, between about 0.004 inches and about 0.006 inches, between about 0.004 inches and about 0.005 inches, between about 0.005 inches and about 0.02 inches, between about 0.005 inches and about 0.015 inches, between about 0.005 inches and about 0.01 inches, between about 0.005 inches and about 0.008 inches, between about 0.005 inches and about 0.007 inches, between about 0.005 inches and about 0.006 inches, between about 0.006 inches and about 0.02 inches, between about 0.006 inches and about 0.015 inches, between about 0.006 inches and about 0.01 inches, between about 0.006 inches and about 0.008 inches, between about 0.006 inches and about 0.007 inches, between about 0.007 inches and about 0.02 inches, between about 0.007 inches and about 0.015 inches, between about 0.007 inches and about 0.01 inches, between about 0.007 inches and about 0.008 inches, between about 0.008 inches and about 0.02 inches, between about 0.008 inches and about 0.015 inches, between about 0.008 inches and about 0.01 inches, between about 0.01 inches and about 0.02 inches, between about 0.01 inches and about 0.015 inches, or between about 0.015 inches and about 0.02 inches. Other thicknesses are also possible, including thicknesses greater than or less than the identified thicknesses. Filaments and/or struts comprising certain materials (e.g., biodegradable material, materials with less restoring force, etc.) may be thicker than the identified thicknesses.

Thicknesses of filaments and/or struts may be based, for example, on at least one of device or device portion size (e.g., diameter and/or length), porosity, radial strength, material, quantity of filaments and/or struts, cut pattern, weave pattern, layering pattern, and the like. For example, larger filament and/or strut thicknesses (e.g., greater than about 0.006 inches) may be useful for large devices or device portions used to treat large vessels such as coronary vessels, mid-sized filament and/or strut thicknesses (e.g., between about 0.003 inches and about 0.006 inches) may be useful for mid-sized used to treat mid-sized vessels such as peripheral vessels, and small filament and/or strut thicknesses (e.g., less than about 0.003 inches) may be useful for small devices or device portions used to treat small vessels such as veins and neurological vessels.

The internal or external diameter of a stent, a stent-graft, or a first end portion, second end portion, intermediate portion, or subportion thereof, for example taking into account filament or strut thickness, may be between about 1 mm and about 12 mm, between about 1 mm and about 10 mm, between about 1 mm and about 8 mm, between about 1 mm and about 6 mm, between about 1 mm and about 4 mm, between about 1 mm and about 2 mm, between about 2 mm and about 12 mm, between about 2 mm and about 10 mm, between about 2 mm and about 8 mm, between about 2 mm and about 6 mm, between about 2 mm and about 4 mm, between about 4 mm and about 12 mm, between about 4 mm and about 10 mm, between about 4 mm and about 8 mm, between about 4 mm and about 6 mm, between about 6 mm and about 12 mm, between about 6 mm and about 10 mm, between about 6 mm and about 8 mm, between about 8 mm and about 12 mm, between about 8 mm and about 10 mm, or between about 10 mm and about 12 mm. Certain such diameters may be suitable for treating, for example, coronary vessels. The internal or external diameter of a stent, a stent-graft, or a portion thereof, for example taking into account filament or strut thickness, may be between about 1 mm and about 10 mm, between about 1 mm and about 8 mm, between about 1 mm and about 6 mm, between about 1 mm and about 4 mm, between about 1 mm and about 2 mm, between about 2 mm and about 10 mm, between about 2 mm and about 8 mm, between about 2 mm and about 6 mm, between about 2 mm and about 4 mm, between about 4 mm and about 10 mm, between about 4 mm and about 8 mm, between about 4 mm and about 6 mm, between about 6 mm and about 10 mm, between about 6 mm and about 8 mm, or between about 8 mm and about 10 mm. Certain such diameters may be suitable for treating, for example, veins. The internal or external diameter of a stent, a stent-graft, or a portion thereof, for example taking into account filament or strut thickness, may be between about 6 mm and about 25 mm, between about 6 mm and about 20 mm, between about 6 mm and about 15 mm, between about 6 mm and about 12 mm, between about 6 mm and about 9 mm, between about 9 mm and about 25 mm, between about 9 mm and about 20 mm, between about 9 mm and about 15 mm, between about 9 mm and about 12 mm, between about 12 mm and about 25 mm, between about 12 mm and about 20 mm, between about 12 mm and about 15 mm, between about 15 mm and about 25 mm, between about 15 mm and about 20 mm, or between about 20 mm and about 25 mm. Certain such diameters may be suitable for treating, for example, peripheral vessels. The internal or external diameter of a stent, a stent-graft, or a portion thereof, for example taking into account filament or strut thickness, may be between about 20 mm and about 50 mm, between about 20 mm and about 40 mm, between about 20 mm and about 35 mm, between about 20 mm and about 30 mm, between about 30 mm and about 50 mm, between about 30 mm and about 40 mm, between about 30 mm and about 35 mm, between about 35 mm and about 50 mm, between about 35 mm and about 40 mm, or between about 40 mm and about 50 mm. Certain such diameters may be suitable for treating, for example, aortic vessels. Other diameters are also possible, including diameters greater than or less than the identified diameters. The diameter of the device may refer to the diameter of the first end portion, the second end portion, or the intermediate portion, each of which may be in expanded or unexpanded form. The diameter of the device may refer to the average diameter of the device when all of the portions of the device are in either expanded or unexpanded form.

The length of a stent, a stent-graft, or a first end portion, second end portion, intermediate portion, or subportion thereof may be between about 5 mm and about 150 mm, between about 5 mm and about 110 mm, between about 5 mm and about 70 mm, between about 5 mm and about 50 mm, between about 5 mm and about 25 mm, between about 5 mm and about 20 mm, between about 5 mm and about 10 mm, between about 10 mm and about 150 mm, between about 10 mm and about 110 mm, between about 10 mm and about 70 mm, between about 10 mm and about 50 mm, between about 10 mm and about 25 mm, between about 10 mm and about 20 mm, between about 20 mm and about 150 mm, between about 20 mm and about 110 mm, between about 20 mm and about 70 mm, between about 20 mm and about 50 mm, between about 20 mm and about 25 mm, between about 25 mm and about 150 mm, between about 25 mm and about 110 mm, between about 25 mm and about 70 mm, between about 25 mm and about 50 mm, between about 50 mm and about 150 mm, between about 50 mm and about 110 mm, between about 50 mm and about 70 mm, between about 70 mm and about 150 mm, between about 70 mm and about 110 mm, or between about 110 mm and about 150 mm. Other lengths are also possible, including lengths greater than or less than the identified lengths.

The porosity of a stent, a stent-graft, or a first end portion, second end portion, intermediate portion, or subportion thereof may be between about 5% and about 95%, between about 5% and about 50%, between about 5% and about 25%, between about 5% and about 10%, between about 10% and about 50%, between about 10% and about 25%, between about 25% and about 50%, between about 50% and about 95%, between about 50% and about 75%, between about 50% and about 60%, between about 60% and about 95%, between about 75% and about 90%, between about 60% and about 75%, and combinations thereof. The density of a stent may be inverse to the porosity of that stent. The porosity of a portion of a stent covered by a graft may be about 0%. The porosity may vary by objectives for certain portions of the stent. For example, the intermediate portion may have a low porosity to increase fluid flow through the device, while end portions may have lower porosity to increase flexibility and wall apposition.

The radial strength or compression resistance of a stent, a stent-graft, or a first end portion, second end portion, intermediate portion, or subportion thereof may be between about 0.1 N/mm and about 0.5 N/mm, between about 0.2 N/mm and about 0.5 N/mm, between about 0.3 N/mm and about 0.5 N/mm, between about 0.1 N/mm and about 0.3 N/mm, between about 0.1 N/mm and about 0.2 N/mm, between about 0.2 N/mm and about 0.5 N/mm, between about 0.2 N/mm and about 0.3 N/mm, or between about 0.3 N/mm and about 0.5 N/mm.

The values of certain parameters of a stent, a stent-graft, or a first end portion, second end portion, intermediate portion, or subportion thereof may be linked (e.g., proportional). For example, a ratio of a thickness of a strut or filament to a diameter of a device portion comprising that strut or filament may be between about 1:10 and about 1:250, between about 1:25 and about 1:175, or between about 1:50 and about 1:100. For another example, a ratio of a length of a device or portion thereof to a diameter of a device or a portion thereof may be between about 1:1 and about 50:1, between about 5:1 and about 25:1, or between about 10:1 and about 20:1.

Portions of the device may include radiopaque material. For example, filaments and/or struts a stent, a stent-graft, or a first end portion, second end portion, intermediate portion, or subportion thereof may comprise (e.g., be at least partially made from) titanium, tantalum, rhenium, bismuth, silver, gold, platinum, iridium, tungsten, combinations thereof, and the like. For another example, filaments and/or struts of a stent, stent-graft, or a portion thereof may comprise (e.g., be at least partially made from) a material having a density greater than about 9 grams per cubic centimeter. Separate radiopaque markers may be attached to certain parts of the device. For example, radiopaque markers can be added to the proximal end of the device or parts thereof (e.g., a proximal part of the intermediate portion, a proximal part of the distal portion), the distal end of the device or parts thereof (e.g., a distal part of the intermediate portion, a distal part of the proximal portion), and/or other parts. A radiopaque marker between ends of a device may be useful, for example, to demarcate transitions between materials, portions, etc. Radiopacity may vary across the length of the device. For example, the proximal portion could have a first radiopacity (e.g., due to distal portion material and/or separate markers) and the distal portion could have a second radiopacity (e.g., due to distal portion material and/or separate markers) different than the first radiopacity.

In some embodiments, the device includes a polymer tube, and no supporting structure is provided. The intermediate portion of such a device may be relatively more flexible than the end portions by, for example, decreasing the wall thickness of the polymer tube within the intermediate portion.

When a mesh or other supporting structure is provided in combination with a polymer tube, the supporting structure may be located around the outside of the tube, in the inner bore of the tube, or embedded within a wall of the tube. More than one supporting structure may be provided, in which case each supporting structure may have a different location with respect to the tube.

One or both of the end portions of the device may include anchoring elements such as hooks, protuberances, or barbs configured to grasp or grip inner sidewalls of a blood vessel. The radial force of the end portions after expansion may be sufficient to grasp or grip inner sidewalls of a blood vessel without anchoring elements.

There need not be a well-defined transition between the intermediate and end portions. For example, mesh type, material, wall thickness, flexibility, etc. may gradually change from an end portion toward an intermediate portion or from an intermediate portion toward an end portion.

The flexibility of the device may increase gradually when moving from an end portion towards the intermediate portion, for example as described with respect to the devices 134, 140. The change in flexibility may be due to change in mesh density (e.g., winding density, window size), tube thickness, or other factors. The flexibility of the device may be uniform or substantially uniform along the entire length of the support structure (e.g., stent), or along certain portions of the support structure (e.g., along an entire end portion, along the entire intermediate portion, along one end portion and the intermediate portion but not the other end portion, etc.).

While the devices described herein may be particularly suitable for use as a transvascular shunt in percutaneous surgery, the devices could be used in many other medical applications. For example, the devices could be used in angioplasty for the treatment of occluded blood vessels with tortuous or kinked paths, or where the vessels may be subject to deflection or deformation at or near the position of the stent. The stent could also be used for the repair of damaged blood vessels, for example in aortic grafting procedures or after perforation during a percutaneous procedure. In certain such cases, the intermediate portion of the device can allow the device to conform to the shape of the blood vessel and to deform in response to movement of the vessel with reduced risk of fatigue failure while remaining fixed or anchored in position by the end portions. For another example, the devices could be used to form a shunt between a healthy artery and a healthy vein for dialysis access and/or access for administration of medications (e.g., intermittent injection of cancer therapy, which can damage vessels).

Referring again to FIGS. 4 and 7, blocking material 251 may be used to help inhibit or prevent reversal of arterial blood flow. As will now be described in further detail, additional or other methods and systems can be used to inhibit or prevent reversal of arterial blood flow, or, stated another way, to inhibit or prevent flow of arterial blood now flowing into the vein from flowing in the normal, pre-procedure direction of blood flow in the vein such that oxygenated blood bypasses downstream tissue such as the foot.

In the absence of treatment, Peripheral Vascular Disease (PVD) may progress to critical limb ischemia (CLI), which is characterized by profound chronic pain and extensive tissue loss that restricts revascularization options and frequently leads to amputation. CLI is estimated to have an incidence of approximately 50 to 100 per 100,000 per year, and is associated with mortality rates as high as 20% at 6 months after onset.

Interventional radiologists have been aggressively trying to treat CLI by attempting to open up chronic total occlusions (CTOs) or bypassing CTOs in the sub-intimal space using such products as the Medtronic Pioneer catheter, which tunnels a wire into the sub-intimal space proximal to the CTO and then attempts to re-enter the vessel distal to the occlusion.

Once a wire is in place, a user can optionally create a wider channel and then place a stent to provide a bypass conduit past the occlusion. Conventional approaches such as percutaneous transluminal angioplasty (PTA), stenting, and drug eluting balloons (DEB) to treat PAD can also or alternatively be used in CLI treatment if a wire is able to traverse the occlusion.

From the amputee-coalition.org website, the following are some statistics regarding the CLI problem:

There are nearly 2 million people living with limb loss in the United States.

Among those living with limb loss, the main causes are:
vascular disease (54%) (including diabetes and peripheral artery disease (PAD)),
trauma (45%), and
cancer (less than 2%).

Approximately 185,000 amputations occur in the United States each year.

Hospital costs associated with having a limb amputated totaled more than $6.5 billion in 2007.

Survival rates after an amputation vary based on a variety of factors. Those who have amputations due to vascular disease (including PAD and diabetes) face a 30-day mortality rate reported to be between 9% and 15% and a long-term survival rate of 60% at 1 year, 42% at 3 years, and 35%-45% at 5 years.

Nearly half of the people who lose a limb to dysvascular disease will die within 5 years. This is higher than the 5-year mortality rate experienced by people with colorectal, breast, and prostate cancer.

Of people with diabetes who have a lower-limb amputation, up to 55% will require amputation of the second leg within 2 to 3 years.

CLI has been surgically treated by open-leg venous arterialization since the early 1900's. Numerous small series of clinical trials have been published over the years using such an open-leg surgical approach, as summarized by a 2006 meta-analysis article by Lu et al. in the European Journal of Vascular and Endovascular Surgery, vol. 31, pp. 493-499, titled "Meta-analysis of the clinical effectiveness of venous arterialization for salvage of critically ischemic limbs." The article had the following results and conclusions:

Results:
A total of 56 studies were selected for comprehensive review. No randomized control trial (RCT) was identified. Seven patient series, comprising 228 patients, matched the selection criteria. Overall 1-year foot preservation was 71% (95% CI: 64%-77%) and 1-year secondary patency was 46% (95% CI: 39%-53%). The large majority of patients in whom major amputation was avoided experienced successful wound healing, disappearance of rest pain, and absence of serious complications.

Conclusions:
On the basis of limited evidence, venous arterialization may be considered as a viable alternative before major amputation is undertaken in patients with "inoperable" chronic critical leg ischemia.

Among other maladies as described herein, the methods and systems described herein may be used to create an ateriovenous (AV) fistula in the below-the-knee (BTK) vascular system using an endovascular, minimally invasive approach. Such methods may be appropriate for patients that (i) have a clinical diagnosis of symptomatic critical limb ischemia as defined by Rutherford 5 or 6 (severe ischemic ulcers or frank gangrene); (ii) have been assessed by a vascular surgeon and interventionist and it was determined that no surgical or endovascular treatment is possible; and/or (iii) are clearly indicated for major amputation.

In some embodiments, a system or kit optionally comprises one or more of the following components: a first ultrasound catheter (e.g., an arterial catheter, a launching catheter including a needle, etc.); a second ultrasound catheter (e.g., a venous catheter, a target catheter, etc.); and a prosthesis (e.g., a covered nitinol stent graft in a delivery system (e.g., a 7 Fr (approx. 2.3 mm) delivery system)). The system or kit optionally further comprises an ultrasound system, a control system (e.g., computer). Some users may already have an appropriate ultrasound system that can be connected to the ultrasound catheter(s). The catheters and prostheses described above may be used in the system or kit, and details of other, additional, and/or modified possible components are described below.

FIG. 14A is a schematic side cross-sectional view of an example embodiment of an ultrasound launching catheter 170 comprising a needle 172 (e.g., a first ultrasound catheter, an arterial catheter (e.g., if extending a needle from artery into vein), a venous catheter (e.g., if extending a needle from vein into artery)). The catheter 170 is placed into an artery with the needle 172 in a retracted state inside a lumen of the catheter 170. The catheter 170 can be tracked over a guidewire (e.g., a 0.014 inch (approx. 0.36 mm) guidewire) and/or placed through a sheath in the artery (e.g., a femoral artery), and advanced up to the point of the total occlusion of the artery (in the tibial artery). The catheter 170 includes a handle 174 that includes a pusher ring 176. Longitudinal or distal advancement of the pusher ring 176 can advance the needle 172 from out of a lumen of the catheter 170, out of the artery and into a vein, as described herein. Other advancement mechanisms for the needle 172 are also possible (e.g., rotational, motorized, etc.). Before, after, and/or during after advancing the needle 172, a guidewire (e.g., a 0.014 inch (approx. 0.36 mm) guidewire) can be placed through the needle 172 (e.g., as described with respect to the guidewire 14 of FIG. 3), and this guidewire can be referred to as a crossing wire.

FIG. 14B is an expanded schematic side cross-sectional view of a distal portion of the ultrasound launching catheter 170 of FIG. 14A within the circle 14B. Upon advancing or launching, the needle 172 extends radially outwardly from a lumen 173 of the catheter 170. In some embodiments, the lumen 173 ends proximal to the ultrasound transmitting device 178. The needle 172 may extend along a path that is aligned with (e.g., parallel to) the path of the directional ultrasound signal emitted by the ultrasound transmitting device 178. FIG. 14B also shows the lumen 175, which can be used to house a guidewire for tracking the catheter 170 to the desired position.

Figure 15A:
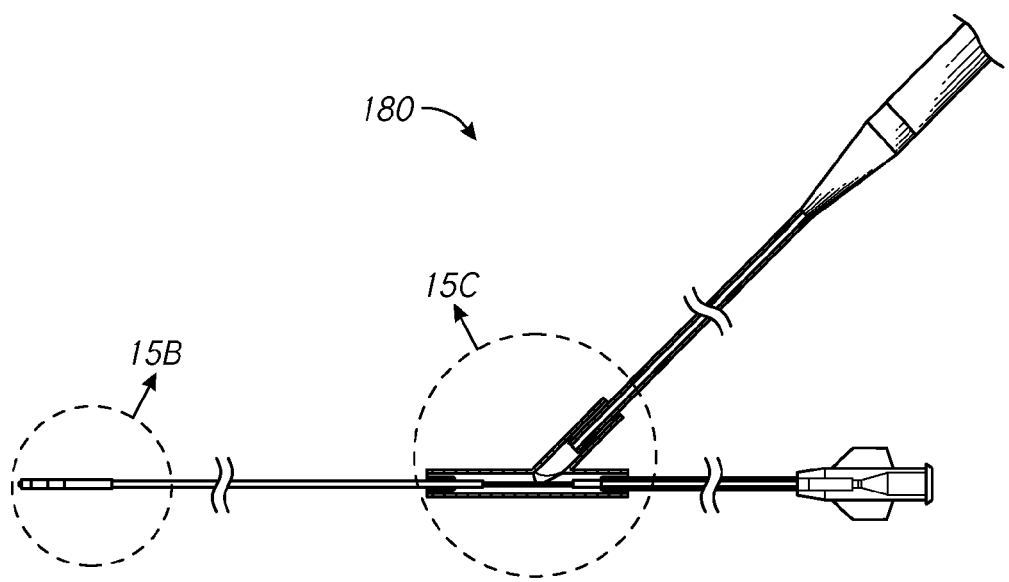
FIG. 15A is a schematic side elevational view of an example embodiment of an ultrasound target catheter.
Figure 15B:
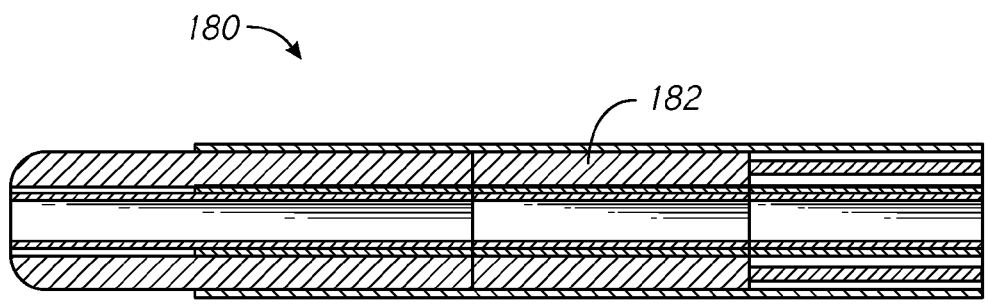
FIG. 15B is an expanded schematic side cross-sectional view of the ultrasound target catheter of FIG. 15A within the circle 15B.
Figure 15C:
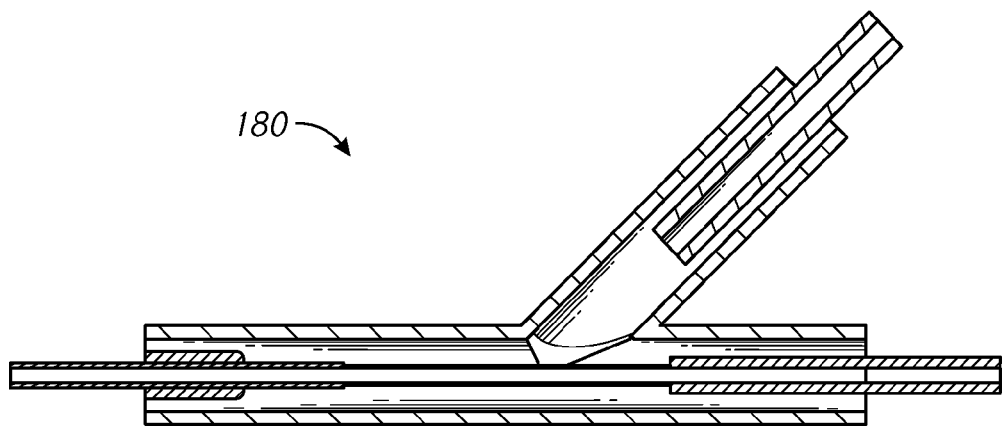
FIG. 15C is an expanded schematic side cross-sectional view of the ultrasound target catheter of FIG. 15A within the circle 15C.

FIG. 15A is a schematic side elevational view of an example embodiment of an ultrasound target catheter 180 (e.g., a second ultrasound catheter, an arterial catheter (e.g., if extending a needle from vein into artery), a venous catheter (e.g., if extending a needle from artery into vein)). FIG. 15B is an expanded schematic side cross-sectional view of the ultrasound target catheter 180 of FIG. 15A within the circle 15B. FIG. 15C is an expanded schematic side cross-sectional view of the ultrasound target catheter 180 of FIG. 15A within the circle 15C. The catheter 180 can be tracked over a guidewire (e.g., a 0.014 inch (approx. 0.36 mm) guidewire) and/or placed through a sheath in the vein (e.g., a femoral vein), and advanced up to a point (e.g., in the tibial vein) proximate and/or parallel to the distal end of the catheter 170 and/or the occlusion in the artery. The catheter 180 includes an ultrasound receiving transducer 182 (e.g., an omnidirectional ultrasound receiving transducer) that can act as a target in the vein for aligning the needle 172 of the catheter 170. The catheter 180 may be left in place or remain stationary or substantially stationary while the catheter 170 is rotated and moved longitudinally to obtain a good or optimal ultrasound signal indicating that the needle 172 is aligned with and in the direction of the catheter 180.

The catheters 170, 180 may be connected to an ultrasound transceiver that is connected to and controlled by a computer running transceiver software. As described in further detail herein, the catheter 170 includes a flat or directional ultrasound transmitter 178 configured to transmit an ultrasound signal having a low angular spread or tight beam (e.g., small beam width) in the direction of the path of the needle 172 upon advancement from the lumen 173 of the catheter 170. The catheter 180 includes an omnidirectional (360 degrees) ultrasound receiver 182 configured to act as a target for the ultrasound signal emitted by the directional transmitter 178 of the catheter 170. The catheter 170 is rotated until the peak ultrasound signal is displayed, indicating that the needle 172 is aligned to the catheter 180 such that, upon extension of the needle 172 (e.g., by longitudinally advancing the ring 176 of the handle 174), the needle 172 can pass out of the artery in which the catheter 170 resides, through interstitial tissue, and into the vein in which the catheter 180 resides.

Figure 16:
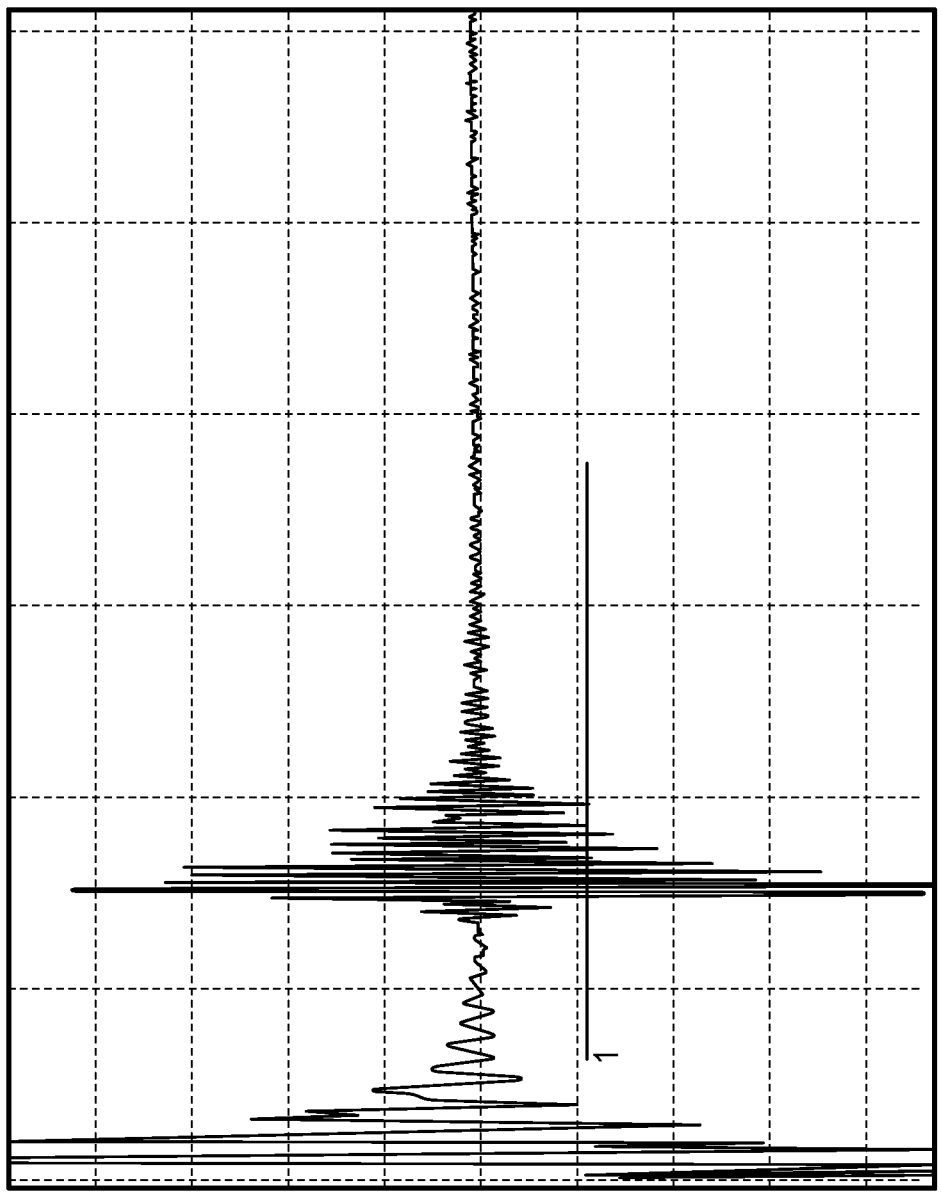
FIG. 16 is an example embodiment of a graph for detecting catheter alignment.

FIG. 16 is an example embodiment of a graph for detecting catheter alignment, as may be displayed on display device of an ultrasound system (e.g., the screen of a laptop, tablet computer, smartphone, combinations thereof, and the like). The graph in FIG. 16 shows that the signal originating from the transmitting catheter in the artery has been received by the receiving catheter in the vein. The second frequency envelope from the right is the received signal. The distance from the left side of the illustrated screen to the leading edge of the second frequency envelope may indicate the distance between the catheters. The operator can move the catheter in the artery both rotationally and longitudinally, for example until the second envelope is maximal, which indicates the catheters are correctly orientated.

Figure 17:
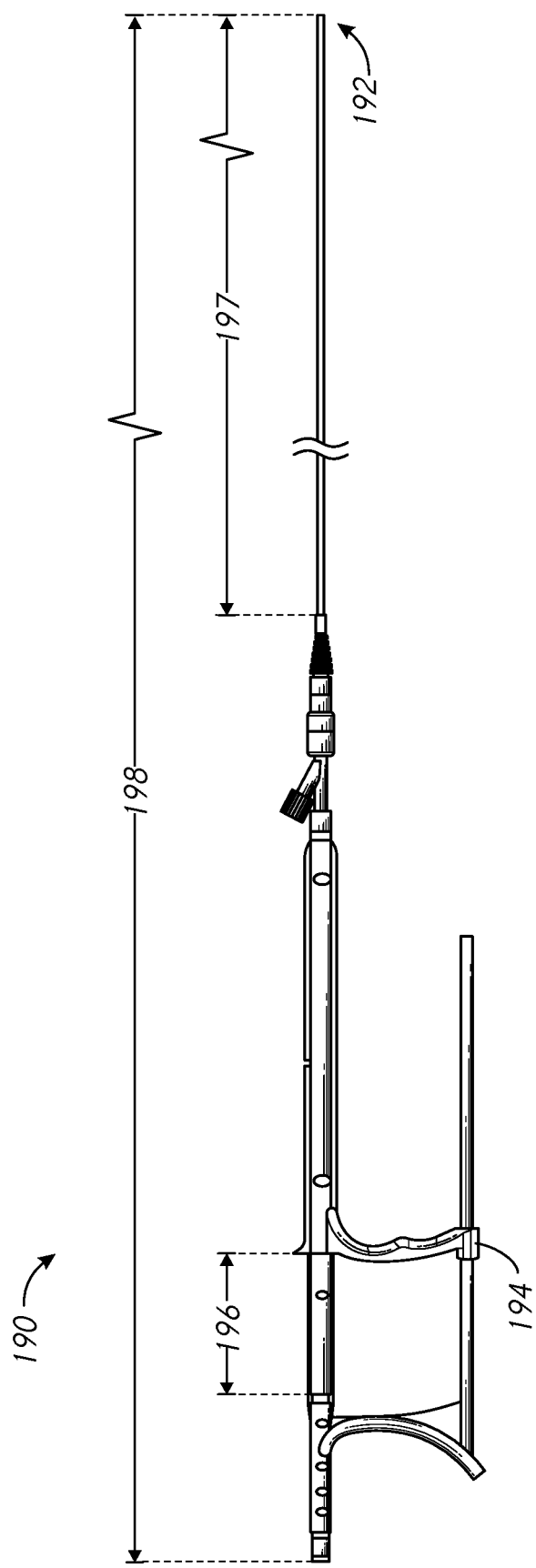
FIG. 17 is a schematic side elevational view of an example embodiment of a prosthesis delivery system.
Figure 18:
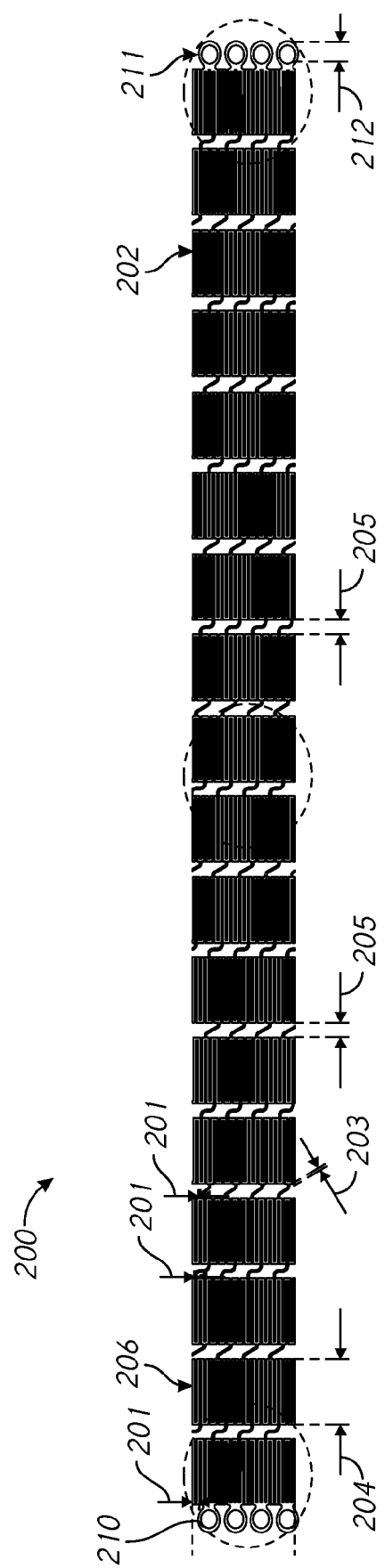
FIG. 18 is a schematic side elevational view of an example embodiment of a prosthesis.

FIG. 17 is a schematic side elevational view of an example embodiment of a prosthesis (e.g., stent, stent-graft) delivery system 190. In some embodiments, the delivery system 190 is a 7 Fr (approx. 2.3 mm) delivery system. FIG. 18 is a schematic side elevational view of an example embodiment of a prosthesis (e.g., stent, stent-graft) 200. In FIG. 17, a prosthesis (e.g., the prosthesis 200, other prostheses described herein, etc.) is in a compressed or crimped state proximate to the distal end 192 of the delivery system 190. In some embodiments, the prosthesis 200 comprises a shape-memory stent covered with a graft material, for example as described above. Once the crossing wire extends from the artery to the vein, for example as a result of being advanced through the needle 172 as described herein, the delivery system 190 can be advanced over the crossing wire. The prosthesis 200 may be deployed from the delivery system 190, for example by squeezing the trigger handle 194 of the delivery system 190, causing the outer cover sheath to proximally retract and/or distally advance the prosthesis 200. The prosthesis 200 can create a flow path between the artery and the vein and through the interstitial tissue. Other types of delivery systems and prostheses are also possible.

Referring again to FIG. 17, some non-limiting example dimensions of the delivery system 190 are provided. The distance 196 of travel of the trigger handle 194 may be, for example, between about 0.4 inches (approx. 1 cm) and about 12 inches (approx. 30 cm), between about 1 inch (approx. 2.5 cm) and about 8 inches (approx. 20 mm), or between about 2 inches (approx. 5 cm) and about 6 inches (approx. 15 mm) (e.g., about 2 inches (approx. 5 cm)). In some embodiments, the distance 196 of travel of the trigger handle 194 is at least as long as the length of the prosthesis 200 to be deployed (e.g., in the radially expanded state). In some embodiments, gearing or other mechanisms may be employed to reduce the distance 196 of travel of the trigger handle 194 be less than the length of the prosthesis 200 to be deployed (e.g., in the radially expanded state). The distance 196 may be adjusted for example, based on at least one of: the length of the prosthesis 200 to be deployed, the degree of foreshortening of the prosthesis 200 to be deployed, the mechanism of deployment (e.g., whether the outer sheath is proximally retracted, the prosthesis 200 is pushed distally forward, or both, whether the delivery system 190 includes gearing mechanism, etc.), combinations thereof, and the like. The length 197 of the outer sheath or catheter portion may be, for example, between about 40 inches (approx. 1,020 mm) and about 50 inches (approx. 1,270 mm), between about 46 inches (approx. 1,170 mm) and about 47 inches (approx. 1,190 mm), or between about 46.48 inches (approx. 1,180 mm) and about 46.7 inches (approx. 1,186 mm). The total length 198 of the delivery system 190 from proximal tip to distal tip may be, for example, between about 40 inches (approx. 1,000 mm) and about 60 inches (approx. 1,500 mm). The lengths 197, 198 may be adjusted, for example based on at least one of: length of the prosthesis 200 to be deployed, the degree of foreshortening of the prosthesis 200 to be deployed, the height of the patient, the location of the occlusion being treated, combinations thereof, and the like. In some embodiments, spacing the trigger handle 194 from the vascular access point, for example by between about 10 cm and about 30 cm (e.g., at least about 20 cm) may advantageously provide easier handling or management by the user. In certain such embodiments, the length 197 may be between about 120 cm and about 130 cm (e.g., for an antegrade approach) or between about 150 cm and about 180 cm (e.g., for a contralateral approach).

Referring again to FIG. 18, some non-limiting example dimensions of the prosthesis 200 are provided, depending on context at least in the compressed state. The thickness 201 of a structural strut may be, for example, between about 0.05 mm and about 0.5 mm or between about 0.1 mm and about 0.2 mm (e.g., about 0.143 mm). The spacing 202 between struts of a structural strut may be, for example, between about 0.005 mm and about 0.05 mm or between about 0.01 mm and about 0.03 mm (e.g., about 0.025 mm). The thickness 203 of a linking strut may be, for example, between about 0.05 mm and about 0.5 mm or between about 0.1 mm and about 0.2 mm (e.g., about 0.133 mm). The longitudinal length 204 of the structural components may be, for example, between about 1 mm and about 5 mm or between about 2.5 mm and about 3 mm (e.g., about 2.8 mm). The longitudinal length 205 between structural components may be, for example, between about 0.25 mm and about 1 mm or between about 0.5 mm and about 0.6 mm (e.g., about 0.565 mm). The length 206 of a strut within a structural component, including all portions winding back and forth, may be, for example, between about 25 mm and about 100 mm or between about 65 mm and about 70 mm (e.g., about 67.62 mm). The total longitudinal length of the prosthesis 200 may be, for example, between about 25 mm and about 150 mm or between about 50 mm and about 70 mm (e.g., about 62 mm). As described herein, a wide variety of laser-cut stents, woven stents, and combinations thereof, including various dimensions, are possible. The struts described herein may comprise wires or filaments or portions not cut from a hypotube or sheet.

The proximal and/or distal ends of the prosthesis 200 may optionally comprise rings 210. The rings 210 may, for example, help to anchor the prosthesis 200 in the artery and/or the vein. The circumferential width 211 of a ring 210 may be, for example, between about 0.25 mm and about 1 mm or between about 0.5 mm and about 0.75 mm (e.g., about 0.63 mm). The longitudinal length 212 of a ring 210 may be, for example, between about 0.25 mm and about 2 mm or between about 0.5 mm and about 1 mm (e.g., about 0.785 mm). In some embodiments, a ratio of the total length of the prosthesis 200 to the longitudinal length 212 of a ring 210 may be between about 50:1 and about 100:1 (e.g., about 79:1). The dimensions 211, 212 of the rings 210 may be adjusted, for example based on at least one of: strut thickness, diameter of the prosthesis (e.g., relative to the vessel), total length of the prosthesis, material, shape setting properties, combinations thereof, and the like.

Figure 19:
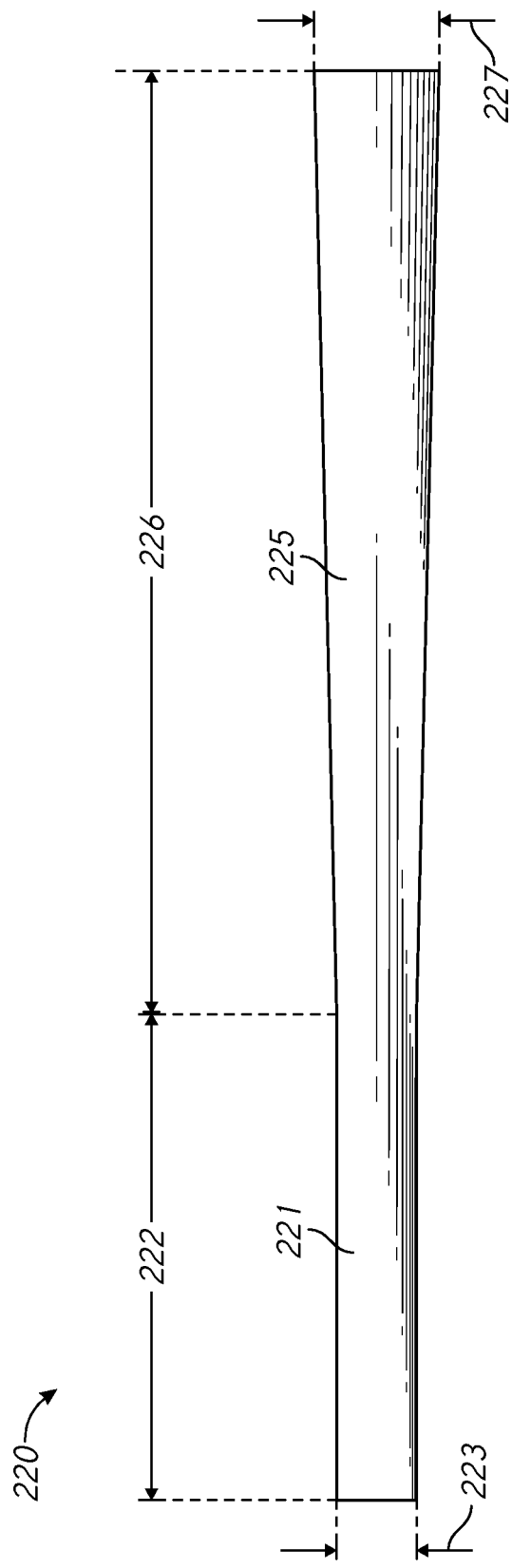
FIG. 19 is a schematic side elevational view of another example embodiment of a prosthesis.

FIG. 19 is a schematic side elevational view of another example embodiment of a prosthesis 220. The prosthesis 200 may have the shape of the prosthesis 220, for example in a radially expanded state (e.g., upon being deployed from the delivery system 190). FIG. 19 illustrates an example shape of the prosthesis 220 comprising a first portion 221 and a second portion 225. The first portion 221 has a substantially cylindrical or cylindrical shape having a length 222 between about 15 mm and about 25 mm (e.g., about 21 mm) and a diameter 223 between about 2.5 mm and about 5 mm (e.g., about 3.5 mm). The second portion 225 has a substantially frustoconical or frustoconical shape having a length 226 between about 30 mm and about 50 mm (e.g., about 41 mm) and a widest diameter 227 between about 4 mm and about 10 mm, between about 4 mm and about 7 mm (e.g., about 5.5 mm), etc. The angle of taper of the second portion 225 away from the first portion 221 may be between about 0.02 degrees and about 0.03 degrees (e.g., about 0.024 degrees).

Further details regarding prostheses that can be used in accordance with the methods and systems described herein are described in U.S. patent application Ser. No. 13/791,185, filed Mar. 8, 2013, which is hereby incorporated by reference in its entirety.

FIGS. 20A-20H schematically illustrate an example embodiment of a method for effecting retroperfusion. The procedure will be described with respect to a peripheral vascular system such as the lower leg, but can also be adapted as appropriate for other body lumens (e.g., cardiac, other peripheral, etc.). Certain steps such as anesthesia, incision specifics, suturing, and the like may be omitted for clarity. In some embodiments, the procedure can be performed from vein to artery (e.g., with the venous catheter coming from below).

Access to a femoral artery and a femoral vein is obtained. An introducer sheath (e.g., 7 Fr (approx. 2.3 mm)) is inserted into the femoral artery and an introducer sheath (e.g., 6 Fr (approx. 2 mm)) is inserted into the femoral vein, for example using the Seldinger technique. A guidewire (e.g., 0.014 inch (approx. 0.36 mm), 0.035 inch (approx. 0.89 mm), 0.038 inch (approx. 0.97 mm)) is inserted through the introducer sheath in the femoral artery and guided into the distal portion of the posterior or anterior tibial diseased artery 300. A second guidewire (e.g., 0.014 inch (approx. 0.36 mm), 0.035 inch (approx. 0.89 mm), 0.038 inch (approx. 0.97 mm)) or a snare is inserted through the introducer sheath in the femoral vein. In embodiments in which a snare is used, the described third guidewire, fourth guidewire, etc. described herein are accurate even though the numbering may not be sequential.

A venous access needle is percutaneously inserted into a target vein, for example a tibial vein (e.g., the proximal tibial vein (PTV)). In some embodiments, the venous access needle may be guided under ultrasound. In some embodiments, contrast may be injected into the saphenous vein towards the foot (retrograde), and then the contrast will flow into the PTV. This flow path can be captured using fluoroscopy such that the venous access needle can be guided by fluoroscopy rather than or in addition to ultrasound.

Figure 20D:
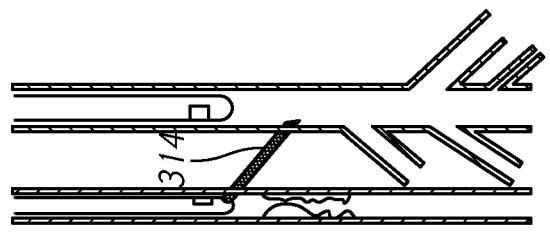
FIGS. 20A-20H schematically illustrate an example embodiment of a method for effecting retroperfusion.
Figure 20C:
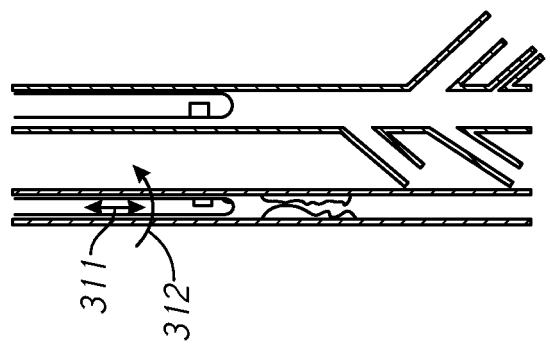

The target vein may be accessed proximate to and distal to (e.g., a few inches or centimeters) below where the launching catheter 310 will likely reside. In some embodiments, the target vein may be in the ankle. Once the venous access needle is in the vein, a third guidewire (or "second" guidewire in the case that a snare is used instead of a second guidewire) is inserted into the venous access needle and advanced antegrade in the target vein up to the femoral vein. This access method can advantageously reduce issues due to advancing wires retrograde across venous valves, which are described in further detail below. The third guidewire is snared, for example using fluoroscopic guidance, and pulled through the femoral vein sheath. The target catheter 320 is inserted into the femoral vein sheath over the third guidewire, which has been snared. The target catheter 320 is advanced over the third guidewire into the venous system until the target catheter is proximate to and/or parallel with the guidewire in the distal portion of the posterior or anterior tibial diseased artery and/or proximate to the occlusion 304, as shown in FIG. 20A.

In some embodiments, the third guidewire may include an ultrasound receiving transducer (e.g., omnidirectional) mounted to provide the target for the signal emitted by the launching catheter 310 or the target catheter 320 could be tracked over the third guidewire, either of which may allow omission of certain techniques (e.g., femoral vein access, introducing vein introducer sheath, inserting second guidewire, antegrade advancing of the third guidewire up to the femoral vein, snaring the third guidewire, advancing the target catheter 320 over the third guidewire).

In some embodiments, the PTV may be accessed directly, for example using ultrasound, which can allow placement of the target catheter 320 directly into the PTV, for example using a small sheath. which may allow omission of certain techniques (e.g., femoral vein access, introducing vein introducer sheath, inserting second guidewire, antegrade advancing of the third guidewire up to the femoral vein).

In some embodiments, the catheter 320 is not an over-the-wire catheter, but comprises a guidewire and an ultrasound receiving transducer (e.g., omnidirectional). The catheter 320 may be inserted as the third guidewire, as discussed above, as the second guidewire, or as a guidewire through a small sheath when directly accessing the PTV.

Figure 21:
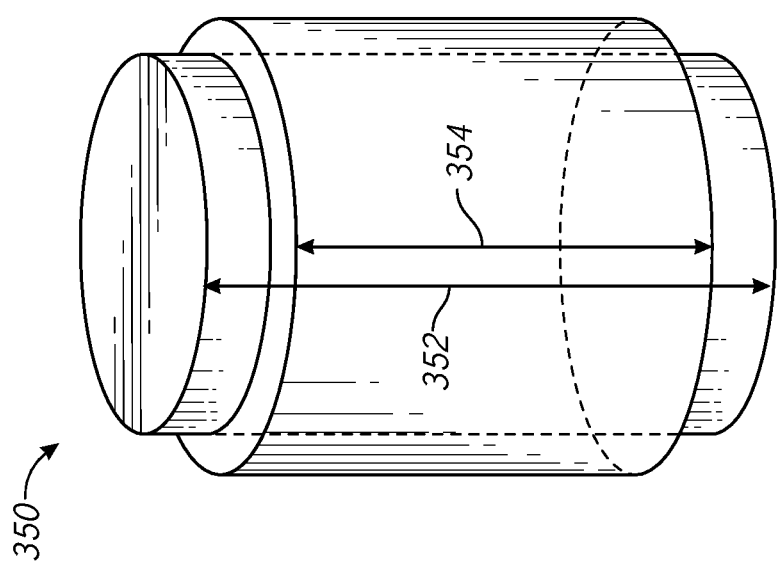
FIG. 21 is a schematic perspective view of an example embodiment of an ultrasound receiving transducer.

Ultrasound transducers generally include two electrodes including surfaces spaced by a ceramic that can vibrate. An incoming or received ultrasound signal wave can couple into a length extensional mode, as shown in FIG. 21. FIG. 21 is a schematic perspective view of an example embodiment of an ultrasound receiving transducer 350. If the proximal or top end 352 of the transducer 350 and the distal or bottom end 354 of the transducer are conductive and electrically connected to wires, the transducer can receive ultrasound signals. In some embodiments, the transducer 350 has a length 356 between about 0.1 mm and about 0.4 mm (e.g., about 0.25 mm). In some embodiments, the transducer 350 has an overlap length 358 between about 0.1 mm and about 0.3 mm (e.g., about 0.2 mm). In some embodiments, the transducer 350 has a diameter that is similar to, substantially similar to, or the same as the guidewire on which it is mounted. In some embodiments, an array or series of laminates may enhance the signal-receiving ability of the transducer 350.

Figure 22:
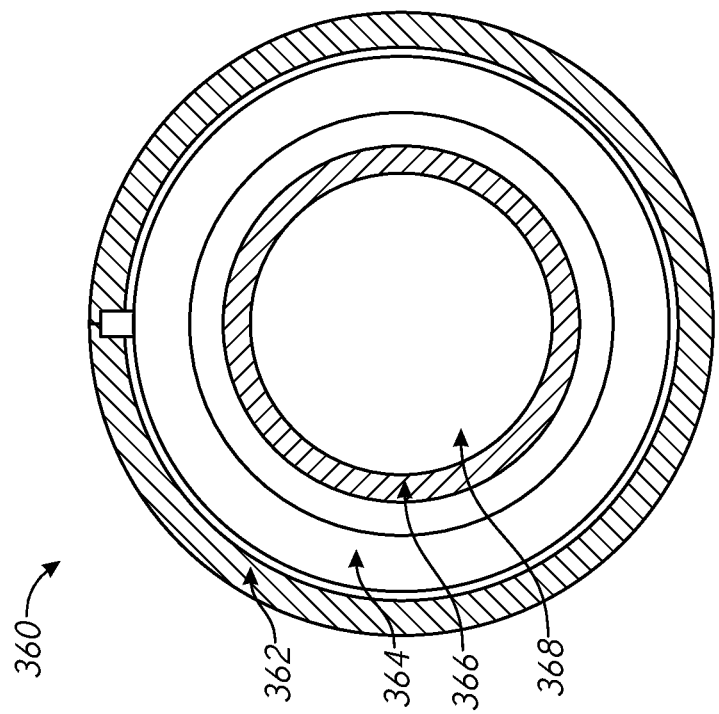
FIG. 22 is a schematic cross-sectional view of another example embodiment of an ultrasound receiving transducer.

In some embodiments, a guidewire comprising an ultrasound receiving transducer may comprise a piezoelectric film (e.g., comprising plastic), which could enhance the signal-receiving ability of the transducer. FIG. 22 is a schematic cross-sectional view of another example embodiment of an ultrasound receiving transducer 360. The ultrasound receiving transducer 360 shown in FIG. 22 includes an optional lumen 368. The ultrasound receiving transducer 360 includes a series of layers 362, 364, 366. The layer 362 may comprise a polymer (e.g., polyvinylidene fluoride (PVDF)) layer. The layer 364 may comprise an inorganic compound (e.g., tungsten carbide) layer. The layer 366 may comprise a polymer (e.g., polyimide) layer. The layer 366 may have a thickness between about 25 micrometers (μm or microns) and about 250 μm (e.g., at least about 50 μm).

Figure 20B:
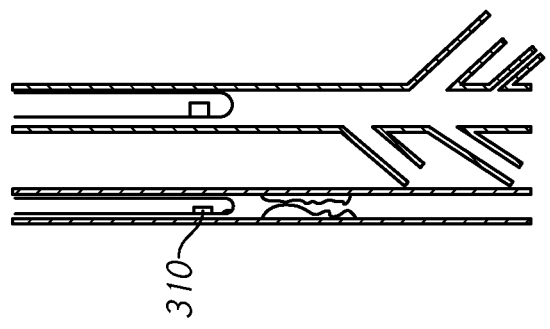
Figure 20A:
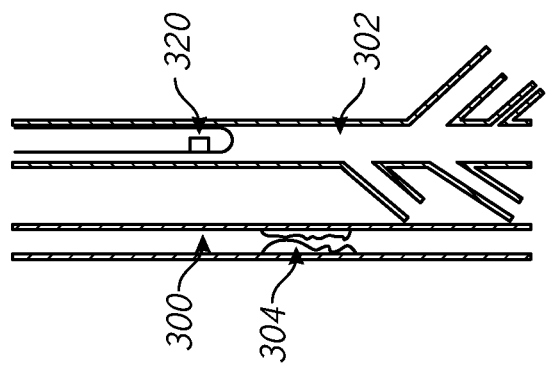

The launching catheter 310 is tracked over the guidewire in the femoral and tibial arteries proximate to and proximal to the occlusion 304, as shown in FIG. 20B. The catheter 310 may be more proximal to the occlusion 304 depending on suitability at that portion of the anatomy for the retroperfusion process. In some embodiments, the catheter 310 may be positioned in the distal portion of the posterior or anterior tibial artery, for example proximate to the catheter 320. In some embodiments, the catheter 310 may be positioned within a few inches or centimeters of the ankle.

The launching catheter 310 emits a directional ultrasound signal. As shown by the arrow 311, 312 in FIG. 20C, the launching catheter 310 is rotated and moved longitudinally until the signal is received by the target catheter 320. Once the signal is received, which indicates alignment such that extension of the needle form the launching catheter 310 will result in successful access of the vein, a crossing needle 314 is advance out of the catheter 310, out of the tibial artery 300 and into the tibial vein 302, as shown in FIG. 20D. Accuracy of the placement of the crossing needle 314 to form a fistula between the artery 300 and the vein 302 may be confirmed, for example, using contrast and fluoroscopy.

In some embodiments, the ultrasound signal can be used to determine the distance between the artery 300 and the vein 302. Referring again to FIG. 16, the distance from the left side of the illustrated screen to the leading edge of the second frequency envelope can be used as an indicator of distance between the catheters.

Referring again to FIG. 16, a display device may graphically show signal alignment peaks to allow the user to determine the alignment position. In some embodiments, the signal alignment may change color above or below a threshold value, for example from red to green. In some embodiments, an audio signal may be emitted, for example when an alignment signal crosses over a threshold value, which can allow a user to maintain focus on the patient rather than substantially continuously monitoring a screen.

In some embodiments, a horizontal line on the screen may move up to indicate the maximum signal value or peak achieved to that point during the procedure. This line may be called "peak hold." If a greater signal value is achieved, the horizontal line moves to match that higher value. If no manipulation is able to raise the peak above the horizontal line, that can indicate maximum alignment. If the signal peak falls a certain amount below the horizontal line, the catheters may have moved and no longer be properly aligned. Since the level of alignment indicated by the horizontal line has previously been achieved during the procedure, the user knows that such a level of alignment can be achieved by further rotational and/or longitudinal manipulation.

Figure 20H:
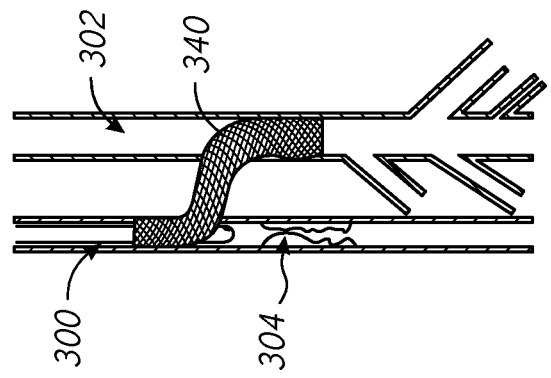
Figure 20G:
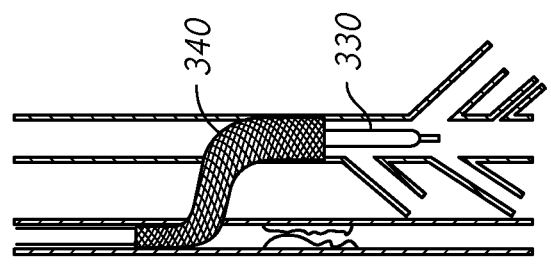
Figure 20F:
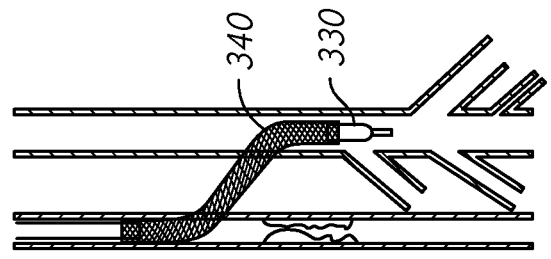
Figure 20E:
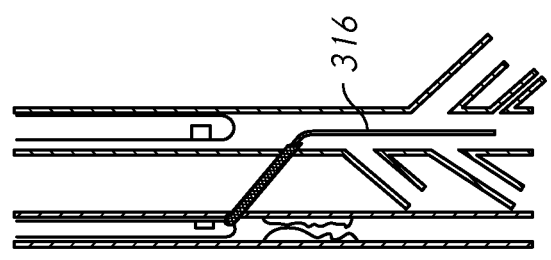

A fourth guidewire 316 (e.g., 0.014 inch (approx. 0.36 mm)) (or "third" guidewire in the case that a snare is used instead of a second guidewire) is placed through the lumen of the crossing needle 314 of the catheter 310 and into the tibial vein 302 in a retrograde direction (of the vein 302) towards the foot, as shown in FIG. 20E. External cuff pressure may be applied above the needle crossing point to reduce flow in the artery 300 to inhibit or prevent formation of a hematoma, and/or to engorge the vein to facilitate valve crossing. The catheters 310, 320 may be removed, leaving the guidewire 316 in place, extending from the introducer sheath in the femoral artery, through the arterial tree, and into the tibial vein 302.

Certain techniques for crossing a guidewire 316 from an artery 300 to a vein 302 may be used instead of or in addition to the directional ultrasound techniques described herein.

In some embodiments, a tourniquet can be applied to the leg, which can increase vein diameters. In some embodiments, a blocking agent (e.g., as discussed with respect to FIGS. 4 and 7, a blocking balloon, etc.) may be used to increase vein diameter. For example, venous flow could back up, causing dilation of the vein. A larger vein diameter can produce a larger target for the crossing needle 314, making the vein 300 easier to access with the crossing needle 314.

In some embodiments, a PTA balloon can be used in the target vein, and a needle catheter (e.g., Outback, available from Cordis) can target the PTA balloon under fluoroscopy. The crossing needle 314 can puncture the PTA balloon, and the reduction in pressure of the PTA balloon can confirm proper alignment of the crossing needle 314. The PTA balloon can increase vein diameter, producing a larger target for the crossing needle 314, making the vein 300 easier to access with the crossing needle 314. The guidewire 316 may be advanced through the crossing needle 314 and into the PTA balloon.

In some embodiments, the PTA balloon comprises a mesh (e.g., a woven mesh), for example embedded in the polymer of the balloon. When a balloon without such a mesh is punctured, the balloon material could rupture and cause emboli (e.g., pieces of the balloon floating downstream). The mesh can help to limit tearing of the balloon material, which can inhibit or prevent balloon material from causing emboli.

In some embodiments, two PTA balloons spaced longitudinally along the axis of the catheter can be used in the target vein, and a needle catheter can target the one of the PTA balloons. Upon puncturing of one of the PTA balloons by the crossing needle 314, contrast in a well between the PTA balloons can be released because the punctured balloon no longer acts as a dam for the contrast. The release of contrast can be monitored using fluoroscopy. The PTA balloons can be on the same catheter or on different catheters.

In some embodiments, two PTA balloons spaced longitudinally along the axis of the catheter can be used in the target vein, and a needle catheter can target the space or well between the PTA balloons. Upon puncturing of the well by the crossing needle 314, contrast in the well can be disturbed. The disturbance of contrast can be monitored using fluoroscopy. The PTA balloons can be on the same catheter or on different catheters.

In some embodiments in which a PTA balloon may be used in combination with an ultrasound target in the target vein, a PTA balloon catheter includes a PTA balloon and an ultrasound receiving transducer (e.g., omnidirectional). In certain such embodiments, the launching catheter 310 can target the PTA balloon under fluoroscopy and/or can target the ultrasound receiving transducer as described herein. The crossing needle 314 can puncture the PTA balloon, and the reduction in pressure of the PTA balloon can confirm proper alignment of the crossing needle 314. The PTA balloon can increase vein diameter, producing a larger target for the crossing needle 314, making the vein 300 easier to access with the crossing needle 314. The guidewire 316 may be advanced through the crossing needle 314 and into the PTA balloon.

In some embodiments, a LeMaitre device (e.g., the UnBalloon™ Non-Occlusive Modeling Catheter, available from LeMaitre Vascular of Burlington, Mass.) can be used in the target vein. In some embodiments, a LeMaitre device can increase vein diameters. A larger vein diameter can produce a larger target for the crossing needle 314, making the vein 300 easier to access with the crossing needle 314. In some embodiments, the needle 314 can penetrate into the LeMaitre device. In certain such embodiments, the LeMaitre device can act as a mesh target (e.g., comprising radiopaque material visible under fluoroscopy) for the crossing needle 314. The mesh of the LeMaitre device can be radially expanded by distally advancing a proximal portion of the mesh and/or proximally retracting a distal portion of the mesh (e.g., pushing the ends together like an umbrella) and/or by allowing the mesh to self-expand (e.g., in embodiments in which at least some parts of the mesh comprise shape-memory material). In some embodiments, a LeMaitre device can grip a crossing wire to hold the crossing wire in the target vein as the LeMaitre device closes.

In some embodiments, the launching catheter 310 may comprise a first magnet having a first polarity and the target catheter 320 may comprise a second magnet having a second polarity. When the magnets are close enough for magnetic forces to move one or both of the catheters 310, 320, the crossing needle 314 may be advanced to create the fistula between the artery 300 and the vein 302. In some embodiments, the first magnet maybe circumferentially aligned with the crossing needle 314 and/or the launching catheter 310 may be magnetically shielded to provide rotational alignment. In some embodiments, the second magnet may be longitudinally relatively thin to provide longitudinal alignment. In some embodiments, the crossing needle 314 and/or the guidewire 316 may be magnetically pulled from the artery 300 to the vein 302, or vice versa. Some systems may include both ultrasound guidance and magnetic guidance. For example, ultrasound guidance could be used for initial alignment and magnetic guidance could be used for refined alignment.

Referring again to FIGS. 20A-20H, a prosthesis delivery system 330 carrying a prosthesis 340 is tracked over the guidewire 316 through the interstitial space between the artery 300 and the vein 300 and then into the vein 300, as shown in FIG. 20F. In some embodiments, a separate PTA balloon catheter (e.g., about 2 mm) can be tracked over the guidewire 316 to pre-dilate the fistula between the artery 300 and the vein 302 prior to introduction of the prosthesis delivery system 330. Use of a PTA balloon catheter may depend, for example, on the radial strength of the prosthesis 340.

The prosthesis 340 is deployed from the prosthesis delivery system 330, for example by operating a trigger handle 194 (FIG. 17). In some embodiments, for example if the prosthesis 340 is not able to expand and/or advance, the prosthesis delivery system 330 may be removed and a PTA catheter (e.g., about 2 mm) advanced over the guidewire 316 to attempt to dilate or further dilate the fistula the artery 300 and the vein 302. Deployment of the prosthesis 340 may then be reattempted (e.g., by self-expansion, balloon expansion, etc.). In some embodiments, deployment of the prosthesis 340 may remodel a vessel, for example expanding the diameter of the vessel by at least about 10%, by at least about 20%, by at least about 30%, or more, by between about 0% and about 10%, by between about 0% and about 20%, by between about 0% and about 30%, or more. In embodiments in which the prosthesis 340 is self-expanding, the degree of remodeling may change over time, for example the prosthesis 340 expanding as the vessel expands or contracting when the vessel contracts.

Once the prosthesis 340 is deployed, as shown in FIG. 20G, the fistula may be dilated with a PTA catheter. The diameter of the PTA catheter (e.g., about 3 mm to about 6 mm) may be selected based at least in part on: the diameter of the artery 300, the diameter of the vein 302, the composition of the interstitial tissue, the characteristics of the prosthesis 340, combinations thereof, and the like. In some embodiments, the prosthesis delivery system 330 may comprise a PTA balloon catheter (e.g., proximal or distal to the prosthesis 340) usable for one, several, or all of the optional PTA balloon catheter techniques described herein. In embodiments in which the prosthesis comprises a conical portion, the PTA balloon may comprise a conical portion. Once the prosthesis 340 is in place, the prosthesis delivery system 330 may be removed, as shown in FIG. 20H. An AV fistula is thereby formed between the artery 300 and the vein 302. Confirmation of placement of various catheters 310, 320, 330 and the prosthesis 340 may be confirmed throughout parts or the entire procedure under fluoroscopy using contrast injections.

In some embodiments, a marker (e.g., a clip a lancet, scissors, a pencil, etc.) may be applied (e.g., adhered, placed on top of, etc.) to the skin to approximately mark the location of the fistula formed between the artery 300 and the vein 302 by the crossing needle 314 prior to deployment of the prosthesis 340. In embodiments in which the user uses a sphygmomanometer inflated above the fistula to avoid bleeding, the lack of blood flow can render visualization or even estimation of the fistula site difficult, and the marker can provide such identification. In embodiments in which the transmitting and receiving catheters are removed after fistula formation, the cross-over point may be difficult for the user to feel or determine, and the marker can provide such identification. If the fistula is to be dilated, a midpoint of the dilation balloon may be preferably aligned with the midpoint of the fistula (e.g., to increase or maximize the hole-through interstitial space). In some embodiments, the marker may be visualized under fluoroscopy (e.g., comprising radiopaque material) to allow the user to see and remember the location of the fistula under fluoroscopy prior to deployment of the prosthesis 340.

Once the prosthesis 340 is in place, an obstacle to blood flowing through the vein 302 and into the foot are the valves in the veins. Steering a guidewire across venous valves can be a challenge, for example because pressure from the artery may be insufficient to extend the veins and make the valves incompetent. The Applicant has discovered that venous valves distal to the AV fistula can be disabled or made incompetent using one or more of a variety of techniques such as PTA catheters, stents, and a valvulotome, as described in further detail below. Disabling venous valves can allow blood to flow via retroperfusion from the femoral artery, retrograde in the vein 302, and retrograde in the vein to the venuoles and capillaries to the distal part of the venous circulation of the foot to provide oxygenated blood to the foot in CLI patients.

In some embodiments, a high-pressure PTA balloon catheter may be used to make venous valves incompetent (e.g., when inflated to greater than about 10 atm (approx. 1,013 kPa)).

In some embodiments, one or more stents can be placed across one or more venous valves to render those valves incompetent. For example, such stents should have sufficient radial force that the valves stay open.

Figure 23A:
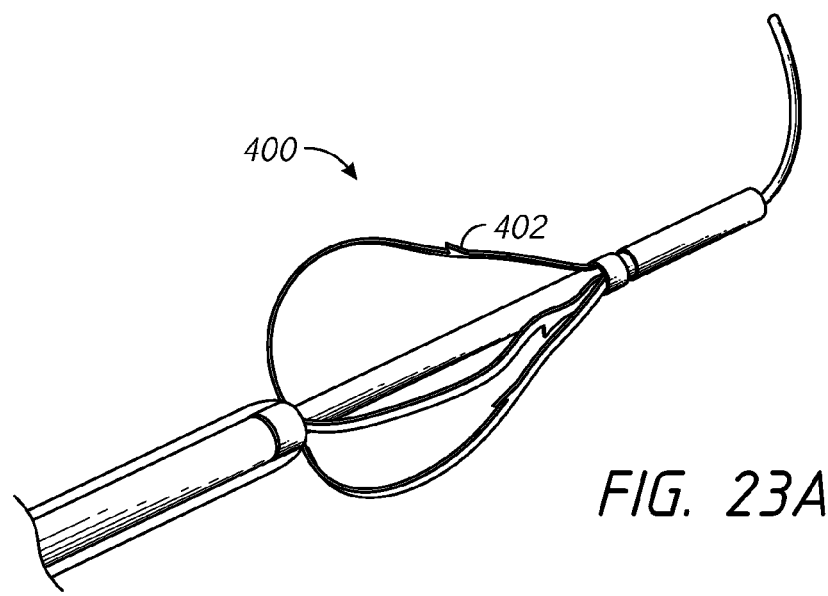
FIG. 23A is a schematic perspective view of an example embodiment of a valvulotome.

In some in situ bypass procedures, a saphenous vein is attached to an artery in the upper leg and another artery in the lower leg, bypassing all blockages in the artery. In certain such procedures, the vein is not stripped out of the patient, flipped lengthwise, and used as a prosthesis, but rather is left in place so that blood flow is retrograde (against the valves of the vein). A standard valvulotome may be placed into the saphenous vein from below and advanced to the top in a collapsed state, opened, and then pulled backwards in an open state, cutting venous valves along the way. Cutting surfaces of such valvulotomes face backwards so as to cut during retraction during these procedures. FIG. 23A is a schematic perspective view of an example embodiment of a valvulotome 400 that may be used with such procedures, including blades 402 facing proximally.

Figure 23B:
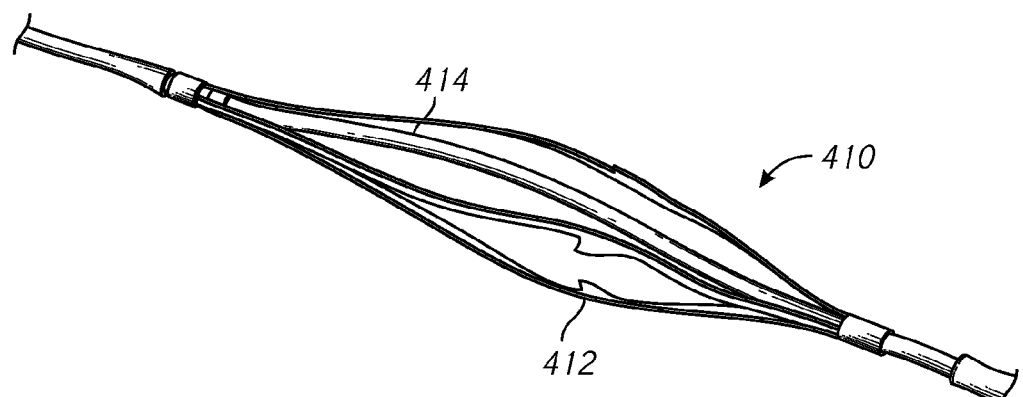
FIG. 23B is a schematic perspective view of an example embodiment of a reverse valvulotome.

In some embodiments of the methods described herein, access distal to the vein valves is not available such that pulling a valvulotome backwards is not possible, but pushing a reverse valvulotome as described herein forward is possible. FIG. 23B is a schematic perspective view of an example embodiment of a valvulotome 410 that may be used with such procedures. The reverse valvulotome 410 includes one or a plurality of blades 412 (e.g., two to five blades (e.g., three blades)) facing forward or distal such that valves can be cut as the reverse valvulotome 410 is advanced distally. At least because retrograde access to veins to be disabled has not previously been recognized as an issue, there has been no prior motivation to reverse the direction of the blades of a valvulotome to create a reverse vavlulotome 410 such as described herein. The reverse valvulotome 410 may be tracked over a guidewire 414, which can be steered into the veins, for making the venous valves incompetent. After forming a fistula between an artery and a vein as described herein, the flow of fluid in the vein is in the direction opposite the native or normal or pre-procedure direction of fluid flow in the vein such that pushing the reverse valvulotome 410 is in a direction opposite native fluid flow but in the direction of post-fistula fluid flow.

Other systems and methods are also possible for making the valves in the vein incompetent (e.g., cutting balloons, atherectomy, laser ablation, ultrasonic ablation, heating, radio frequency (RF) ablation, a catheter with a tip that is traumatic or not atraumatic (e.g., an introducer sheath) being advanced and/or retracted, combinations thereof, and the like).

Figure 24:
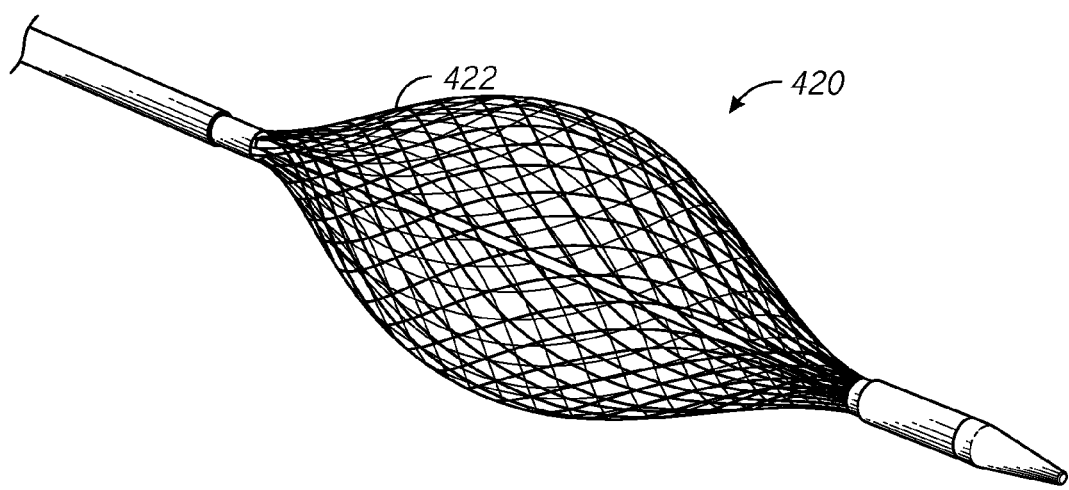
FIG. 24 is a schematic perspective view of an example embodiment of a LeMaitre device.

Crossing vein valves in a retrograde manner before such valves are made incompetent can also be challenging. FIG. 24 is a schematic perspective view of an example embodiment of a LeMaitre device 420 that may be used to radially expand the veins, and thus their valves. The LeMaitre device 420 includes an expandable oval or oblong leaf shape 422, for example a self-expanding nitinol mesh. In some embodiments, a PTA balloon catheter may be used to radially expand the veins, and thus their valves. In some embodiments, application of a tourniquet to the leg can radially expand the veins, and thus their valves. Upon radial expansion, a guidewire can be advanced through the stretched valve(s) (e.g., through an expansion device such as the LeMaitre device) and catheters (e.g., PTA, stent delivery, atherectomy, etc.) or other over-the-wire devices can be advanced over the guidewire.

Although some example embodiments have been disclosed herein in detail, this has been done by way of example and for the purposes of illustration only. The aforementioned embodiments are not intended to be limiting with respect to the scope of the appended claims, which follow. It is contemplated by the inventors that various substitutions, alterations, and modifications may be made to the invention without departing from the spirit and scope of the invention as defined by the claims.

While the devices described herein may be used in applications in which the fluid that flows through the device is a liquid such as blood, the devices could also or alternatively be used in applications such as tracheal or bronchial surgery where the fluid is a gas, such as air. In some embodiments, the fluid may contain solid matter, for example emboli or, in gastric surgery where the fluid includes food particles.

While the invention is susceptible to various modifications, and alternative forms, specific examples thereof have been shown in the drawings and are herein described in detail. It should be understood, however, that the invention is not to be limited to the particular forms or methods disclosed, but, to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "making valves in the first vessel incompetent" include "instructing making valves in the first vessel incompetent." The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 10 mm" includes "10 mm." Terms or phrases preceded by a term such as "substantially" include the recited term or phrase. For example, "substantially parallel" includes "parallel."

The following claims set forth several embodiments of the invention(s). These non-limiting claims identify certain permutations of combinations of features disclosed herein, although other permutations of combinations of features are also encompassed within the scope of the invention(s).

What is claimed is:

1. A method of diverting fluid flow from a first passage to a second passage to effect retroperfusion in the second passage, the method comprising:
    forming a fistula between the first passage and a second passage, the first passage comprising an artery and the second passage comprising a vein, wherein forming the fistula between the first passage and the second passage comprises identifying alignment of an ultrasound signal using alignment peaks on a display device;
    deploying a stent graft comprising a longitudinal portion having a frustoconical shape, wherein, after deploying the stent graft, a first portion of the stent graft is in the first passage, a second portion of the stent graft is in the second passage, and a third portion of the stent graft is in the fistula; and
    making a valve in the second passage incompetent to reduce inhibition of retroperfusion through the second passage by the valve, wherein making the valve in the second passage incompetent comprises advancing a reverse valvulotome in a direction opposite native fluid flow in the second passage, wherein, during advancing the reverse valvulotome, a blade of the reverse valvulotome disables the valve.

2. The method of claim 1, further comprising expanding the second passage and the valve in the second passage, wherein expanding the second passage and the valve in the second passage comprises at least one of:
    applying a tourniquet to a body part comprising the second passage;
    expanding a balloon in the second passage; and
    expanding a LeMaitre device in the second passage.

3. The method of claim 1, wherein making the valve in the second passage incompetent comprises deploying a stent across the valve.

4. A method of diverting fluid flow from a first passage to a second passage to effect retroperfusion in the second passage, the method comprising:
   forming a fistula between the first passage and a second passage;
   deploying a stent graft, wherein, after deploying the stent graft, a first portion of the stent graft is in the first passage, a second portion of the stent graft is in the second passage, and a third portion of the stent graft is in the fistula; and
   making a valve in the second passage incompetent to reduce inhibition of retroperfusion through the second passage by the valve, wherein making the valve in the second passage incompetent comprises advancing a reverse valvulotome in a direction opposite native fluid flow in the second passage, wherein, during advancing the reverse valvulotome, a blade of the reverse valvulotome disables the valve.

5. The method of claim 4, further comprising expanding the second passage, wherein expanding the second passage comprises at least one of:
   applying a tourniquet to a body part comprising the second passage;
   expanding a balloon in the second passage; and
   expanding a LeMaitre device in the second passage.

6. The method of claim 4, wherein making the valve in the second passage incompetent comprises deploying a stent across the valve.

7. The method of claim 4, wherein the reverse valvulotome comprises:
   a proximal portion;
   a distal portion; and
   a longitudinal axis between the proximal portion and the distal portion,
   wherein the distal portion comprises:
      a blade, the blade having a retracted position in which the blade is substantially parallel to the longitudinal axis and an expanded position in which the blade is substantially non-parallel to the longitudinal axis, the blade comprising a sharp surface facing distally and configured to at least partially disable the valve during advancing the reverse valvulotome in the direction opposite native fluid flow in the second passage.

8. The method of claim 4, wherein the stent graft comprises, in a radially expanded state:
   a first longitudinal segment comprising:
      a cylindrical shape,
      a first length, and
      a first diameter; and
   a second longitudinal segment adjacent to the first longitudinal segment, the second longitudinal segment comprising:
      a frustoconical shape,
      a second length longer than the first length,
      a narrowest diameter, and
      a widest diameter larger than the first diameter.

9. A method of diverting fluid flow from a first passage to a second passage to effect retroperfusion in the second passage, the method comprising:
   forming a fistula between the first passage and a second passage, wherein forming the fistula between the first passage and the second passage comprises dilating the fistula; and
   making a valve in the second passage incompetent to reduce inhibition of retroperfusion through the second passage by the valve, wherein making the valve in the second passage incompetent comprises deploying a stent across the valve,
   advancing a reverse valvulotome in a direction opposite native fluid flow in the second passage, wherein, during advancing the reverse valvulotome, a blade of the reverse valvulotome disables the valve.

10. The method of claim 9, wherein making the valves in the second passage incompetent comprises expanding the second passage, wherein expanding the second passage comprises at least one of:
   applying a tourniquet to a body part comprising the second passage;
   expanding a balloon in the second passage; and
   deploying at least one stent across the valves.

11. The method of claim 9, wherein making the valve in the second passage incompetent comprises deploying a stent across the valve.

12. The method of claim 9, wherein the reverse valvulotome comprises:
   a proximal portion;
   a distal portion; and
   a longitudinal axis between the proximal portion and the distal portion,
   wherein the distal portion comprises:
      a blade, the blade having a retracted position in which the blade is substantially parallel to the longitudinal axis and an expanded position in which the blade is substantially non-parallel to the longitudinal axis, the blade comprising a sharp surface facing distally and configured to at least partially disable the valve during distal advancement of the reverse valvulotome.

13. The method of claim 9, wherein forming the fistula between the first passage and the second passage comprises:
   inserting a launching catheter into the first passage, the launching catheter comprising:
      an ultrasound emitting transducer, and
      a needle configured to radially extend from the launching catheter;
   inserting a target catheter into the second passage, the target catheter comprising an ultrasound receiving transducer;
   emitting an ultrasound signal from the ultrasound emitting transducer;
   after the ultrasound signal is received by the ultrasound receiving transducer, extending the needle from the launching catheter, wherein extending the needle comprises:
      exiting the first passage,
      traversing interstitial tissue between the first passage and the second passage, and
      entering the second passage.

14. The method of claim 13, wherein forming the fistula between the first passage and the second passage comprises identifying signal alignment peaks on a display device.

15. The method of claim 14, wherein identifying the signal alignment peaks on the display device comprises identifying a color indicative that the signal alignment peaks are greater than a threshold value.

16. The method of claim 13, wherein forming the fistula between the first passage and the second passage comprises identifying an audible signal indicative that signal alignment is greater than a threshold value.

17. The method of claim 13, wherein the target catheter comprises a target device, wherein forming the fistula between the first passage and the second passage comprises expanding the target device, and wherein extending the needle comprises puncturing the target device.

18. The method of claim 9, wherein forming the fistula between the first passage and the second passage comprises deploying a prosthesis, wherein after deploying the prosthesis at least a first portion of the prosthesis is in the first passage and at least a second portion of the prosthesis is in the second passage.

19. The method of claim 18, wherein the prosthesis comprises a stent graft.

20. The method of claim 19, wherein the stent graft comprises, in a radially expanded state:
- a first portion comprising:
  - a cylindrical shape,
  - a first length, and
  - a first diameter; and
- a second portion adjacent to the first portion, the second portion comprising:
  - a frustoconical shape,
  - a second length longer than the first length,
  - a narrowest diameter, and
  - a widest diameter larger than the first diameter.

* * * * *